United States Patent

Cama et al.

[11] Patent Number: 5,538,964
[45] Date of Patent: Jul. 23, 1996

[54] 3-THIOHETEROARYL 1-CARBA-1-DETHIACEPHALOSPORIN COMPOUNDS, COMPOSITIONS AND METHODS OF USE

[75] Inventors: Lovji D. Cama, Teaneck; Milton L. Hammond, Somerville; Mary F. Sasor, East Windsor, all of N.J.

[73] Assignee: Merck & Co., Inc., Rahway, N.J.

[21] Appl. No.: 463,489

[22] Filed: Jun. 5, 1995

Related U.S. Application Data

[62] Division of Ser. No. 391,857, Feb. 22, 1995.

[51] Int. Cl.⁶ .................. C07D 487/04; A61K 31/435
[52] U.S. Cl. ............................... 514/210; 540/205
[58] Field of Search .................. 540/205, 222, 540/227, 209; 514/202, 206, 210

[56] References Cited

U.S. PATENT DOCUMENTS

| | | |
|---|---|---|
| 3,843,641 | 10/1974 | Christensen et al. . |
| 3,925,363 | 12/1975 | Cama . |
| 4,014,873 | 3/1977 | Christensen et al. . |
| 4,035,359 | 7/1977 | Christensen et al. . |
| 4,041,029 | 8/1977 | Firestone et al. . |
| 4,058,661 | 11/1977 | Cama et al. . |
| 4,071,529 | 1/1978 | Christensen et al. . |
| 4,102,882 | 7/1978 | Firestone et al. . |
| 4,107,432 | 8/1978 | Christensen et al. . |
| 4,123,528 | 10/1978 | Cama et al. . |
| 4,150,156 | 4/1979 | Beattie et al. . |
| 4,154,845 | 5/1979 | Christensen et al. . |
| 4,218,459 | 8/1980 | Cama et al. . |
| 4,219,462 | 8/1980 | Christensen et al. . |
| 4,267,188 | 5/1981 | Cama et al. . |
| 4,321,197 | 3/1982 | Cama et al. . |
| 4,324,890 | 4/1982 | Christensen et al. . |
| 4,338,437 | 7/1982 | Christensen et al. . |
| 4,595,750 | 6/1986 | Christensen et al. . |
| 4,617,152 | 10/1986 | Christensen et al. . |
| 4,734,497 | 3/1988 | Christensen et al. . |
| 4,775,669 | 10/1988 | Cama et al. . |
| 5,272,265 | 12/1993 | Hornback et al. . |
| 5,276,024 | 1/1994 | Schneider et al. . |
| 5,338,843 | 8/1994 | Quante et al. . |
| 5,362,724 | 11/1984 | Kubota et al. . |

FOREIGN PATENT DOCUMENTS

560365A1  9/1993  European Pat. Off. .

*Primary Examiner*—Nicholas Rizzo
*Attorney, Agent, or Firm*—Richard C. Billups; Mark R. Daniel

[57] ABSTRACT

1-Carba-1-dethiacephalosporin compounds of the formula I

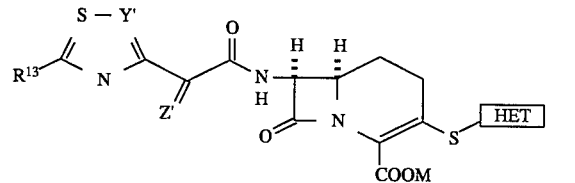

are disclosed. The compounds are useful against MRSA/MRCNS.

Compositions and methods of use are also included.

13 Claims, No Drawings

3-THIOHETEROARYL 1-CARBA-1-DETHIACEPHALOSPORIN COMPOUNDS, COMPOSITIONS AND METHODS OF USE

CROSS REFERENCE TO RELATED APPLICATIONS

This application is a divisional application of U.S. patent application Ser. No. 08/391,857 filed on Feb. 22, 1995, copending herewith, priority of which is claimed hereunder.

BACKGROUND OF THE INVENTION

The present invention relates to antibacterial agents of the 1-carba-1-dethiaceph-3-em-4-carboxylate (Carbaceph)class in which the six membered ring of the nucleus is substituted with a thioheteroaryl group at position three.

Cephoxitin was an early cephalosporin antibacterial agent having a broad spectrum; it has the following formula:

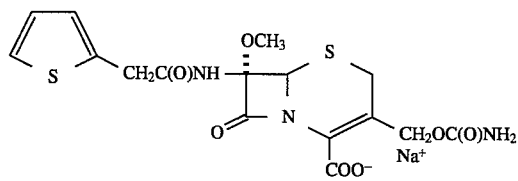

The 1-carba-1-dethiaceph-3-em-4-carboxylate compounds of the present invention have activity against gram positive and gram negative microorganisms, and are useful against methicillin resistant Staphylococcus aureus (MRSA), methicillin resistant Staphylococcus epidermidis (MRSE), and methicillin resistant coagulase negative Staphylococci (MRCNS). The antibacterial compounds of the present invention thus comprise an important contribution to therapy for these difficult to control pathogens.

Moreover, there is an increasing need for agents effective against such pathogens (MRSA/MRCNS) which are at the same time safe, i.e., relatively free from undesirable side effects.

SUMMARY OF THE INVENTION

The present invention addresses a compound represented by formula I:

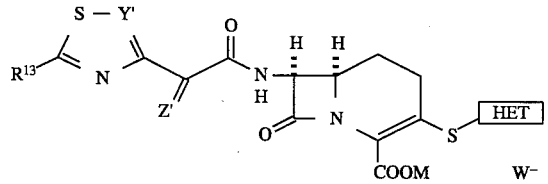

or a pharmaceutically acceptable salt or solvate thereof.

Y' represents CH or N.

M represents hydrogen, a negative charge, a biolabile ester forming group or a carboxyl protecting group.

$R^{13}$ represents $R^1$ or $N(R^1)_2$.

W— is present or absent, and when present, represents a negatively charged counterion.

Z' represents (a) $CR^{y'}R^{z'}$ wherein $R^{y'}$ and $R^{z'}$ independently represent H, $C_{1-6}$ alkyl or $C_{3-8}$ cycloalkyl, each optionally substituted with 1-3 groups selected from $R^{e'}$, or (b) N substituted with $OR^1$ with $R^1$ equal to H, $C_{1-6}$ alkyl, $C_{1-6}$ alkyl substituted with from 1-3 groups selected from $R^{e'}$; $C_{3-8}$ cycloalkyl, $C_{3-8}$ cycloalkenyl, $C_{3-8}$ cycloalkyl substituted with 1-3 groups selected from $R^{e'}$, or $C_{3-8}$ cycloalkenyl substituted with from 1-3 groups selected from $R^{e'}$.

$R^{e'}$ represents a member selected from the group consisting of:

a) $-CF_3$;

b) a halogen atom selected from the group consisting of —Br, —Cl, —F and —I;

c) $-OC_{1-4}$ alkyl, wherein the alkyl portion thereof is optionally substituted by 1-3 groups selected from $R^q$. $R^q$ is selected from the group consisting of hydroxy, methoxy, cyano, $-C(O)NH_2$, $-C(O)NHC_{1-4}$ alkyl, $-C(O)N(C_{1-4}$ alkyl$)_2$, $-OC(O)NH_2$, $-CHO$, $-OC(O)NHC_{1-4}$ alkyl, $-OC(O)N(C_{1-4}$ alkyl$)_2$, $-SO_2NH_2$, $-SO_2N(C_{1-4}$ alkyl$)_2$, $-S(O)C_{1-4}$ alkyl, $-SO_2C_{1-4}$ alkyl, —F, $-CF_3$, $-SO_3M^b$ with $M^b$ representing H or an alkali metal, and $-CO_2M^a$, where $M^a$ is H, alkali metal, methyl or phenyl; tetrazolyl (where the point of attachment is the carbon atom of the tetrazole ring and one of the nitrogen atoms is optionally substituted by 1-3 of the other $R^q$ groups as defined above);

d) —OH;

e) $-OC(O)R^s$, where $R^s$ is $C_{1-4}$ alkyl or phenyl, each of which is optionally substituted by 1-3 groups $R^q$ as defined above; $-OC(O)N(R^{y''})R^{z''}$, where $R^{y''}$ and $R^{z''}$ are independently H, $C_{1-4}$ alkyl, (optionally substituted by 1-3 $R^q$ groups as defined above), or are taken together to represent a 3- to 5-membered alkylidene radical which forms a ring (optionally substituted with $R^q$ as defined above), or a 2- to 4-membered alkylidene radical interrupted by —O—, —S—, —S(O)— or—$S(O)_2$— which forms a ring, said ring being optionally substituted with 1-3 groups $R^q$ as defined above;

g) $-S(O)_n-R^s$, where n=0—2, and $R^s$ is defined above;

h) $-SO_2N(R^{y''})R^{z''}$, where $R^{y''}$ and $R^{z''}$ are as defined above;

i) $-N_3$;

j) $-NR^x_{(0-1)}R^yR^z$ wherein $R^x$, $R^y$ and $R^z$ independently represent H, $C_{1-4}$ alkyl or $C_{1-4}$ alkyl substituted with from 1-3 $R^q$ groups, or $R^x$, $R^y$ and $R^z$ are taken together to represent either a 3- to 7-membered heterocyclic or heteroaryl ring, optionally substituted with 1-3 $R^q$ groups, or a 2- to 4- membered alkylidene radical interrupted by N, O or $S(O)_x$ with x equal to 0, 1 or 2, to form a ring, said alkylidene being optionally substituted with from 1 to 3 $R^q$ groups, such that when $R^x$, $R^y$ and $R^z$ are present, $NR^xR^yR^z$ is a quaternary nitrogen containing group which may be part of a ring;

or $R^x$, $R^y$ and $R^z$ are taken in combination to represent a $C_4$ to $C_{10}$ alkanetriyl group, optionally substituted with 1-3 $R^q$ groups, said alkanetriyl group being optionally interrupted with 1-3 heteroatoms selected from $N^+R^t$, O and $S(O)_x$ with x and $R^{e'}$ as defined above;

k) $-N(R^t)C(O)H$, where $R^t$ is H or $C_{1-4}$ alkyl, said alkyl group being optionally substituted with 1-3 groups $R^q$ as defined above;

l) $-N(R^t)C(O)C_{1-4}$ alkyl, wherein $R^t$ is as defined above;

m) $-N(R^t)C(O)OC_{1-4}$ alkyl, where $R^t$ is as defined above;

n) $-N(R^t)C(O)N(R^y)R^z$ where $R^t$, $R^y$ and $R^z$ are defined above;

o) —N(R$^t$)SO$_2$R$^s$, where R$^s$ and R$^t$ are as defined above;

p) —CN;

q) a formyl or acetalized formyl radical which is —C(O)H or —CH(OCH$_3$)$_2$;

r) —C(OCH$_3$)$_2$ C$_{1-4}$ alkyl, where the alkyl is optionally substituted by 1–3 groups R$^q$ as defined above;

s) —C(O)R$^s$, where R$^s$ is as defined above;

t) —(C=NOR$^{z''}$)R$^{y''}$ where R$^{y''}$ and R$^{z''}$ are as defined above, except they may not be joined together to form a ring;

u) —C(O)OC$_{1-4}$ alkyl, where the alkyl is optionally substituted by 1–3 groups R$^q$ as defined above;

v) —C(O)N(R$^{y''}$)R$^{z''}$, where R$^{y''}$ and R$^{z''}$ are as defined above;

w) —C(O)N(OR$^{y''}$)R$^{z''}$, where R$^{y''}$ and R$^{z''}$ are as defined above, except they may not be joined together to form a ring;

x) —C(S)N(R$^{y''}$)R$^{z''}$ where R$^{y''}$ and R$^{z''}$ are as defined above;

y) —COOM$^a$ where M$^a$ represents H, C$_{1-4}$ alkyl, phenyl or an alkali metal;

z) —SCN;

aa) —SCF$_3$;

ab) tetrazolyl, where the point of attachment is the carbon atom of the tetrazole ring and one of the nitrogen atoms is substituted by hydrogen, an alkali metal or a C$_{1-4}$ alkyl optionally substituted by R$^q$ as defined above;

ac) an anionic function which is selected from the group consisting of: P=O(OM$^a$)$_2$; P=O(OM$^a$)-[O(C$_{1-4}$ alkyl)]; P=O(OM$^a$)-(C$_{1-4}$ alkyl); P=O(OM$^a$)N(R$^{y''}$)R$^{z''}$; P=O(OM$^a$)NHR$^{x'}$; SO$_2$M$^a$; SO$_3$M$^a$; SO$_2$NM$^a$CON(R$^{y''}$)R$^{z''}$, and SO$_2$NM$^a$CN, where R$^{x'}$ is phenyl or heteroaryl, said heteroaryl group being a monocyclic, aromatic hydrocarbon group having 5 or 6 ring atoms, in which a carbon atom is the point of attachment, one of the carbon atoms has been replaced by a nitrogen atom, one carbon atom is optionally replaced by a heteroatom selected from O or S, and from 1 to 3 additional carbon atoms are optionally replaced by nitrogen heteroatoms, and where the phenyl and heteroaryl are optionally substituted by 1–3 groups R$^q$, said R$^q$, M$^a$, R$^{y''}$ and R$^{z''}$ are as defined above;

ad) a C$_{3-7}$ cycloalkyl group;

ae) a C$_{5-7}$ cycloalkyl group in which one of the carbon atoms in the ring is replaced by a heteroatom selected from O, S, NH, or N(C$_{1-4}$ alkyl) and in which one additional carbon may be replaced by the NH or N(C$_{1-4}$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

af) a C$_{2-4}$ alkenyl radical, optionally substituted by 1–3 of the substituents a) to ac) above and phenyl which is optionally substituted by R$^q$ as defined above;

ag) a C$_{2-4}$ alkynyl radical, optionally substituted by 1–3 of the substituents a) to ac) above;

ah) a C$_{1-4}$ alkyl radical;

ai) a C$_{1-4}$ alkyl group substituted by 1–3 of the substituents a)–aa) above;

aj) a C$_{1-4}$ alkyl radical substituted with 1–3 groups selected from aryl, oxime, heteroaryl, C$_{3-7}$ cycloalkyl and heterocycloalkyl, each of which is unsubstituted or substituted with 1 to 3 R$^q$ groups;

ak) a C$_{3-7}$ cycloalkyl radical substituted with 1–3 of the substituents a)–aa) above;

al) a C$_{3-7}$ heterocycloalkyl radical substituted with 1–3 of the substituents a)–aa) above;

am) a C$_{6-10}$ aryl radical;

an) a C$_{6-10}$ aryl radical substituted with 1–3 of the substituents a)–aa) above;

ao) a 6–10 membered heteroaryl radical; and ap) a 6–10 membered heteroaryl radical substituted with 1–3 of the substituents a)–aa) above.

HET represents a heterocyclic group with from one to three positively charged atoms, and is selected from the group consisting of:

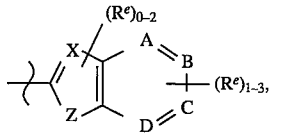

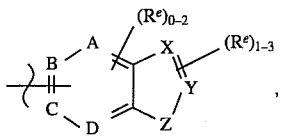

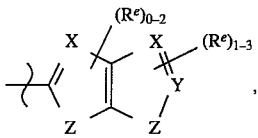

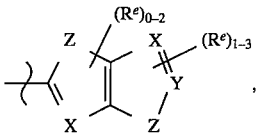

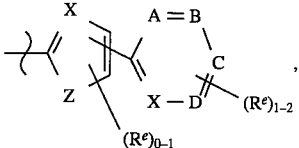

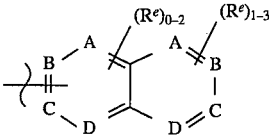

and

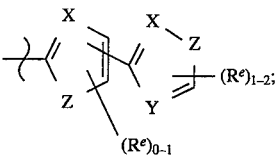

represents the point of attachment to S;

A, B, C, D, X and Y independently represent C or N; Z independently represents O, S or N, such that when Z is absent, at least one of A, B, C, D, X and Y represents N;

one to three $R^e$ groups are present;

one $R^e$ represents —R* and the others represent H, $R^{e'}$ or $R^f$.

—R* represents one of the groups (a) through (c):

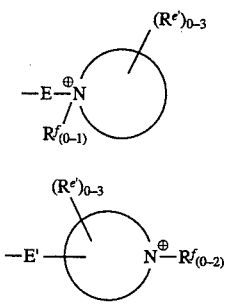

When —R* represents

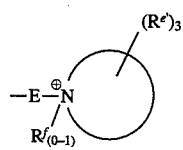

E represents $—(CR^3R^4)_r—Q—(CR^3R^4)_s—$ wherein r is 0–6, s is 1–6;

Q represents a member selected from the group consisting of: a covalent bond, —O—, $—S(O)_x—$ with x equal to 0, 1 or 2, $—NR^3$, $—SO_2NR^3—$, $—NR^3SO_2—$, $—C(O)NR^3—$, $—NR^3C(O)—$, $—CR^3=CR^4—$, —C(O)—, —OC(O)—, —(O)CO—,

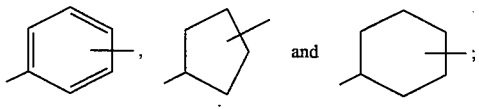

with $R^3$ and $R^4$ independently represent H or $C_{1-4}$ lower alkyl, and $(CR^3R^4)_s—$ being attached to the ring nitrogen.

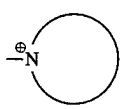

represents a 5 or 6 membered monocyclic heterocycle or an 8–10 membered bicyclic heterocycle, bonded to E through the ring nitrogen and having a substituent group $R^f$ optionally attached to the ring nitrogen, and having 0–3 $R^{e'}$ groups attached to other atoms of the heterocyclic group, said ring nitrogen being tertiary or quaternary by virtue of E, the ring bonds and the optional $R^f$ which may be attached, said heterocyclic group being aromatic, partially aromatic or non-aromatic.

The heterocycle also contains 0–3 additional nitrogen atoms and 0–1 oxygen or sulfur atom.

Each $R^f$ independently represents hydrogen, $—NH_2$, —O—, $—C_{1-4}$ alkyl, optionally substituted with 1–3 groups selected from $R^q$; $—C_{3-7}$ cycloalkyl, optionally substituted with 1–3 groups selected from $R^q$; $—C_{5-7}$ cycloalkyl group in which one of the carbon atoms in the ring is replaced by a heteroatom selected from O, S, NH, or $N(C_{1-4}$ alkyl) and in which one additional carbon may be replaced by the NH or $N(C_{1-4}$ alkyl), and in which at least one carbon atom adjacent to each nitrogen heteroatom has both of its attached hydrogen atoms replaced by one oxygen thus forming a carbonyl moiety and there are one or two carbonyl moieties present in the ring; a $C_{2-4}$ alkenyl radical, optionally substituted by 1–3 substituents $R^q$; a $C_{2-4}$ alkynyl radical, optionally substituted by 1–3 substituents selected from $R^q$; a $C_{1-4}$ alkyl radical substituted with 1–3 groups selected from aryl, oxime, heteroaryl, $C_{3-7}$ cycloalkyl and heterocycloalkyl, each of which is unsubstituted or substituted with 1 to 3 groups selected from $R^q$; a $C_{3-7}$ cycloalkyl radical optionally substituted with 1–3 substituents selected from $R^q$; a $C_{6-10}$ aryl radical, optionally substituted with 1–3 substituents selected from $R^q$; and a 6–10 membered heteroaryl group, optionally substituted with 1–3 substituents selected from $R^q$.

When —R* represents

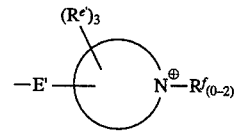

E' represents $—(CR^3R^4)_{m'}—Q—(CR^3R^4)_{m'}—$ with each m' independently equal to 0–6, and Q, $R^3$ and $R^4$ as defined above, except that when each m' is 0, Q is not a covalent bond, and $—(CR^3R^4)_{m'}$ attached to the heterocyclic ring.

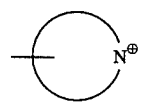

represents a 5 or 6 membered monocyclic heterocycle or an 8–10 membered bicyclic heterocycle, said heterocycle being aromatic, partially aromatic or non-aromatic, bonded to E' through an atom other than the ring nitrogen, and having 0–2 $R^f$ groups attached to the ring nitrogen, said nitrogen in the heterocycle being tertiary or quaternary by virtue of the ring bonds and the optional $R^f$ groups which may be attached.

The heterocycle further contains 0–1 oxygen or sulfur atom and 0–2 additional nitrogen atoms therein.

$R^{e'}$ and $R^f$ are as defined above.

When —R* represents (c) $—E_p—N+R^{10}R^{11}R^{12}(0-1)$,

E is as defined above and p is an integer 0 or 1.

$R^{10}$, $R^{11}$ and when present, $R^{12}$, are independently H, $C_{1-4}$ alkyl or $C_{1-4}$ alkyl substituted with 1–3 $R^q$ groups, such that when $R^{12}$ is present, the N is quaternary, and when $R^{12}$ is absent, the N is tertiary;

or $R^{10}$ and $R^{11}$ are taken together to represent a $C_{3-7}$ alkylidene radical to form a ring (optionally substituted with 1–3 $R^q$ groups as defined below), uninterrupted or interrupted by O, S, S(O), $SO_2$, $N(O)R^{e'}$ or $N^+(R^{e'})_{1-2}$ (where $R^{e'}$ is as previously defined), or $R^{10}$, $R^{11}$ and $R^{12}$ are taken in combination to represent a $C_4$ to $C_{10}$ alkanetriyl group, optionally substituted with 1–3 $R^{e'}$ groups, said alkanetriyl group being optionally interrupted with 1–3 heteroatoms selected from $N^+R^{e'}$, O and $S(O)_x$ with x and $R^{e'}$ as defined above.

Also included are pharmaceutical compositions which are comprised of a compound of formula I in combination with a pharmaceutically acceptable carrier.

Also included are methods of use which are comprised of administering to a mammal in need of such treatment a compound in accordance with formula I in an amount effective to treat a bacterial infection.

DETAILED DESCRIPTION OF THE INVENTION

The invention is described herein in detail using the terms defined below unless otherwise specified.

Carboxylic acid refers to —COOH.

Carboxylate anion refers to a negatively charged group —COO—.

An N-hydroxycarbamoyl or N($C_{1-4}$ alkoxy)carbamoyl radical in which the nitrogen atom may be additionally substituted by a $C_{1-4}$ alkyl group is: —C(O)N(OR$^{y''}$)R$^{z''}$, where R$^{y''}$ and R$^{z''}$ are as defined, except they may not be joined together to form a ring.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, at any available point of attachment. When the alkyl group is said to be substituted with an alkyl group, this is used interchangeably with "branched alkyl group".

The term "alkoxy" refers to a $C_{1-4}$ alkoxy radical: —O$C_{1-4}$ alkyl, wherein the alkyl is optionally substituted by 1–3 groups selected from $R^q$. $R^q$ is selected from hydroxy, methoxy, cyano, —C(O)NH$_2$, —C(O)NHC$_{1-4}$ alkyl, —C(O)N(C$_{1-4}$ alkyl)$_2$, —OC(O)NH$_2$, —CHO, —OC(O)NHC$_{1-4}$ alkyl, —OC(O)N(C$_{1-4}$ alkyl)$_2$, —SO$_2$NH$_2$, —SO$_2$N(C$_{1-4}$ alkyl)$_2$, —S(O)C$_{1-4}$ alkyl, —SO$_2$C$_{1-4}$ alkyl, —F, —CF$_3$, —SO$_3$M$^b$ (with M$^b$ representing H or an alkali metal), and —CO$_2$M$^a$ (where M$^a$ is H, alkali metal, methyl or phenyl); tetrazolyl (where the point of attachment is the carbon atom of the tetrazole ring and one of the nitrogen atoms is optionally substituted by 1–3 $R^q$ groups as defined above). The preferred alkoxy group is methoxy.

A hydroximinomethyl radical in which the oxygen or carbon atom is optionally substituted by a $C_{1-4}$ alkyl group is the group: —C=N(OR$^{z''}$)R$^{y''}$ where R$^{z''}$ represents a $C_{1-4}$ alkyl group and R$^{y''}$ is as previously defined, except they may not be joined together to form a ring.

The term "oxime" and "hydroxyimino" can be used interchangeably to refer to the group: =N—OH. When the oxime is substituted on the hydroxyl portion thereof, this is represented by the structure: =N—OR$^{z''}$. Cycloalkyl is a specie of alkyl containing from 3 to 15 carbon atoms, without altering or resonating double bonds between carbon atoms. It may contain from 1 to 4 rings which are fused. The preferred cycloalkyl groups are cyclopentyl and cyclohexyl.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

Cycloalkenyl is a subset of alkenyl, containing from 5 to 10 carbon atoms, in one or two fused rings, with at least one carbon to carbon double bond.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, groups as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms are optionally replaced by a heteroatom selected from O or S, and in which from 1 to 3 additional carbon atoms are optionally replaced by nitrogen heteroatoms, said heteroaryl group being optionally substituted as described herein.

Heteroaryl thus includes aromatic and partially aromatic groups which contain one or more heteroatoms. Examples of this type are pyrrole, pyridine, oxazole, thiazole and oxazine. Additional nitrogen atoms may be present together with the first nitrogen and oxygen or sulfur, giving, e.g., thiadiazole. Preferred heteroaryl groups are thiazolyl, imidazolyl, pyridyl and pyrrolyl.

Heteroarylium groups are those heteroaryls which contain one or more quaternary nitrogen atoms.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said heteroatoms. Preferred heterocycloalkyl groups include piperidinyl, pyrrolidinyl and tetrahydrofuranyl. The N atoms of said heterocycloalkyl groups may be tertiary or quaternary.

The term "quaternary nitrogen" refers to a tetravalent positively charged nitrogen atom including, e.g., the positively charged nitrogen in a tetraalkylammonium group (e.g. tetramethylammonium, N-methylpyridinium), the positively charged nitrogen in protonated ammonium species (e.g. trimethylhydroammonium, N-hydropyridinium), the positively charged nitrogen in amine N-oxides (e.g. N-methylmorpholine-N-oxide, pyridine-N-oxide), and the positively charged nitrogen in an N-amino-ammonium group (e.g. N-aminopyridinium).

In —R*, when the —R* represents (a), and there is no —R$^f$ group present on the nitrogen atom which is shown, the nitrogen is quaternary when the ring containing said nitrogen is aromatic, by virtue of the ring bonds and bond to E'. Likewise, when R$^f$ is absent and the ring bonds and bond to E provide for 3 bonds to the nitrogen atom, the nitrogen is tertiary and not positively charged.

In —R*, when the —R* represents (b), and there is one —R$^f$ group present on the nitrogen atom which is shown, the nitrogen is quaternary when the ring containing said nitrogen is aromatic, by virtue of the ring bonds and the bond to R$^f$. Likewise, when R$^f$ is absent and the ring is aromatic, the nitrogen is tertiary and not positively charged. When the ring is non-aromatic and one $R^f$ is attached, the nitrogen is non-quaternary. When the ring is non-aromatic and two $R^f$ groups are attached, the ring nitrogen atom shown is quaternary.

The term "heteroatom" means O, S or N, selected on an independent basis.

Halogen and "halo" refer to bromine, chlorine, fluorine and iodine.

The term "alkali metal" refers to species which may be positively charged, such as, for example, Na, K, Ca, Mg and the like.

When a group is termed "substituted", unless otherwise indicated, this means that the group contains from 1 to 4 substituents thereon at any available point of attachment.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, N.Y. (1991). Examples of suitable protecting groups are contained throughout the specification.

In the preparation methods described herein, the carboxyl group at the 4-position typically remains blocked until the ultimate or penultimate step, when the final product is prepared. These blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile and catalytic hydrogenation.

Examples of suitable hydroxyl protecting groups which can be used in the syntheses described herein are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl,-t-butyloxycarbonyl, 2,2,2-trichloroethyloxycarbonyl and allyloxycarbonyl. Preferred hydroxyl protecting groups are trimethylsilyl and triethylsilyl.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. Preferred carboxyl protecting groups include p-nitrobenzyl and p-methoxybenzyl.

In any given structure, where a variable appears more than once, each is to be determined on an independent basis. For example, in the structures:

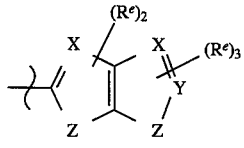

and

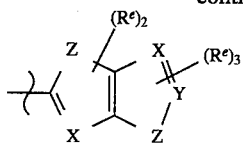

each X, Y and Z is determined independently. Both X's can represent N or C, or one can represent N while the other represents C. Also, each $R^e$ group is determined independently.

A, B, C, D, X and Y independently represent C or N;

Z represents O, S or N, such that when Z is absent, at least one of A, B, C, D, X and Y represents N.

The HET group is aromatic and contains at least one heteroatom. Hence, for any given ring system, at least one of A, B, C, D, X, Y and Z is a heteroarom.

When a variable appears twice, they can be the same or different. Because HET is aromatic, alternating double bonds are drawn. Z is drawn with 2 bonds attached; however, Z may also have 3 bonds when appropriate, when Z is N.

The compounds of the present invention are useful in various pharmaceutically acceptable salt forms for the treatment of bacterial infections in animal and human subjects. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is concerned with pharmaceutical compositions and methods of treating bacterial infections utilizing the compound of formula I.

The compounds of the invention are electronically balanced. Hence the compounds of formula I are ordinarily present in association with an appropriately charged counterion or counterions. Since a bisquaternary ammonium group is present in many of the compounds of the invention, one or two negatively charged counterions are also present to provide overall electronic balance. The other counterion, termed genetically $W^-$, can vary widely, depending upon the particular counterion desired. In the final compound, a single positive charge in the HET group can be balanced by a negatively charged counterion or the negatively charged carboxylate, $CO_2-$, which is attached to the cephalosporin nucleus at position 3. When more than one positive charge is present, a negatively charged counterion is present as well. The counterion $W^-$ is a pharmaceutically acceptable anionic species and may vary widely. The desired counterion $W^-$ may be introduced by standard techniques as described above, such as by conducting an ion exchange. It is understood that when the counterion W— is an anionic species possessing more than one negative charge, then an appropriate amount of $W^-$ is present to result in overall electronic balance with the final compound I. When $W^-$ is dianionic, one-half of a molar equivalent of $W^-$ is present relative to the net positively charged cephalosporin moiety. The pharmaceutically acceptable salt forms of the compounds of formula I mentioned above refer to the various possibilities for the charge balancing counterion $W^-$. Anions derived from inorganic and organic acids are suitable. Representative examples of such counterions are the following: acetate, adipate, aminosalicylate, anhydromethylenecitrate, ascorbate, aspartate, benzoate, benzenesulfonate, bisulfate, bromide, citrate, camphorate, camphorsulfonate, chloride, digluconate, edetate, edisylate, estolate, ethanesulfonate, fumarate, glucoheptanoate, gluconate, glutamate, glycerophosphate, glycolate, hydroxynaphthoate, 2-hydroxyethanesulfonate, iodide, lactate, lactobionate, malate, maleate, mandelate, methylenebis(salicylate), mucate, methanesulfonate, napadisylate, napsylate, pamoate, pantothenate, pectinate, phosphate/diphosphate, polygalacturonate, propionate, salicylate, stearate, succinate, sulfate, tankage, tosylate and undecanoate. Other anionic species will be apparent to the ordinarily skilled chemist.

One subset of compounds of the present invention includes those compounds where Y' represents N.

Another subset of compounds are those in which HET represents:

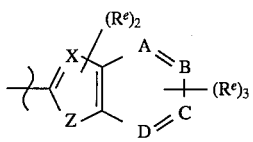

In these compounds, X is preferably a nitrogen atom. The preferred values of A, B, C and D are carbon, thus forming a fused benzene ring, or 1–2 of the variables represent a nitrogen atom, thus forming a fused pyridine, pyrimidine or pyrazine ring. Suitable examples of these ring systems include the following:

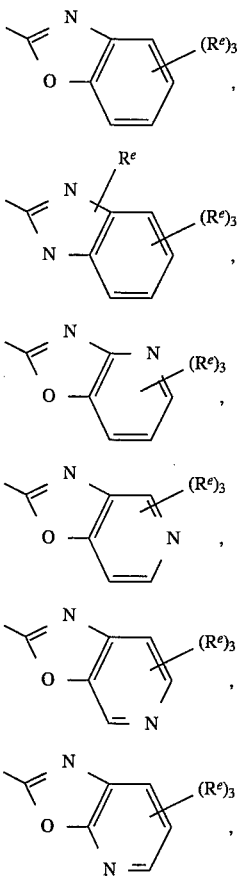

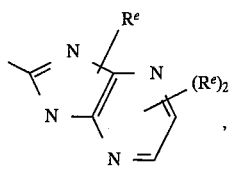

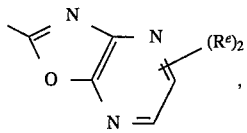

and

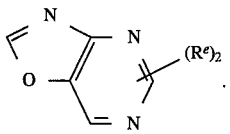

Another subset of compounds of the invention are those in which X is nitrogen and Z represents a sulfur atom. Examples of this ring system include the following:

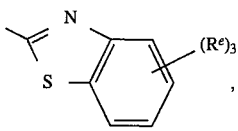

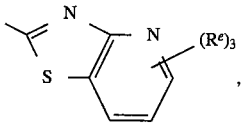

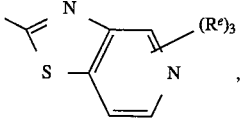

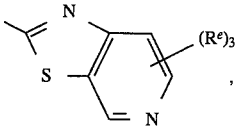

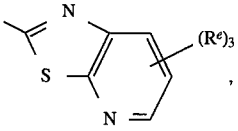

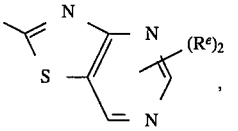

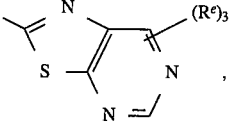

and

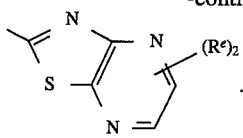

Another subset of compounds are those in which HET represents:

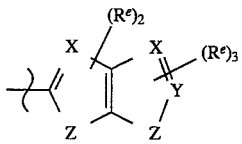

or

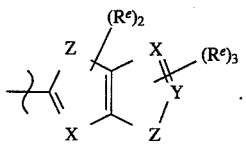

In these compounds, X is preferably a nitrogen atom. A subset of compounds of the invention includes those in which X is nitrogen and Z represents a sulfur atom. Illustrative of this ring system are the following:

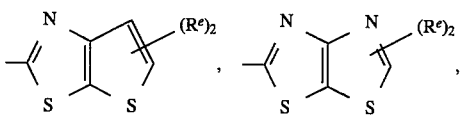

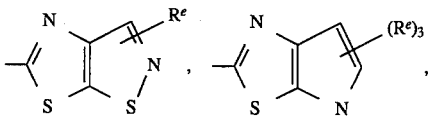

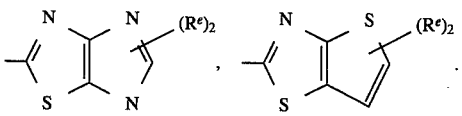

and

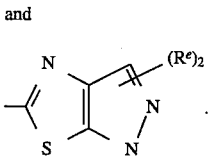

In the compounds of the present invention, one of the $R^e$ groups represents —R*. One subset of —R* is of type (a). Illustrative of this quaternary ring system are the following:

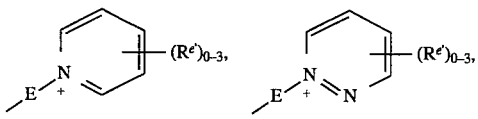

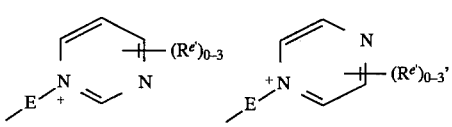

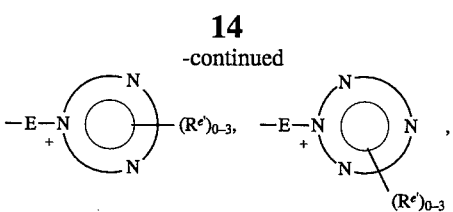

where the ring contains three carbon atoms;   where the ring contains two carbon atoms;

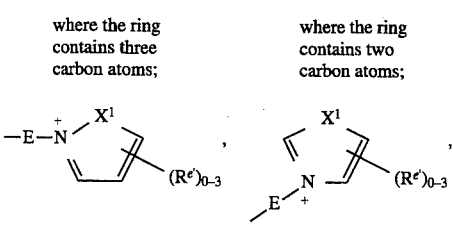

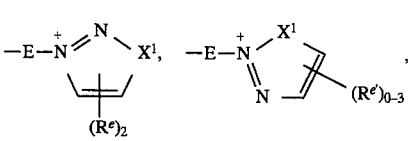

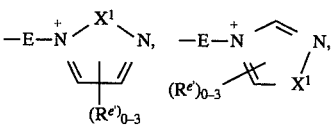

$X^1$ = O, S or C

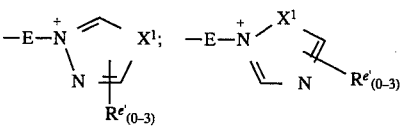

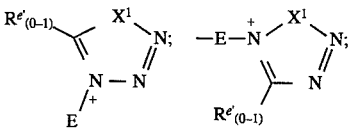

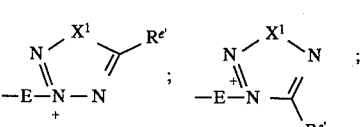

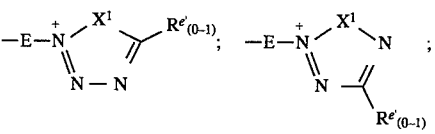

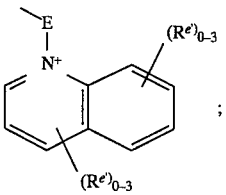

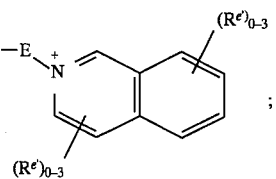

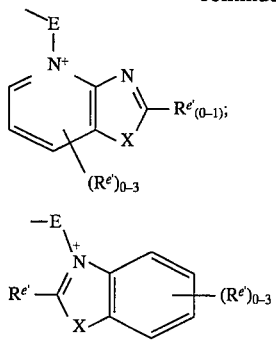

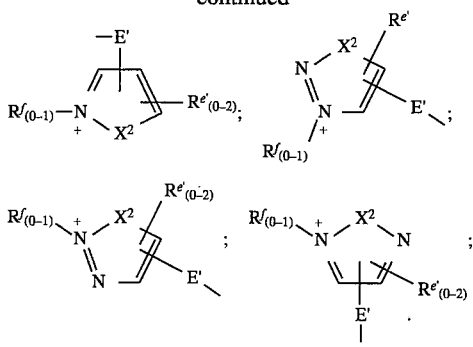

and

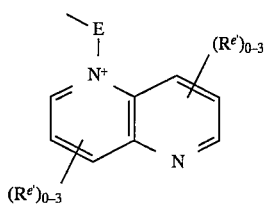

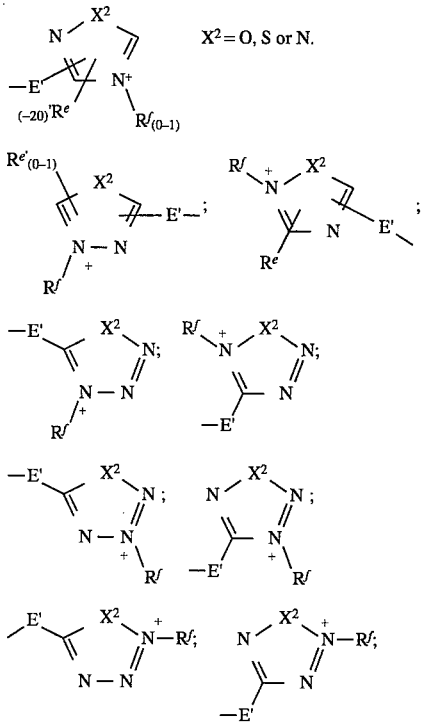

For the structures above, where $R^{e'}$ is shown to have an indefinite position, it is attached to any available atom of the ring. Where two rings are shown and more than 3 $R^{e'}$ groups are shown attached, this means that up to 3 may be included at available points of attachment.

Another subset of compounds includes those compounds where —R* is of type (b):

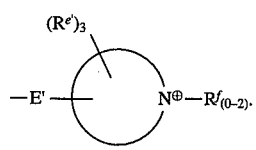

In this subtype, E' is attached to an atom of the aromatic ring other than a nitrogen atom. Illustrative of this subtype are the following:

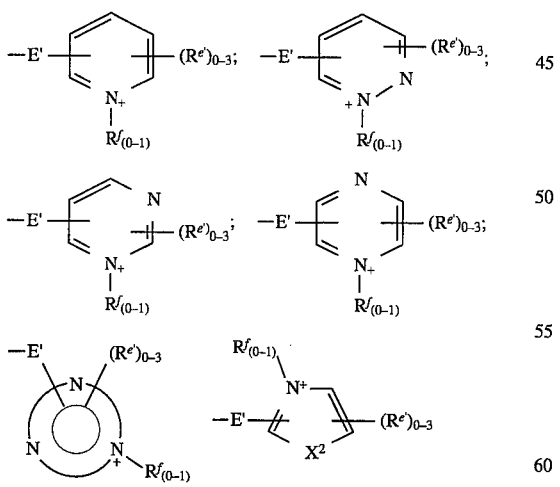

where the ring contains three carbon atoms;

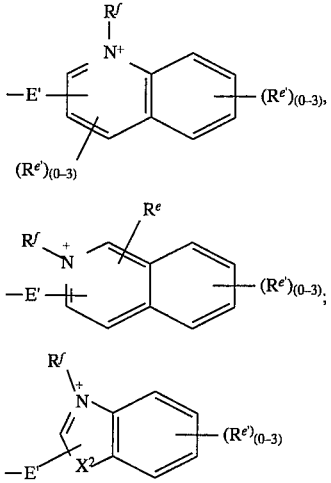

and

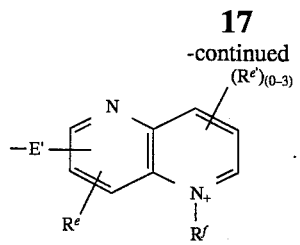

Another subset of compounds of the present invention includes compounds where —R* is of type (c):

—$E_p$—$N^+R^{10}R^{11}R^{12}_{(0-1)}$.

Illustrative of this particular subtype are the following:

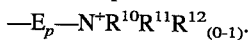

—Ep—$N^+(CH_3)_3$, —Ep—$N^+(CH_2CH_3)_3$, —Ep—$N^+(CH_3)_2CH_2R^q$ —Ep—$N^+(CH_2CH_3)_2CH_2CH_2R^q$,

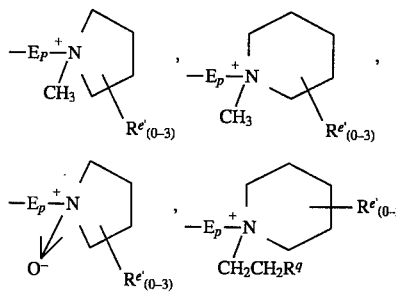

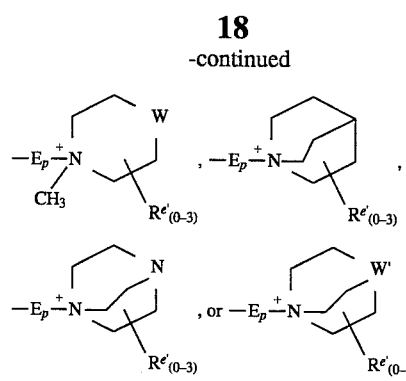

where W is O, S, NH, $NR^{e'}$, $N(O)R^{e'}$, SO, $SO_2$, $NH_2^+$, $NHR^{e'+}$, or $N^+(R^{e'})_2$ and W' is $NH^+$, $N^+R^{e'}$ or NO. Where $R^{e'}$ is shown to have an indefinite position, it may be attached to any available atom of the ring.

Examples of specific compounds falling within the scope of the present invention include those set forth in tables I–III below.

TABLE I

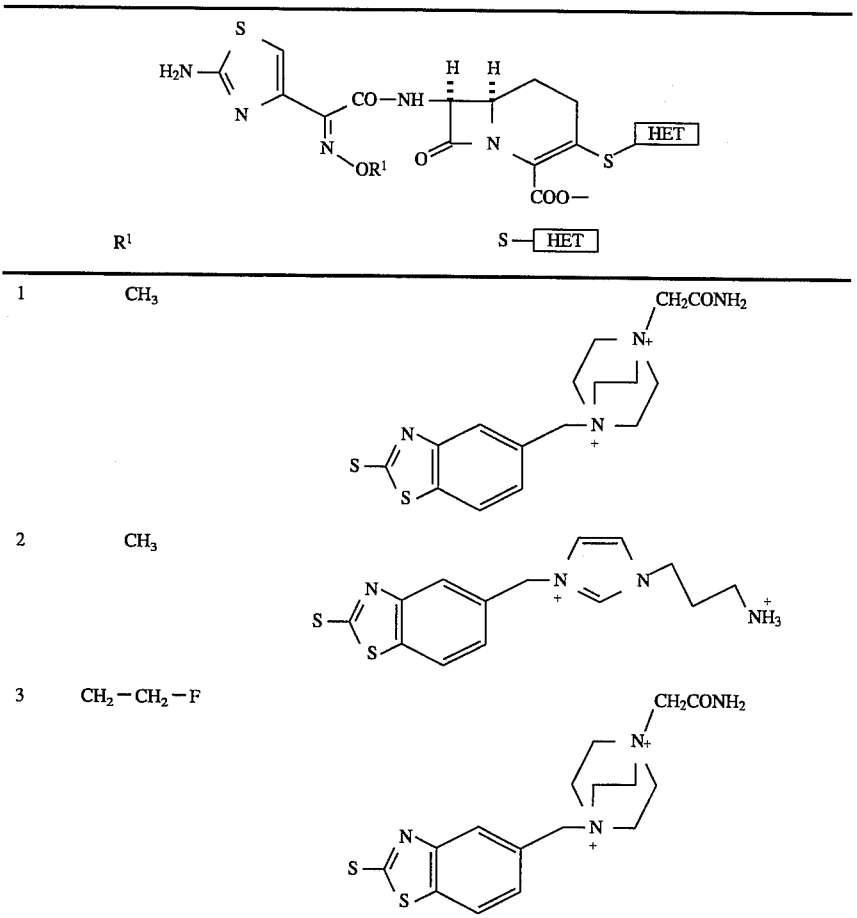

TABLE I-continued

[Structure: H₂N-(S/N thiazole)-C(=N-OR¹)-CO-NH-[β-lactam core]-CH₂-CH₂-[cephem with S-HET and COO⁻]]

| | R¹ | S—HET |
|---|---|---|
| 4 | CH₂—CH₂—F | 2-mercaptobenzothiazol-5-yl-CH₂-N⁺(imidazole)N-CH₂CH₂CH₂-N⁺H₃ |
| 5 | CH₂—CH₂—F | 2-mercaptobenzothiazol-6-yl-CH₂-N⁺(DABCO)-CH₂CONH₂ |
| 6 | CH₂—CH₂—F | 2-mercaptobenzothiazol-6-yl-CH₂-N⁺(imidazole)N-CH₂CH₂CH₂-N⁺H₃ |
| 7 | CH₂—CH₂—F | 2-mercaptobenzothiazol-5-yl-CH₂-N⁺(imidazole)N-CH₂CH₂CH₂-N⁺Me₂-CH₂CONH₂ |
| 8 | CH₂—CH₂—F | 2-mercaptobenzothiazol-7-yl-CH₂-N⁺(DABCO)-CH₂CONH₂ |
| 9 | CH₂—CH₂—F | 2-mercaptobenzothiazol-7-yl-CH₂-N⁺(imidazole)N-CH₂CH₂CH₂-N⁺H₃ |
| 10 | CH₂—CH₂—F | 2-mercaptothiazol-4-yl-CH₂-N⁺(DABCO)-CH₂CONH₂ |

TABLE I-continued

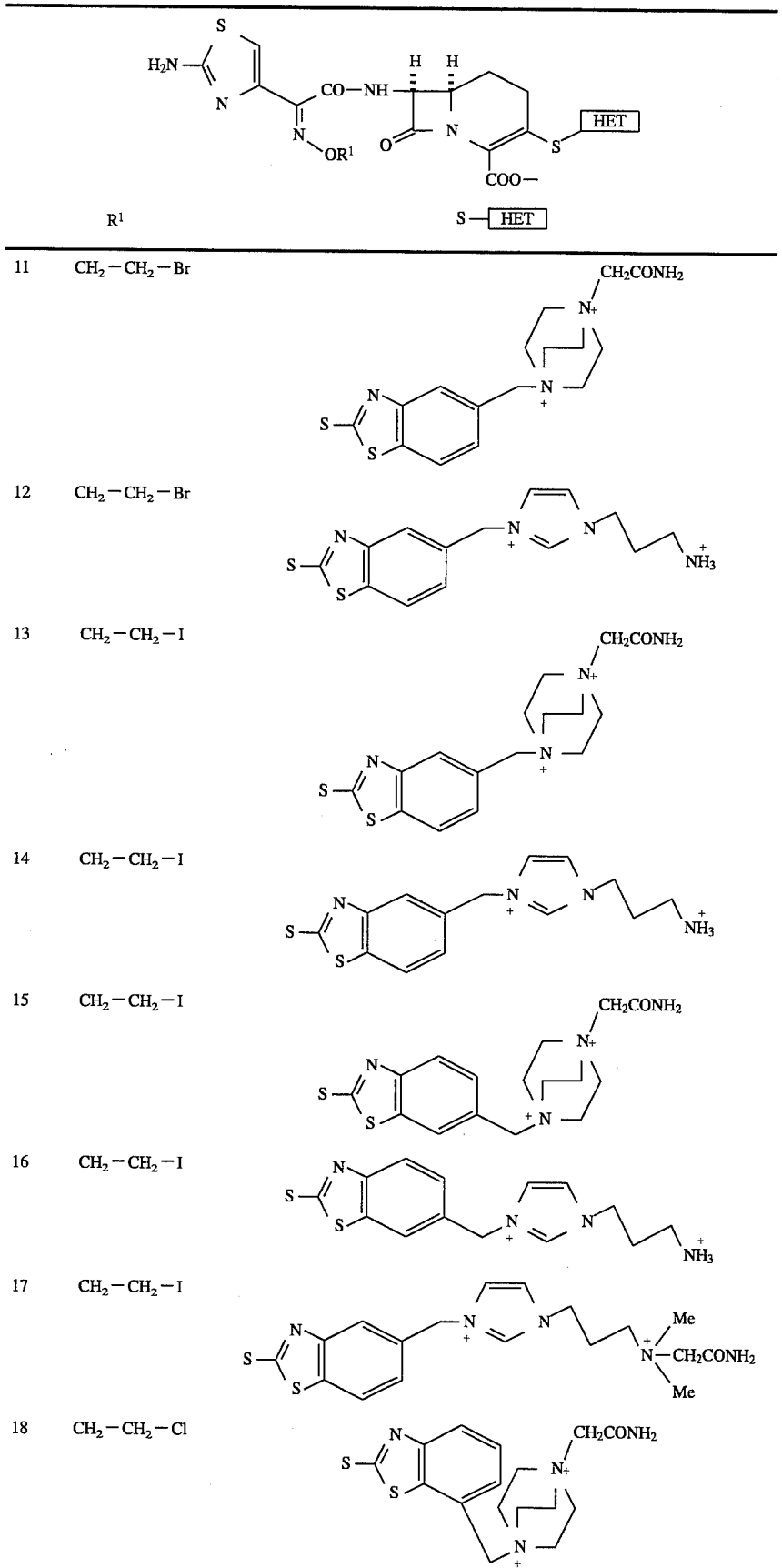

| | R¹ | S—HET |
|---|---|---|
| 11 | CH₂—CH₂—Br | (benzothiazole-S, CH₂-N⁺(bicyclic diamine)-CH₂CONH₂) |
| 12 | CH₂—CH₂—Br | (benzothiazole-S, CH₂-imidazolium-propyl-NH₃⁺) |
| 13 | CH₂—CH₂—I | (benzothiazole-S, CH₂-N⁺(bicyclic diamine)-CH₂CONH₂) |
| 14 | CH₂—CH₂—I | (benzothiazole-S, CH₂-imidazolium-propyl-NH₃⁺) |
| 15 | CH₂—CH₂—I | (benzothiazole-S, CH₂-N⁺(bicyclic diamine)-CH₂CONH₂) |
| 16 | CH₂—CH₂—I | (benzothiazole-S, CH₂-imidazolium-propyl-NH₃⁺) |
| 17 | CH₂—CH₂—I | (benzothiazole-S, CH₂-imidazolium-propyl-N⁺(Me)₂-CH₂CONH₂) |
| 18 | CH₂—CH₂—Cl | (benzothiazole-S, CH₂-N⁺(bicyclic diamine)-CH₂CONH₂) |

TABLE I-continued

| # | R¹ | S—HET |
|---|---|---|
| 19 | CH₂—CH₂—Cl | benzothiazole-S- with imidazolium-CH₂ linker and propyl-NH₃⁺ |
| 20 | CH₂—CH₂—Cl | thiophene-fused dithiole with DABCO-type bicyclic ammonium bearing CH₂CONH₂ |
| 21 | CH₂—F | benzothiazole-S- with DABCO-type bicyclic ammonium bearing CH₂CONH₂ |
| 22 | CH₂—F | benzothiazole-S- with imidazolium and propyl-NH₃⁺ |
| 23 | CH₂—CF₃ | benzothiazole-S- with DABCO-type bicyclic ammonium bearing CH₂CONH₂ |
| 24 | CH₂—CF₃ | benzothiazole-S- with imidazolium and propyl-NH₃⁺ |
| 25 | CH₂—CH₂—CH₃ | benzothiazole-S- with DABCO-type bicyclic ammonium bearing CH₂CONH₂ |

TABLE I-continued
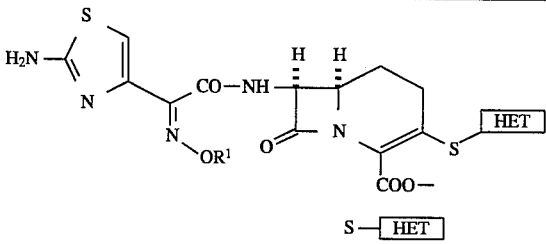
| | R[1] | S—HET |
|---|---|---|
| 26 | $CH_2-CH_2-CH_3$ | 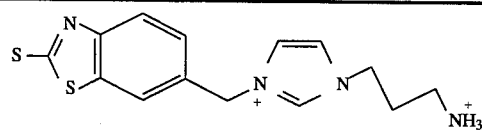 |
| 27 | $CH_2-CH=CCl_2$ | 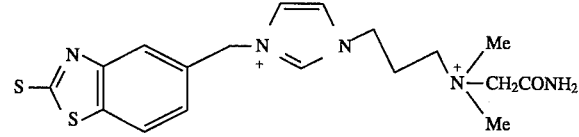 |
| 28 | $CH_2-CH=CCl_2$ | 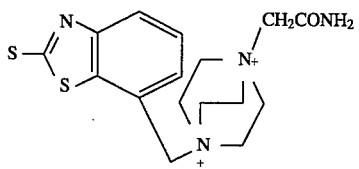 |
| 29 | $CH_2-CH_2-OH$ | 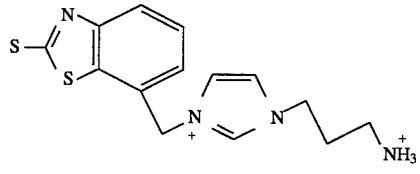 |
| 30 | $CH_2-CH_2-OH$ | 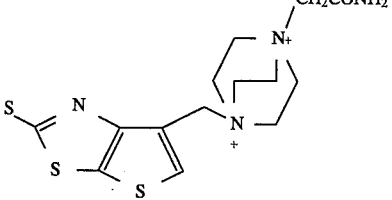 |
| 31 | $CH_2-S-CH_3$ | 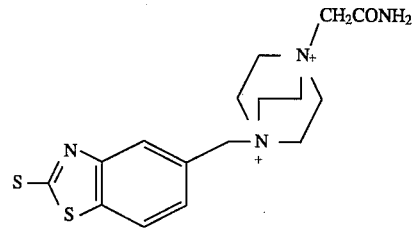 |
| 32 | $CH_2-S-CH_3$ | 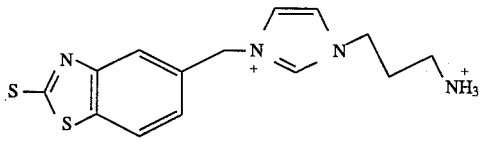 |

TABLE I-continued
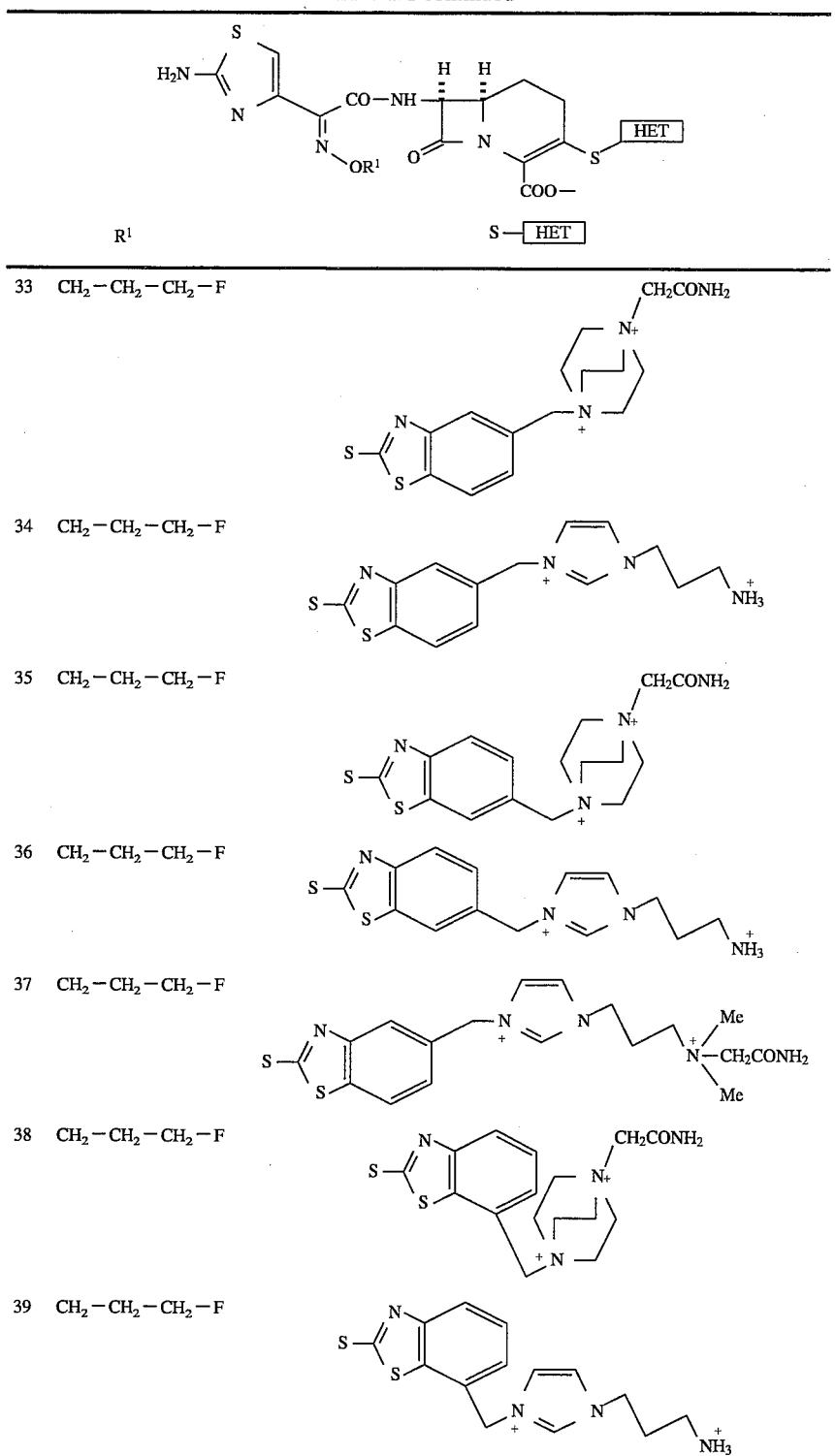

TABLE I-continued

| | $R^1$ | S—HET |
|---|---|---|
| 40 | $CH_2-CH_2-CH_2-F$ | (thiazole-fused thiophene with bicyclic diazoniabicyclo substituent bearing $CH_2CONH_2$) |
| 41 | $CH_2-CH(CH_3)_2$ | (2-mercaptobenzothiazol-5-yl-methyl diazoniabicyclo with $CH_2CONH_2$) |
| 42 | $CH_2-CH(CH_3)_2$ | (2-mercaptobenzothiazol-5-yl-methyl imidazolium propyl-$NH_3^+$) |
| 43 | $CH(CH_3)_3$ | (2-mercaptobenzothiazol-5-yl-methyl diazoniabicyclo with $CH_2CONH_2$) |
| 44 | $CH(CH_3)_3$ | (2-mercaptobenzothiazol-5-yl-methyl imidazolium propyl-$NH_3^+$) |
| 45 | $CH_2-C_6H_5$ | (2-mercaptobenzothiazol-6-yl-methyl diazoniabicyclo with $CH_2CONH_2$) |
| 46 | $CH_2C_6H_5$ | (2-mercaptobenzothiazol-6-yl-methyl imidazolium propyl-$NH_3^+$) |

TABLE I-continued
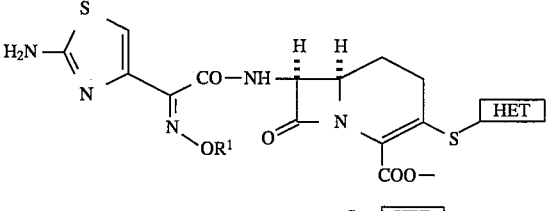
| | R¹ | S—HET |
|---|---|---|
| 47 | CH₂C₆H₅ | 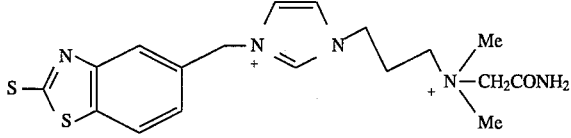 |
| 48 | H | 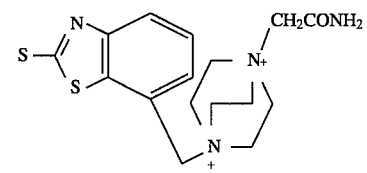 |
| 49 | H | 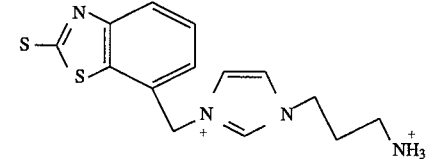 |
| 50 | H | 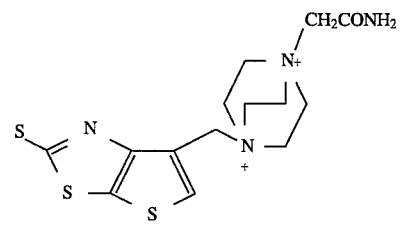 |
| 51 |  | 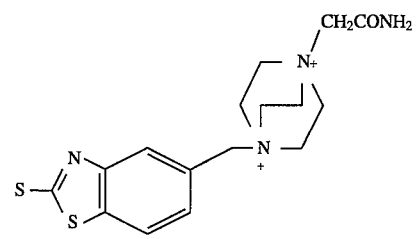 |
| 52 |  | 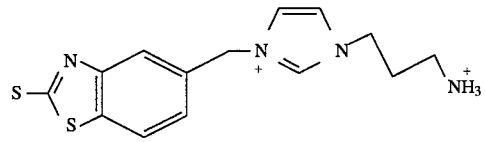 |
| 53 |  | 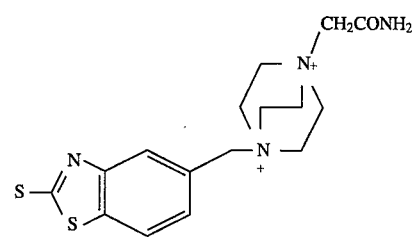 |

TABLE I-continued

| No. | R¹ | S—HET |
|-----|----|----|
| 54 | cyclopentenyl-methyl | benzothiazol-2-ylthio-5-CH₂-N⁺(imidazole)N-CH₂CH₂CH₂-N⁺H₃ |
| 55 | H | benzothiazol-2-ylthio-5-CH₂-N⁺(DABCO)-CH₂CONH₂ |
| 56 | H | benzothiazol-2-ylthio-6-CH₂-N⁺(imidazole)N-CH₂CH₂CH₂-N⁺H₃ |
| 57 | H | benzothiazol-2-ylthio-5-CH₂-N⁺(imidazole)N-CH₂CH₂CH₂-N⁺Me₂-CH₂CONH₂ |
| 58 | 2-ethylphenol | benzothiazol-2-ylthio-5-CH₂-N⁺(DABCO)-CH₂CONH₂ |
| 59 | 2-ethylphenol | benzothiazol-2-ylthio-7-CH₂-N⁺(imidazole)N-CH₂CH₂CH₂-N⁺H₃ |
| 60 | 2-ethylphenol | thiazolo-thiophene-CH₂-N⁺(DABCO)-CH₂CONH₂ |

TABLE I-continued

| | $R^1$ | S—[HET] |
|---|---|---|
| 61 | $CH_2-CH_2-F$ | (benzothiazole-2-thiol-5-yl linked to diazabicyclic N with N⁺–CH₂CN) |
| 62 | $CH_2-CH_2-F$ | (2-mercaptobenzothiazol-4-yl-CH₂–imidazolium–(CH₂)₃–NH₃⁺) |
| 63 | $CH_2-CH_2-F$ | (2-mercaptobenzothiazol-5-yl-diazabicyclic N⁺–CH₂CH₃) |
| 64 | $CH_2-CH_2-F$ | (2-mercaptobenzothiazol-5-yl-CH₂–imidazolium–CH₂CH₂–NH₃⁺) |
| 65 | $CH_2-CH_2-F$ | (2-mercaptobenzothiazol-6-yl-CH₂–diazabicyclic N⁺–CH₂CH₂CH₂OH) |
| 66 | $CH_2-CH_2-F$ | (2-mercaptobenzothiazol-6-yl-CH₂–imidazolium–(CH₂)₃–N⁺(Me)(Me)–CH₂CONH₂) |
| 67 | $CH_2-CH_2-F$ | (2-mercaptobenzothiazol-5-yl-CH₂–imidazolium–(CH₂)₃–N⁺(Me)(Me)–CH₂CN) |

TABLE I-continued
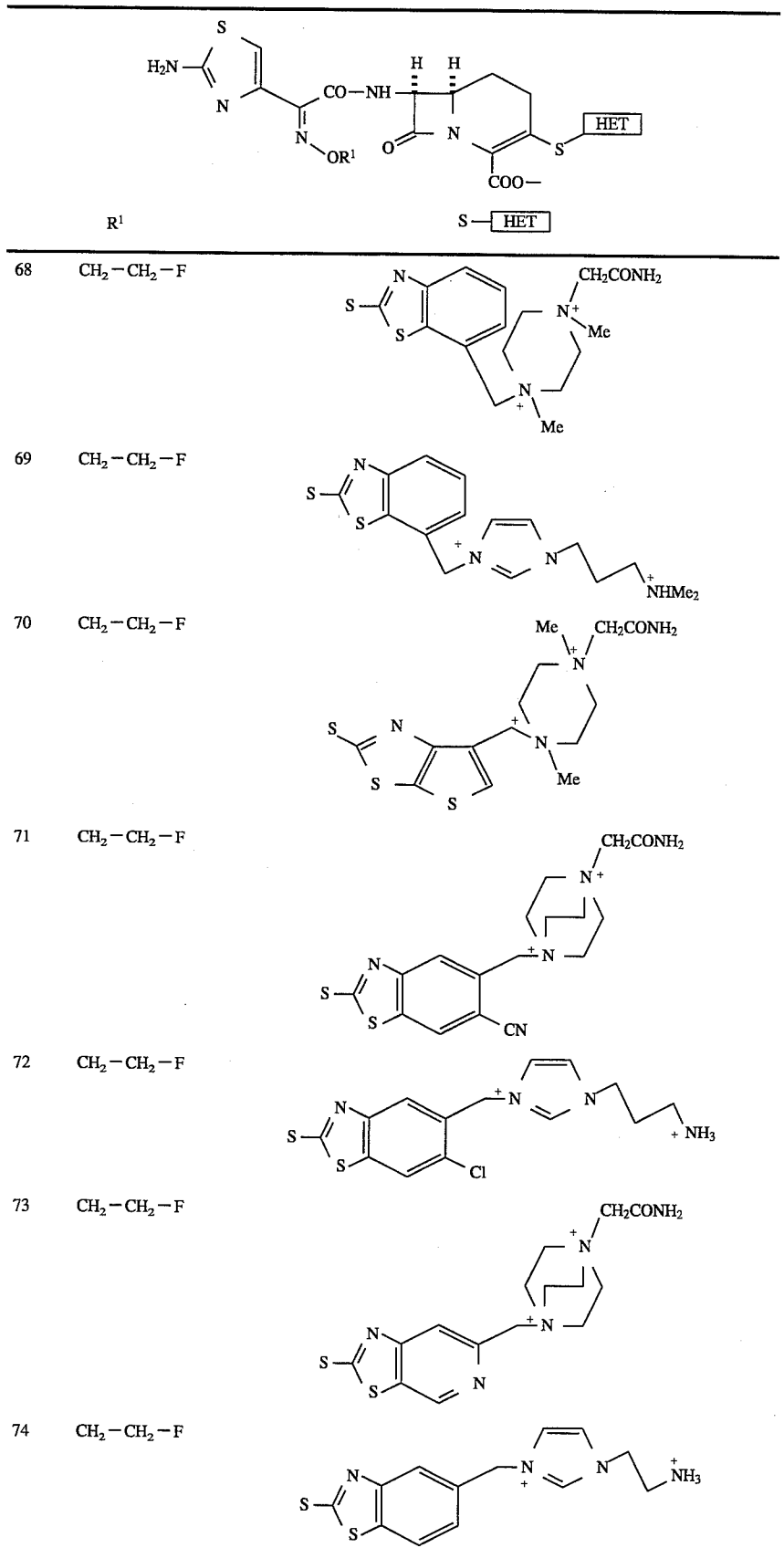
| | R¹ | S—HET |
|---|---|---|
| 68 | $CH_2-CH_2-F$ | |
| 69 | $CH_2-CH_2-F$ | |
| 70 | $CH_2-CH_2-F$ | |
| 71 | $CH_2-CH_2-F$ | |
| 72 | $CH_2-CH_2-F$ | |
| 73 | $CH_2-CH_2-F$ | |
| 74 | $CH_2-CH_2-F$ | |

TABLE I-continued
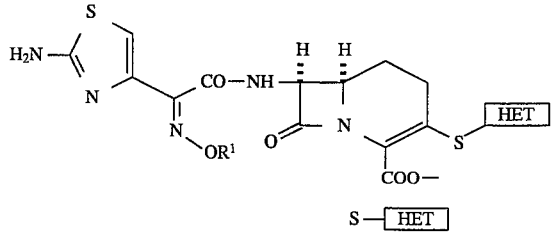
| | $R^1$ | S—[HET] |
|---|---|---|
| 75 | $CH_2-CH_2-F$ | 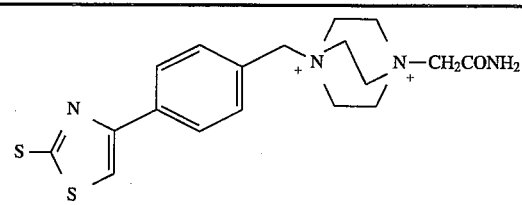 |
| 76 | $CH_2-CH_2-F$ | 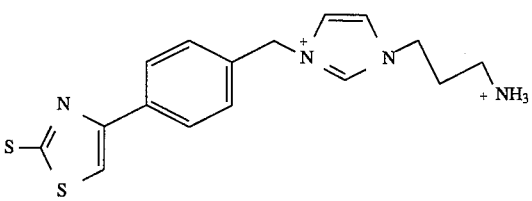 |
| 77 | $CH_2-CH_2-F$ | 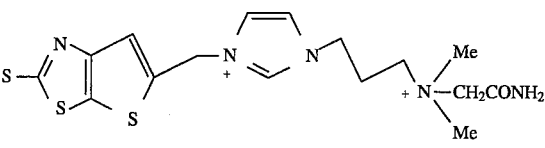 |
| 78 | $CH_2-CH_2-F$ | 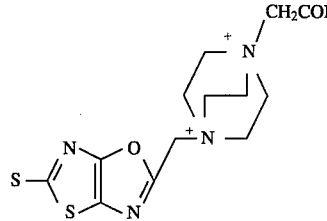 |
| 79 | $CH_2-CH_2-F$ | 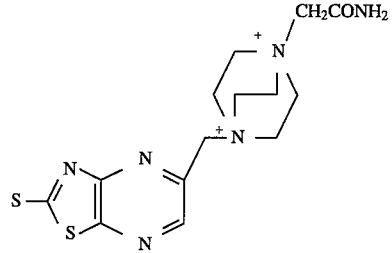 |
| 80 | $CH_2-CH_2-F$ | 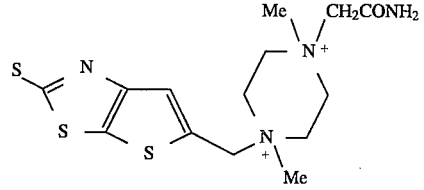 |

TABLE II
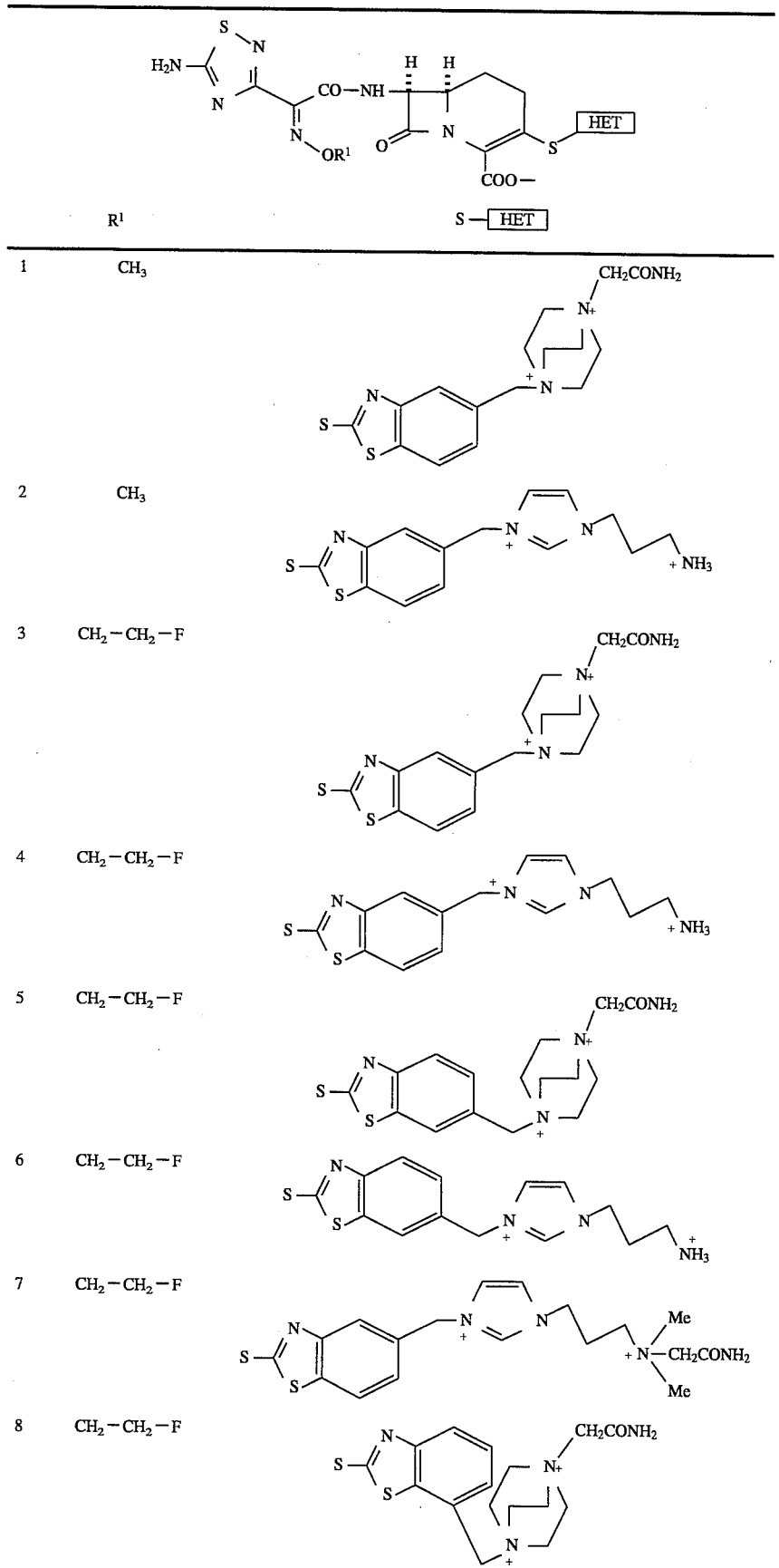

TABLE II-continued

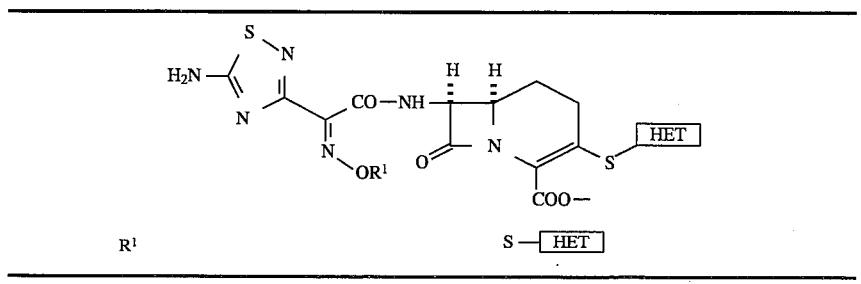

| | R¹ | S—HET |
|---|---|---|
| 9 | $CH_2-CH_2-F$ | (benzothiazole-thiol linked imidazolium propylammonium) |
| 10 | $CH_2-CH_2-F$ | (thiophene-dithiocarbonate linked DABCO with $CH_2CONH_2$) |
| 11 | $CH_2-CH_2-Br$ | (benzothiazole-thiol linked DABCO with $CH_2CONH_2$) |
| 12 | $CH_2-CH_2-Br$ | (benzothiazole-thiol linked imidazolium propylammonium) |
| 13 | $CH_2-CH_2-I$ | (benzothiazole-thiol linked DABCO with $CH_2CONH_2$) |
| 14 | $CH_2-CH_2-I$ | (benzothiazole-thiol linked imidazolium propylammonium) |
| 15 | $CH_2-CH_2-I$ | (benzothiazole-thiol linked DABCO with $CH_2CONH_2$) |

TABLE II-continued
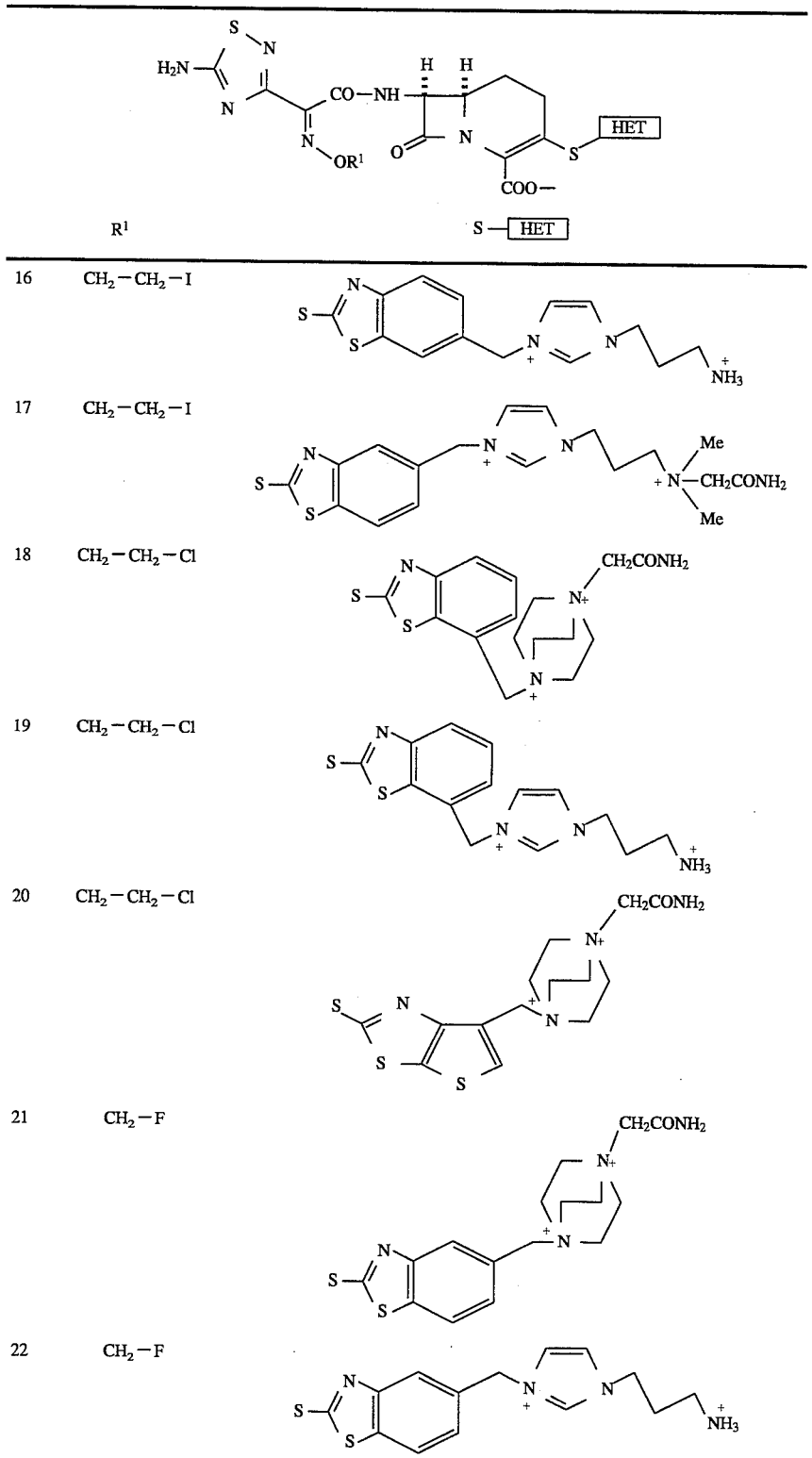
| | $R^1$ | S—HET |
|---|---|---|
| 16 | $CH_2-CH_2-I$ | |
| 17 | $CH_2-CH_2-I$ | |
| 18 | $CH_2-CH_2-Cl$ | |
| 19 | $CH_2-CH_2-Cl$ | |
| 20 | $CH_2-CH_2-Cl$ | |
| 21 | $CH_2-F$ | |
| 22 | $CH_2-F$ | |

TABLE II-continued
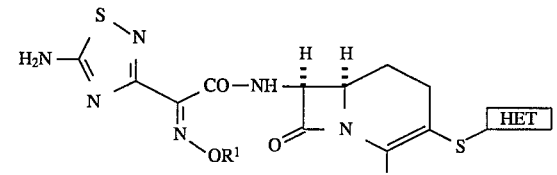
| | R¹ | S—[HET] |
|---|---|---|
| 23 | $CH_2-CF_3$ | 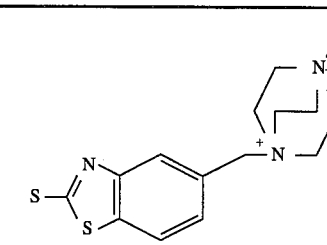 |
| 24 | $CH_2-CF_3$ | 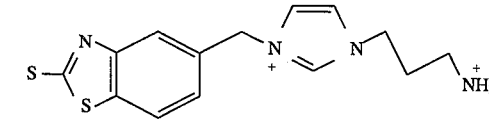 |
| 25 | $CH_2-CH_2-CH_3$ | 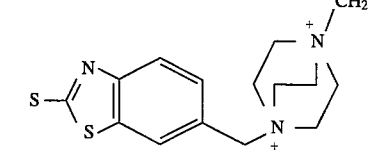 |
| 26 | $CH_2-CH_2-CH_3$ | 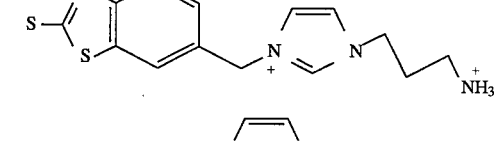 |
| 27 | $CH_2-CH=CCl_2$ | 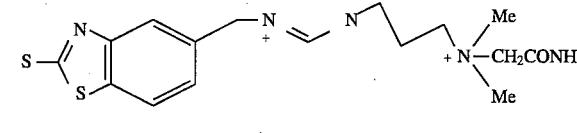 |
| 28 | $CH_2-CH=CCl_2$ | 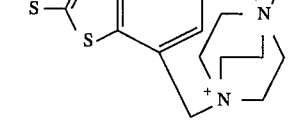 |
| 29 | $CH_2-CH_2-OH$ | 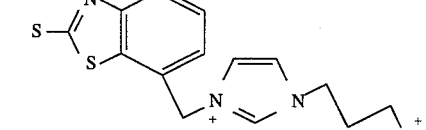 |
| 30 | $CH_2-CH_2-OH$ | 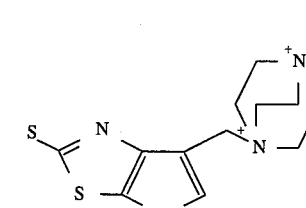 |

TABLE II-continued
| | R¹ | S—HET |
|---|---|---|
| 31 | CH₂—S—CH₃ | |
| 32 | CH₂—S—CH₃ | |
| 33 | CH₂—CH₂—CH₂—F | |
| 34 | CH₂—CH₂—CH₂—F | |
| 35 | CH₂—CH₂—CH₂—F | |
| 36 | CH₂—CH₂—CH₂—F | |
| 37 | CH₂—CH₂—CH₂—F | |
| 38 | CH₂—CH₂—CH₂—F | |
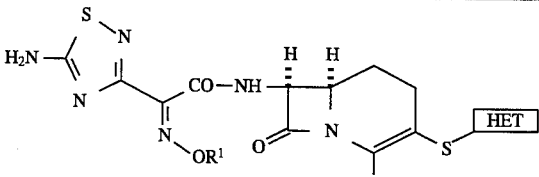

TABLE II-continued

| | $R^1$ | S—HET |
|---|---|---|
| 39 | $CH_2-CH_2-CH_2-F$ | (benzothiazole-thio linked to imidazolium-CH2, with N-propyl-NH3+) |
| 40 | $CH_2-CH_2-CH_2-F$ | (thieno-thiazole-thio linked via CH2 to DABCO with CH2CONH2) |
| 41 | $CH_2-CH(CH_3)_2$ | (benzothiazole-thio, aryl-N-DABCO with CH2CONH2) |
| 42 | $CH_2-CH(CH_3)_2$ | (benzothiazole-thio linked via CH2 to imidazolium-propyl-NH3+) |
| 43 | $CH(CH_3)_3$ | (benzothiazole-thio, aryl-N-DABCO with CH2CONH2) |
| 44 | $CH(CH_3)_3$ | (benzothiazole-thio linked via CH2 to imidazolium-propyl-NH3+) |
| 45 | $CH_2-C_6H_5$ | (benzothiazole-thio linked via CH2 to DABCO with CH2CONH2) |

TABLE II-continued

| | $R^1$ | S—HET |
|---|---|---|
| 46 | $CH_2C_6H_5$ | |
| 47 | $CH_2C_6H_5$ | |
| 48 | H | |
| 49 | H | |
| 50 | H | |
| 51 | cyclopentenyl | |
| 52 | cyclopentenyl | |

TABLE II-continued
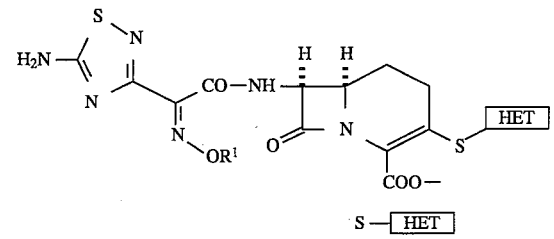
| | $R^1$ | S—HET |
|---|---|---|
| 53 |  | |
| 54 | | |
| 55 | H | |
| 56 | H | |
| 57 | H | |
| 58 | | |
| 59 | | |
| 60 | | |

TABLE II-continued
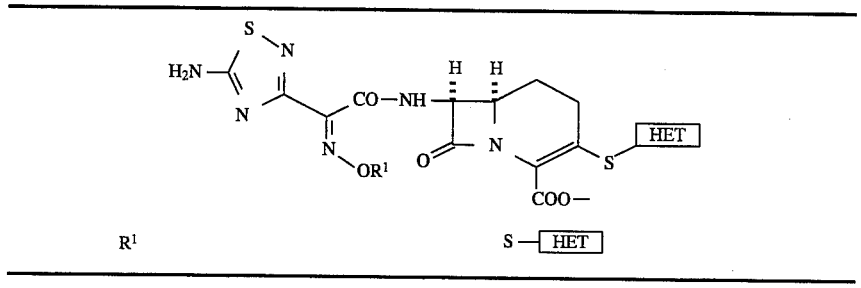
| | $R^1$ | S—HET |
|---|---|---|
| 61 | $CH_2-CH_2-F$ | |
| 62 | $CH_2-CH_2-F$ | |
| 63 | $CH_2-CH_2-F$ | |
| 64 | $CH_2-CH_2-F$ | |
| 65 | $CH_2-CH_2-F$ | |
| 66 | $CH_2-CH_2-F$ | |
| 67 | $CH_2-CH_2-F$ | |

TABLE II-continued
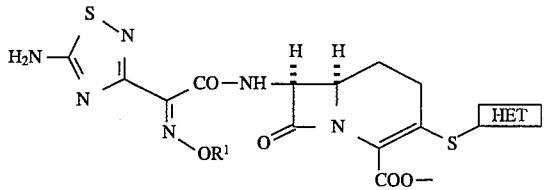
| | R¹ | S—HET |
|---|---|---|
| 68 | $CH_2-CH_2-F$ | 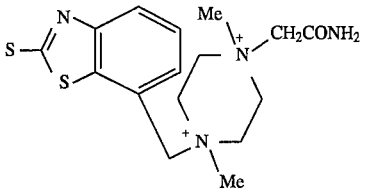 |
| 69 | $CH_2-CH_2-F$ | 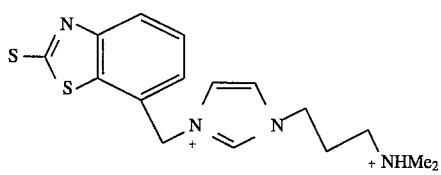 |
| 70 | $CH_2-CH_2-F$ | 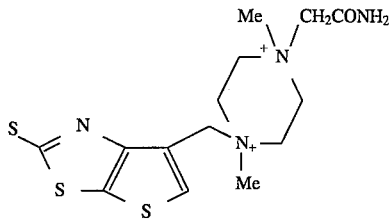 |
| 71 | $CH_2-CH_2-F$ | 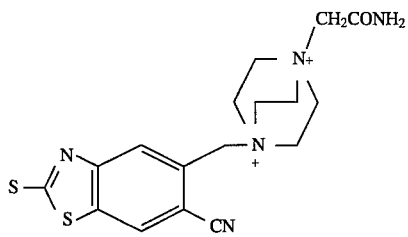 |
| 72 | $CH_2-CH_2-F$ | 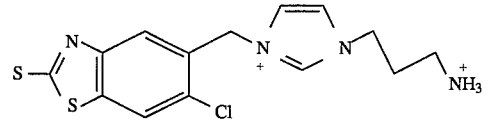 |
| 73 | $CH_2-CH_2-F$ | 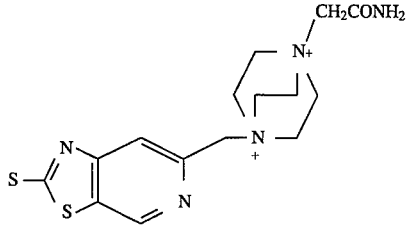 |
| 74 | $CH_2-CH_2-F$ | 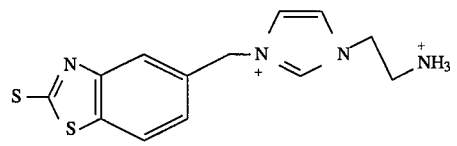 |

TABLE II-continued
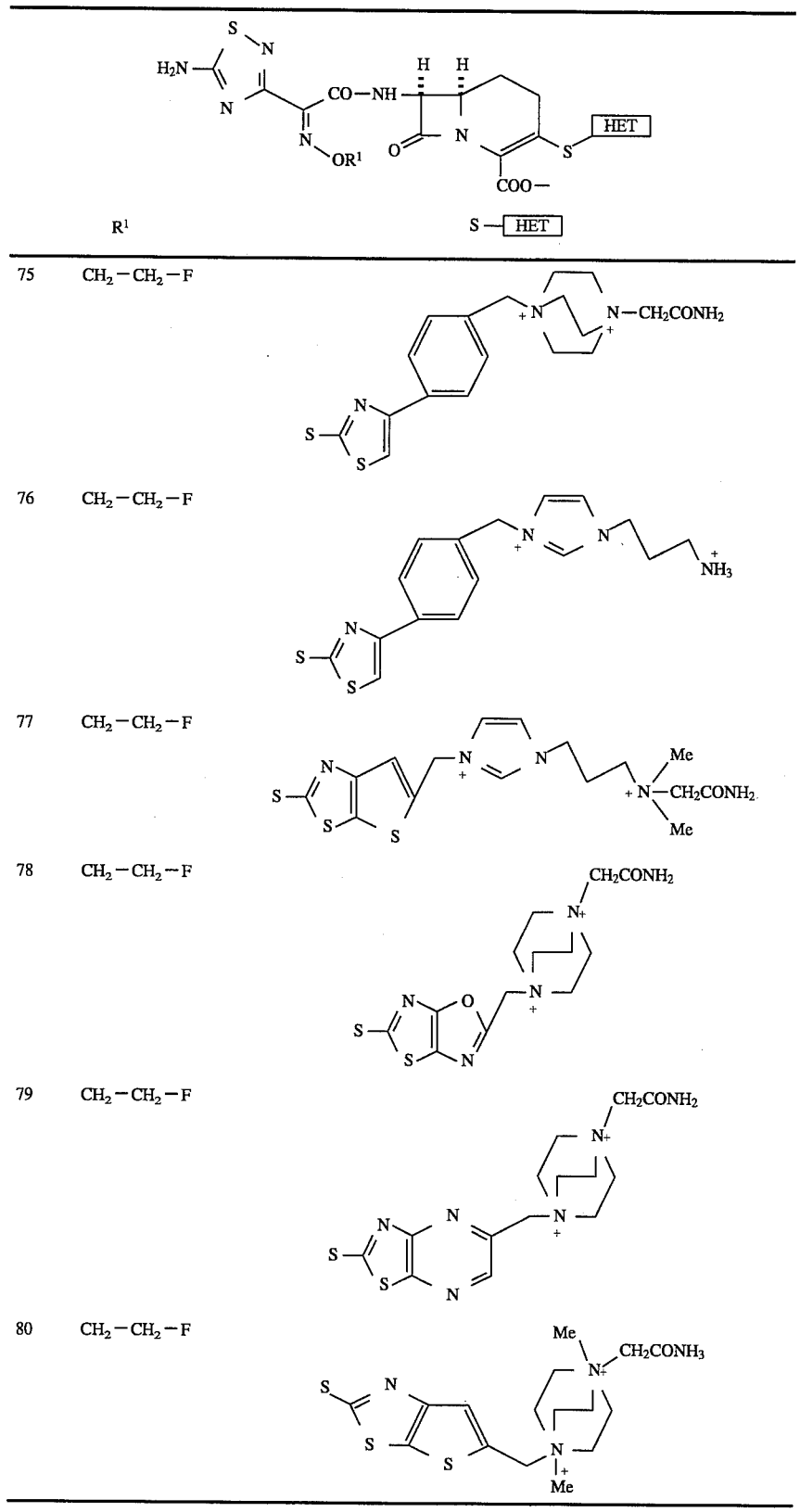

TABLE III
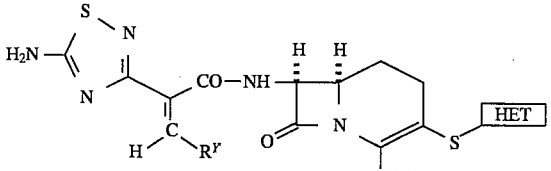
| | $R^r$ | S—[HET] |
|---|---|---|
| 1 | CH$_2$CH$_3$ | 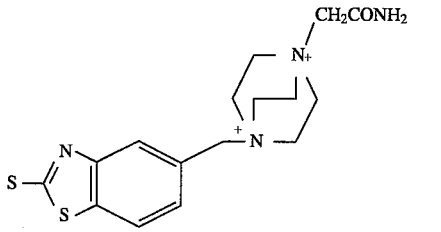 |
| 2 | CH$_2$CH$_3$ | 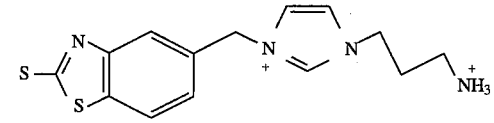 |
| 3 | CH$_2$C(CH$_3$)$_3$ | 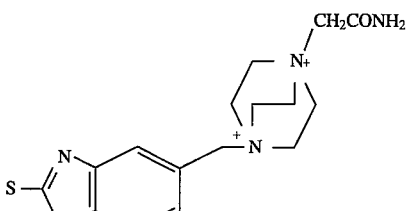 |
| 4 | CH$_2$C(CH$_3$)$_3$ | 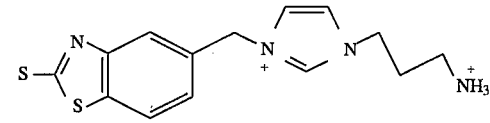 |
| 5 | H$_2$C—cyclopentyl | 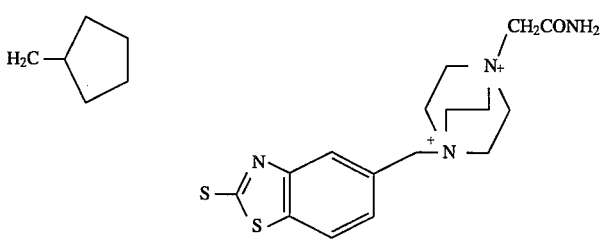 |
| 6 | H$_2$C—cyclopentyl | 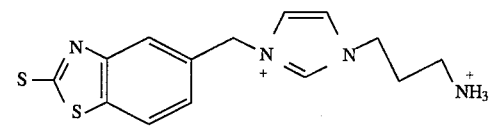 |
| 7 | cyclopentyl | 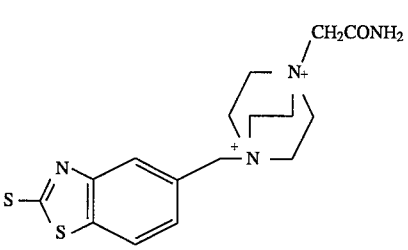 |

TABLE III-continued

| | $R^r$ | S—HET |
|---|---|---|
| 8 | cyclopentyl-CH | benzothiazole-imidazolium-propylammonium |
| 9 | cyclohexyl | benzothiazole-DABCO-CH$_2$CONH$_2$ |
| 10 | cyclohexyl | benzothiazole-imidazolium-propylammonium |
| 11 | CH$_2$CH$_3$ | benzothiazole-DABCO-CH$_2$CONH$_2$ |
| 12 | CH$_2$CH$_3$ | benzothiazole-imidazolium-propylammonium |
| 13 | CH$_2$C(CH$_3$)$_3$ | benzothiazole-DABCO-CH$_2$CONH$_2$ |
| 14 | CH$_2$C(CH$_3$)$_3$ | benzothiazole-imidazolium-propylammonium |

TABLE III-continued
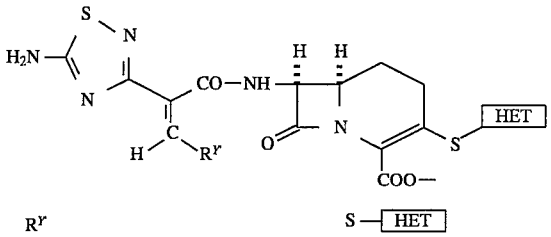
| | $R^r$ | S—HET |
|---|---|---|
| 15 | 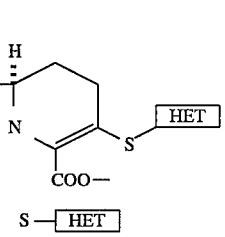 | 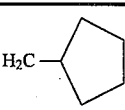 |
| 16 | 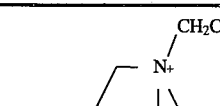 | 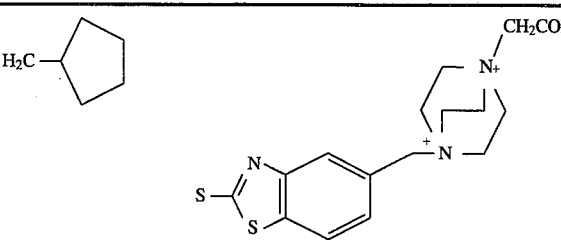 |
| 17 | 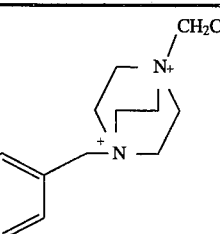 | 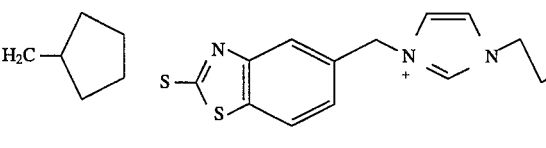 |
| 18 | 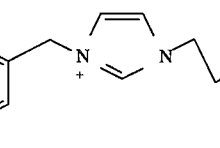 | 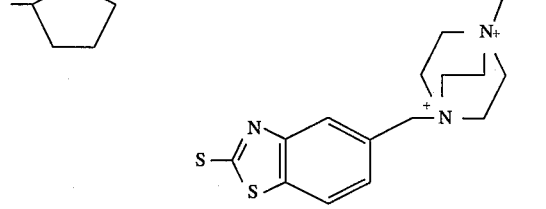 |
| 19 | 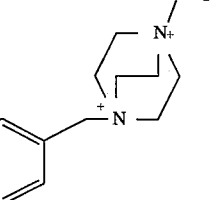 | 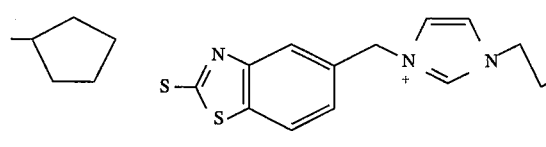 |
| 20 | 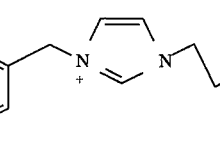 | 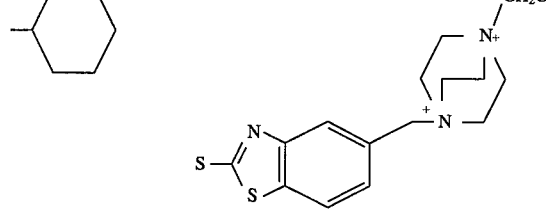 |

General Synthetic Scheme A
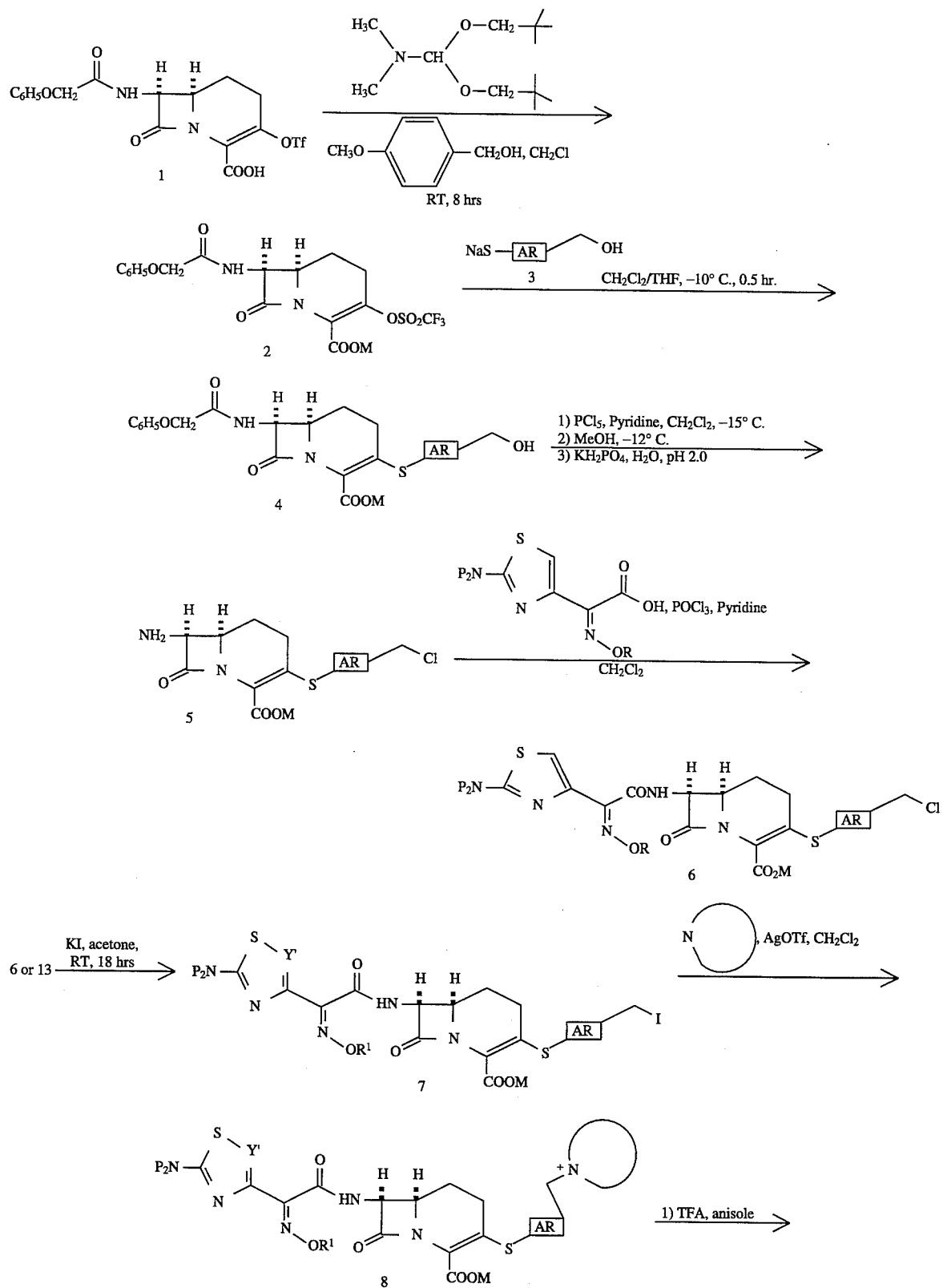

-continued
General Synthetic Scheme A
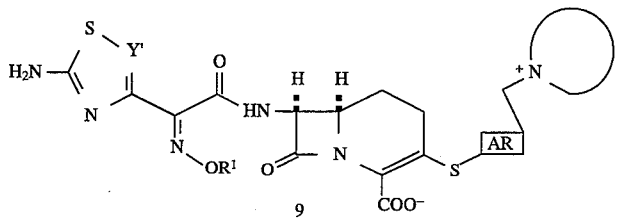
Synthetic Scheme B
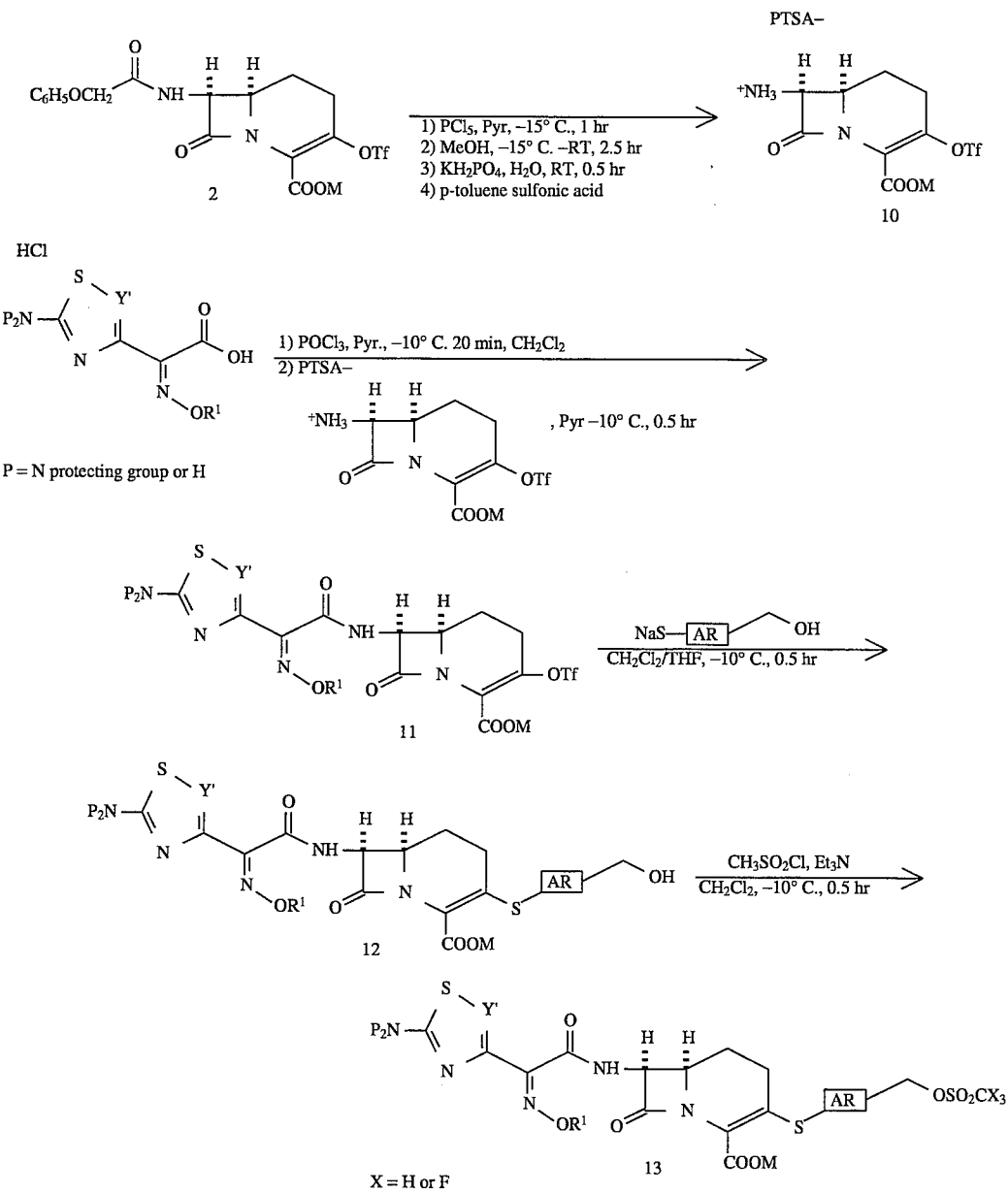
The synthesis of compounds of Formula I may be carded out as shown in reaction schemes A and B, With reference to the reaction schemes:

AR represents a heterocyclic moiety which is converted to the moiety

HET of formula I.

P represents an acid labile nitrogen protecting group or hydrogen.

When $R^1$ in formula I is hydrogen $R^1$ in the scheme can be an acid labile hydroxy protecting group,

represents a tertiary aromatic, heteroaromatic or alaphatic amine which by reaction with the cephem alkylating group results in a quaternary group of the present invention.

The starting material for the synthesis is 3-trifluoromethane sulfonyloxy-1-carba-1-dethiaceph-3-em-4-carboxylic acid 1. J. K. Cook, et al. *J. Med, Chem.* 1989, 32, 2442–2450. Reaction of 2 with the sodium salt of a suitable heteroaryl thiol, prepared by the reaction of a reagent such as sodium hydride or sodium hexamethyldisilazide with the thiol, in a non-polar solvent or solvent mixture at −20° C. to room temperature, gives the desired addition product 4, as a mixture of the $\Delta^2$ and $\Delta^3$ isomers. The desired $\Delta^3$ isomer is separated by fractional crystallization or by chromatography.

The heterocyclic thiol used herein is usually not the same as the final substituent HET but bears a group that eventually can be converted to it.

The heterocyclic thiols used in the synthesis of the present invention are, in many cases known in the literature and many are commercially available. In those cases where the required heterocyclic thiol is neither commercially available or known in the literature, they can be easily prepared by one skilled in the an by modification of literature syntheses towards the desired heterocyclic thiol.

The phenoxyacetyl side chain at the 7-position is removed by procedures well known in the an, such as reaction with phosphorous pentachloride in the presence of a base such as pyridine at −20° to −10° C. for 1 hour, followed by reaction of the intermediate with methanol at −15° to −10° C. for 1.5 hours. This is followed by treatment with a phosphate buffer at pH 2 for 0.5 hour at room temperature, to give the product 5, isolated as its p-toluensulfonic acid salt. In the case where the heteroaryl group of 4 has a hydroxymethyl group attached to it, the above reaction results in simultaneous conversion of the hydroxymethyl group to the chloromethyl group in 5. Alternatively the hydroxymethyl group in 4 can be convened to the chloromethyl group by reaction with a suitable chlorinating agent such as thionyl chloride and pyridine or phosphorous oxychloride and pyridine before subjecting the compound to the side chain removing reaction sequence described above.

The free amino group of 5 can be acylated with the desired acid chloride, prepared from the acid by reaction of the acid in-situ with a number of reagents known in the an such as phosphorous oxychloride and pyridine or oxalyl chloride and dimethylformamide. Alternatively the acid may be reacted directly with the amine in the presence of a coupling reagent such as a carbodiimide to give the desired amide 6. The amino function in the acid chloride is usually protected with an acid labile protecting group.

In an alternate route shown in scheme B, the triflate 2 is treated with the side chain removing sequence to give the triflate 10 which is then reacted with the desired acid or its acid chloride to give the triflate 11 which has the desired 7-side chain in place. Reaction of 11 with the sodium salt of the thiol then gives a compound such as 12, which bears a hydroxyalkyl substituent on the heteroaryl substituent. The hydroxy group is converted to a leaving group such as a methanesulfonate or trifluoromethanesulfonate by reaction with methane sulfonyl chloride or trifluoromethane sulfonic anhydride in the presence of a base such as triethylamine or pyridine or 2,6-collidine to give 13.

Reaction of compound 6 or 13 with potassium iodide in acetone from about −10° C. to about room temperature gives the iodo derivative 7.

The introduction of the quaternary substituent is carried out by treatment of the iodo compound 7 with the tertiary amine corresponding to the quaternary substituent. The alkylation of the tertiary amine by the iodo compound 7 is carried out by reaching the two in an inert polar solvent such as acetonitrile, DMF, N-methylpyrrolidinone, etc. in the presence of the silver salt of a non-nucleophillic acid such as silver trifluoromethanesulfonate, silver trifluoroborate and the like to give compound 8. In certain cases when the leaving group is trifluoromethanesulfonate of 13, excess tertiary amine quaternizing agent can be used as both base and quaternizing agent.

The carboxylic acid protecting group M is then removed by treatment with a strong organic acid such as trifluoroacetic acid, in the presence of a carbonium ion acceptor such as anisole to give the free acid. The procedure also results in the concomitant removal of other acid labile protecting groups in the molecule resulting in the final desired product of the invention 9.

The compound of the invention may be used in a variety of pharmaceutical preparations. Compositions for injection, the preferred route of delivery, may be prepared in unit dosage form in ampoules or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the active ingredient may be in the form of a powder, which can be reconstituted with a suitable carder such as sterile water, normal saline and the like at the time of administration. The powder can be in lyophilized or non-lyophillized form.

Oral compositions are typically in the form of tablets, capsules, solutions or suspensions. Such compositions may likewise be packaged in unit dose or multidose containers. In these oral compositions, the pharmaceutically acceptable carriers may be comprised of diluents, tableting and granulating aids, lubricants, disintegrants, buffers, sweeteners, preservatives and the like.

The dosage to be administered depends to a large extent upon the condition and size of the subject being treated as well as the route and frequency of administration. The parenteral route (by injection) is preferred for generalized infections. Such matters, however, are typically left to the discretion of the clinician according to principles of treatment well known in the antibacterial arts.

The compositions for human delivery per unit dosage, whether liquid or solid, may contain from about 0.01% to about 99% of active material, the preferred range being from about 10–60%. The composition will generally contain from about 15 mg to about 2000 mg of the active ingredient; however, in general, it is preferable to employ a dosage amount in the range of from about 250 mg to 1000 mg. In parenteral administration, the unit dosage is usually the compound I in a sterile water or saline solution or in the form of a soluble powder intended for solution.

The preferred method of administration of the compound of formula I is parenterally by intravenous (i.v.) infusion. Alternatively, the compound may be administered intramuscularly (i.m.).

For adults, a dose of about 5 to about 50 mg of the formula I antibacterial compound per kg of body weight is administered from 1 to 6 times per day. The preferred dosage ranges from about 250 mg to 1000 mg of the compound given one to four times per day.

More specifically, for mild infections a dose of 250 mg two to four times daily is preferred. For moderate infections against highly susceptible gram positive organisms a dose of 500 mg b.i.d. to q.i.d. is preferred. For severe, life-threatening infections against organisms at the upper limits of sensitivity to the antibiotic, a dose of about 1000–2000 mg two to six times daily is preferred.

For children, a dose of 5–25 mg/kg of body weight given 1 to 4 times per day is preferred; a dose of 10 mg/kg b.i.d., t.i.d. or q.i.d. is recommended.

The compounds of the present invention are active against various gram-positive and to a lesser extent gram-negative bacteria, and accordingly find utility in human and veterinary medicine. The compounds are particularly useful as anti-MRSA/MRCNS compounds.

The invention is further described in connection with the following non-limiting examples.

Preparative Example 1

2-THIO-4-((TRIMETHYL)SILYLOXYMETHYL)THIAZOLO[5,4-B]PYRIDINE

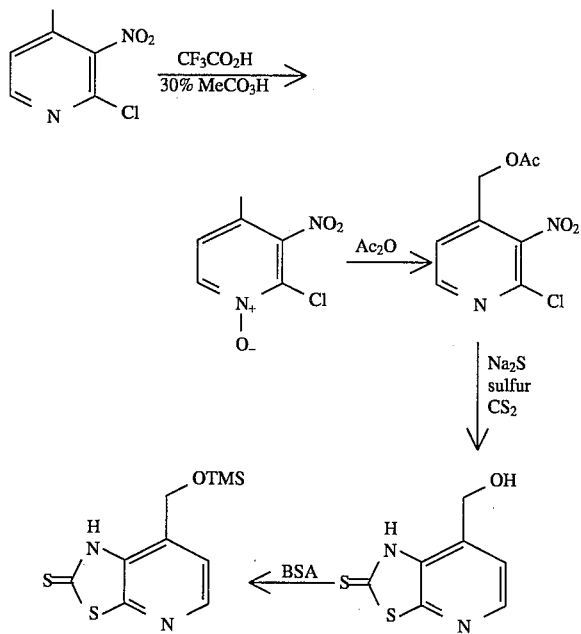

Step 1
2-Chloro-3-nitro-4-picoline-N-oxide

2-Chloro-3-nitro-4-picoline (7g, 0.04 mol) was added to an ice cooled mixture of trifluoroacetic acid (25 mL) and 30% peracetic acid in acetic acid (15 mL). The mixture was allowed to warm to room temperature over 30 minutes and was heated in a 60° C. oil bath for 5 hrs. The mixture was partitioned between methylene chloride (100 mL) and water (100 mL). The pH was adjusted to 8 with 2.5N sodium hydroxide and the aqueous layer was extracted with more methylene chloride (2×100 mL). The combined methylene chloride layers were dried with magnesium sulfate, filtered and evaporated to give 7.5g of a 4:1 mixture of 2-Chloro-3-nitro-4-picoline-N-oxide (79%) and 2-Chloro-3-nitro-4-picoline, as determined by the integration of the NMR resonances. The two compounds could be separated by silica chromatography, but was used as is in the next reaction.

$^1$NMR (CDCl$_3$, 300 MHz) δ2.34(s, Me), 7.16 (d, H5), 8.31 (d, H6).

Step 2
2-Chloro-3-nitro-4-acetoxymethylpyridine

A 4:1 mixture of 2-Chloro-3-nitro4-picoline-N-oxide and 2-Chloro-3-nitro4-picoline (7.2g, 0.031 mol, based on the N-oxide) was dissolved in acetic anhydride (20 mL) and the solution was heated in a 80° C. oil bath for 70 minutes. The solvents were removed under vacuum and the dark residue was partitioned between methylene chloride (100 mL) and saturated aqueous potassium carbonate (200 mL). The aqueous layer was re-extracted with more methylene chloride (1×50 mL) and the combined methylene chloride layers were dried with magnesium sulfate, filtered and evaporated under vacuum. The crude solid was dissolved in methylene chloride (20 mL) and was loaded onto a silica gel column (E. Merck 60, 230–400 mesh, 4×36 cm). The column was eluted with methylene chloride collecting 25 mL fractions. Fractions 22–48 were combined and evaporated to give substantially pure 2-chloro-3-nitro-4-acetoxymethylpyridine (1.75g) as a white solid.

$^1$H NMR (CDCl$_3$, 300 MHz) δ2.11 (s, Ac), 5.14 (s, CH$_2$OAc), 7.41 (d, H5), 8.51 (d, H6).

Step 3
2-thio-4-hydroxymethylthiazolo[5,4-b]pyridine

A suspension of sulfur (0.5g, 15.6 mmol) and sodium sulfide nonahydrate (1.84g, 7.66 mmol) in water (2 mL) was heated in a 50° C. oil bath for 15 minutes. The amber colored solution was cooled to room temperature, 2-chloro-3-nitro-4-acetoxymethylpyridine (0.5g, 2.17 mmol) and carbon disulfide (0.5 mL, 8.3 mmol) were added and the mixture was heated in a 70° C oil bath for 3.5 hours under a nitrogen atmosphere. After cooling to room temperature, the suspension was filtered and the recovered sulfur was washed with water (5 mL). The filtrate was acidified with acetic acid and 5% methanol/methylene chloride (20 mL) was added to the gummy precipitate. The aqueous layer was re-extracted with 5% methanol/methylene chloride (3×10 mL) and the combined extracts were dried with magnesium sulfate, filtered and evaporated to a solid (0.58g). The crude material was first purified on a silica column (E. Merck 60, 230–400 mesh, 4×24 cm) using 5% methanol/methylene chloride as the developing solvent and collecting 8 mL fractions. Fractions 5-10 were combined and evaporated to a dark solid (220mg). The solid was placed on preparative silica plates (Analtech, 4×500 micron, 5% methanol/methylene chloride as developing solvent), the product was removed, eluted with 20% methanol/methylene chloride and evaporated to provide the title compound as a light orange solid (0.15g).

$^1$H NMR (DMSO-d6, 300 MHz) δ4.71 (d, CH$_2$OH), 5.59 (t, CH$_2$OH), 7.45 (d, H5), 8.38 (d, H6).

MS (M+1) 199

Step 4
2-thio-4-((trimethyl)silyloxymethyl)thiazolo[5,4-b]pyridine

A solution of 2-thio-4-hydroxymethylthiazolo[5,4-b]pyridine (45 mg, 0.227 mmol) was dissolved in bis(trimethylsilyl) acetamide (0.5 mL) and was stirred at room temperature for 20 minutes under nitrogen. The solution was evaporated under vacuum and the residue was applied to a flash silica gel column (E. Merck 60, 230–400 mesh, 2.5×10 cm). The column was eluted with 1:1 hexane/diethylether and 3 mL fractions were collected. Fractions 5–13 were combined and evaporated to give the title compound as a white solid (55 mg).

$^1$H NMR (CDCl$_3$, 300 MHz) $\delta$0.25 (s, Si(TMS)$_3$), 4.94 (s, CH$_2$O), 6.98 (d, H5), 8.31 (d, H6).

Preparative Example 2

2-THIO-6-(TRIMETHYL)SILYLOXYMETHYL)THIAZOLO[5,4-B]PYRIDINE

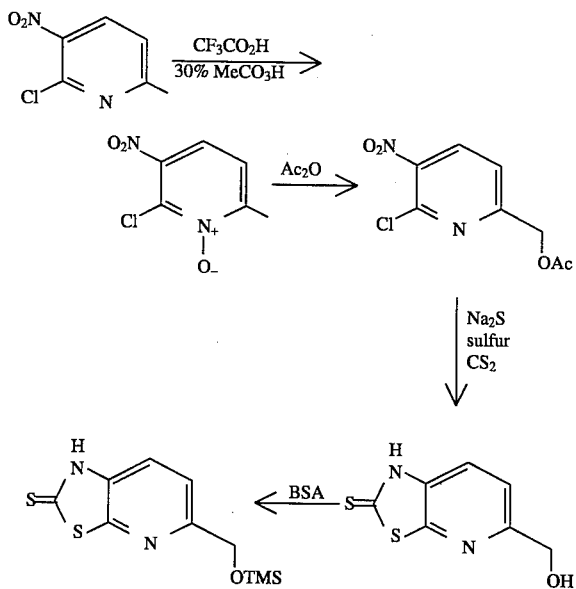

Step 1
2-Chloro-3-nitro-6-picoline-N-oxide

2-Chloro-3-nitro-6-picoline (2g, 11.6 mmol) was added to an ice cooled mixture of trifluoroacetic acid (6 mL) and 30% peracetic acid in acetic acid (6 mL). The mixture was allowed to warm to room temperature over 30 minutes and was heated in a 60° C. oil bath for 5 hours. The mixture was partitioned between methylene chloride (100 mL) and water (50 mL). The pH was adjusted to 8 with 2.5N sodium hydroxide and the aqueous layer was extracted with more methylene chloride (2×50 mL). The combined methylene chloride layers were dried with magnesium sulfate, filtered and evaporated to give the title compound as a white solid (1.6 g).

$^1$H NMR (CDCl$_3$, 300 MHz) $\delta$2.62(s, Me), 7.35 (d, ArH), 7.66 (d, ArH).

Step 2
2-Chloro-3-nitro-6-acetoxynethylpyridine

2-Chloro-3-nitro-6-picoline-N-oxide (1.6 g, 8.5 mmol) was dissolved in acetic anhydride (5 mL) and the solution was heated at a 60° C. oil bath for 3 hours. The solvents were removed under vacuum and the dark residue was partitioned between methylene chloride (30 mL) and saturated aqueous potassium carbonate (100 mL). The aqueous layer was re-extracted with more methylene chloride (2×40 mL) and the combined methylene chloride layers were dried with magnesium sulfate, filtered and evaporated under vacuum. The crude solid was dissolved in methylene chloride (5 mL) and was loaded onto a silica gel column (E. Merck 60, 230–400 mesh, 2.5×24 cm). The column was eluted with methylene chloride collecting 8 mL fractions. Fractions 11–26 were combined and evaporated to give the title compound (0.42 g) as a white solid.

$^1$H NMR (CDCl$_3$, 300 MHz) $\delta$2.19 (s, Ac), 5.24 (s, CH$_2$OAc), 7.45 (d, H5), 8.23 (d, H$^4$).

Step 3
2-thio-6-hydroxymethylthiazolo[5,4-b]pyridine

A suspension of sulfur (0.5 g, 15.6 mmol) and sodium sulfide nonahydrate (2.0 g, 8.3 mmol) in water (3 mL) was heated in a 50° C. oil bath for 15 minutes. The amber colored solution was cooled to room temperature, 2-chloro-3-nitro-6-acetoxymethylpyridine (0.4 g, 1.73 mmol) and carbon disulfide (1 mL, 16.7 mmol) were added and the mixture was heated in a 60° C. oil bath for 18 hours under a nitrogen atmosphere. After cooling to room temperature, the suspension was filtered and the recovered sulfur was washed with water (5 mL). The flitrate was acidified with 2N hydrochloric acid to pH 3 and 5% methanol/methylene chloride (20 mL) was added to the gummy precipitate. The aqueous layer was re-extracted with 5% methanol/methylene chloride (3×10 mL) and the combined extracts were dried with magnesium sulfate and evaporated to a brown solid (0.58 g). The crude solid was purified on a silica column (E.Merck 60, 230–400 mesh, 2.5×30 cm) using 5% methanol/methylene chloride as the developing solvent and collecting 8 mL fractions. Fractions 26–46 were combined and evaporated to give the title compound as a orange solid (240 mg).

$^1$H NMR (DMSO-d6, 300 MHz) $\delta$4.61 (s, CH$_2$OH), 7.41 (d, ArH), 8.11 (d, ArH).
MS (M+1) 199

Step 4
2-thio-6-((trimethyl)silyloxymethyl)thiazolo[5,4-b]pyridine

A solution of 2-thio-6-hydroxymethylthiazolo[5,4-b] pyridine (230 mg, 1.16 mmol) was dissolved in a mixture of tetrahydrofuran (2 mL) and bis(trimethylsilyl) acetamide (1.0 mL) and was stirred at room temperature for 20 minutes under nitrogen. The solution was evaporated under vacuum and the residue was applied to a flash silica gel column (E. Merck 60, 230–400 mesh, 2.5×5 cm). The column was eluted with methylene chloride (60 mL), the eluent was evaporated and freeze-dried from benzene to give the title compound as a white solid (200 mg).

$^1$H NMR (DMSO-d6, 300 MHz) $\delta$0.05 (s, Si(TMS)$_3$), 4.56 (s, CH$_2$O), 7.48 (d, ArH), 7.63 (d, ArH).

Preparative Example 3

2-THIO-5-((TRIMETHYL)SILYLOXYMETHYL)THIAZOLO[5,4-B]PYRIDINE

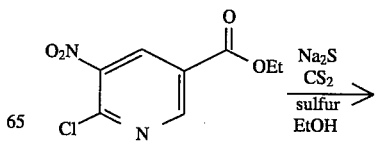

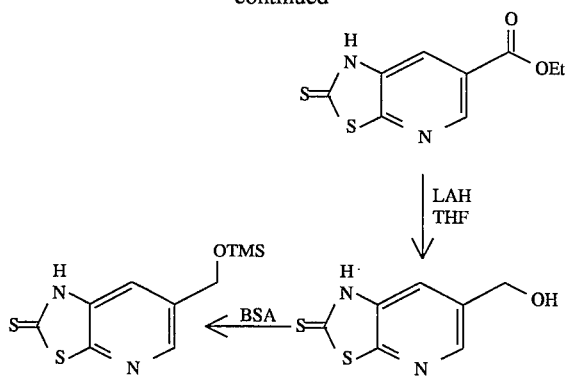

Step 1
2-thio-5-(ethoxycarbonyl)thiazolo[5,4-b]pyridine

A suspension of sodium sulfide nonahydrate (1.5 g, 6.25 mmol) and sulfur (0.5 g, 15.6 mmol) in ethanol (20 mL) were heated in a 50° C. oil bath for 10 minutes to give an amber colored solution. After cooling to room temperature, ethyl 2-chloro-3-nitronicotinate (0.58 g, 2.5 mmol) and carbon disulfide (2 mL) were added and the mixture was heated in a 80° C. oil bath for 20 hours. The solvents were evaporated under vacuum and the residue was partitioned between methylene chloride (30 mL) and water (5 mL). The pH was adjusted to 4 with acetic acid and the aqueous layer was re-extracted with 5% methanol/methylene chloride (2×20 mL). The combined extracts were dried with magnesium sulfate, filtered and evaporated. Concentrated ammonium hydroxide was added and the precipitated sulfur was filtered and the filtrate was evaporated. The residue was placed on a silica gel column (E. Merck 60, 230–400 mesh, 2.5×30cm), the column was eluted with 5% methanol/methylene chloride and 8 mL fractions were collected. Fractions 20–28 were combined and evaporated to give an impure light yellow solid (0.5 g). The collected solid was dissolved in hot ethanol (3 mL) and after cooling to room temperature the precipitate was filtered, washed with ethanol (5 mL) and provided the title compound as a white crystalline solid (0.265 g).

$^1$H NMR (CDCl$_3$, 300 MHz) $\delta$1.43 (t, CH$_2$CH$_3$), 4.45 (q, CH$_2$ CH$_3$), 8.02 (d, H4), 9.02 (d, H6).

Step 2
2-thio-5-(hydroxymethyl)thiazolo[5.4-b]pyridine 2-thio-5-(ethoxycarbonyl)thiazolo[5,4-b]pyridine (120 mg, 0.5 mmol) was dissolved in tetrahydofuran (3 mL) and was treated with lithium aluminum hydride (1 mL, 1 mmol, 1M solution in tetrahydrofuran) at room temperature under nitrogen. After 30 minutes, water (0.5 mL) was added cautiously and the granular precipitate was filtered through solka-floc. The filtrate was evaporated under vacuum and provided the title compound as a solid (120 mg).

$^1$H NMR (DMSO-d$_6$, 300 MHz) $\delta$4.58 (s, CH$_2$OH), 7.55 (d, H4), 8.32 (d, H6).

MS (M+1) 199

Step 3
2-thio-5-((trimethyl)silyloxymethyl)thiazolo[5,4-b]pyridine

A solution of 2-thio-5-hydroxymethylthiazolo[5,4-b]pyridine (120 mg, 0.61 mmol) was dissolved in a mixture of tetrahydrofuran (2 mL) and bis(trimethylsilyl) acetamide (0.5 mL) and was stirred at room temperature for 20 minutes under nitrogen. The solution was evaporated under vacuum and the residue was applied to a flash silica gel column (E. Merck 60, 230–400 mesh, 2.5×5 cm). The column was eluted with methylene chloride (50 mL) and evaporated to give a white solid. The solid was triturated with hexanes, was filtered and provided the title compound as a white solid (64 mg).

$^1$H NMR (CDCl$_3$, 300 MHz) $\delta$0.19 (s, Si(TMS)$_3$), 4.77 (s, CH$_2$O), 7.53 (s, H4), 8.36 (s, H6).

Preparative Example 4

6-HYDROMETHYL-2-MERCAPTOBENZOTHIAZOLE

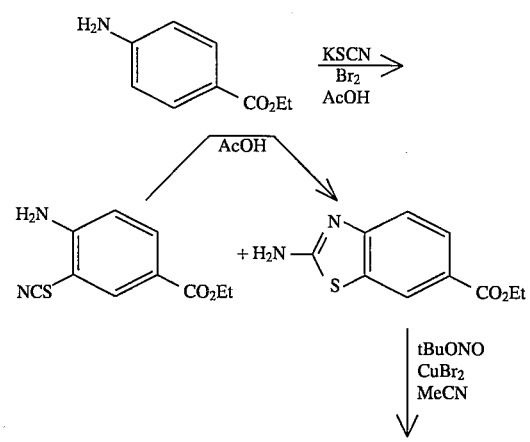

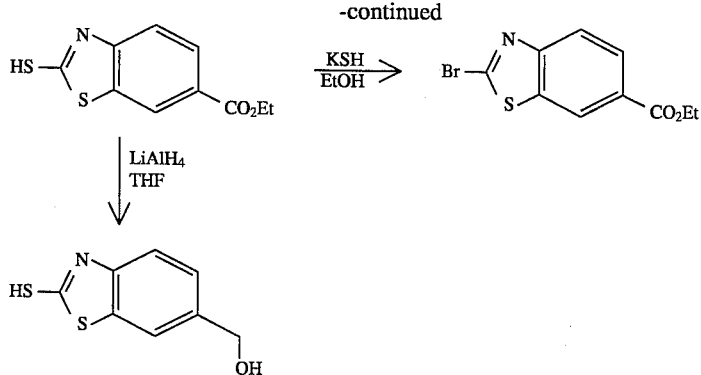

Step 1
2-Amino-6-ethoxycarbonylbenzothiazole

A solution of ethyl 4-aminobenzoate (8.26 g, 0.05 mol) in acetic acid (100 mL) was treated with potassium thiocyanate (14.58 g, 0.15 mol) and stirred 10 minutes at room temperature to dissolve the salt. The resulting solution was cooled in an ice bath and stirred while bromine (2.6 mL, 0.05 mol) was added dropwise over 15 minutes. The cooling bath was removed and the mixture was stirred at room temperature for 2.25 hours. The mixture was stored at 5° C. for 5 hours, then filtered to remove the yellow precipitate. The filter cake was washed with diethyl ether (2×50 mL) and water (2×100 mL) and dried under vacuum to give 2-amino-6-ethoxycarbonylbenzothiazole (2.54 g) as a yellow solid.

The acetic acid filtrate and ether washings were combined and evaporated under vacuum to an amber gum. The water washings from the yellow solid were added and the mixture was neutralized with solid sodium bicarbonate. The resulting precipitate was collected, washed with water and dried under vacuum to a pale tan solid (8.74 g). Proton NMR analysis of this material revealed a 65:35 mixture of ethyl 4-amino-3-thiocyanatobenzoate to 2-amino-6-ethoxycarbonylbenzothiazole. The mixture was dissolved in acetic acid (100 mL) and stirred at room temperature for 42 hours. A fine precipitate formed. The mixture was filtered and the cake washed with diethyl ether and dried under vacuum to give additional 2-amino-6-ethoxycarbonylbenzothiazole (2.28 g) as a cream colored powder.

$^1$H NMR (DMSO-d$_6$, 500 MHz) δ1.30 (t, CH$_3$), 4.28 (q, CH$_2$), 7.38 (d, H-4), 7.82 (dd, H-5), 8.07 (br s, NH$_2$), and 8.29 (d, H-7).

$^{13}$C NMR (DMSO-d$_6$, 125.7 MHz) δ14.2, 60.4, 116.8, 122.3, 122.7, 127.2, 130.5, 155.5, 165.5, and 169.8.

Step 2
2-Bromo-6-ethoxycarbonylbenzothiazole

A mixture of copper(II) bromide (2.70 g, 12.09 mmol) and anhydrous acetonitrile (50 mL) was purged with nitrogen, cooled in an ice bath, treated with tert-butyl nitrite (1.8 mL, 15.13 mmol), stirred 10 minutes at 0-5° C., and then treated with solid 2-amino-6 ethoxycarbonylbenzothiazole (2.24 g, 10.08 mmol). The cooling bath was removed and the mixture was stirred at room temperature for 2 hours. The mixture was diluted with water (300 mL) and extracted with diethyl ether (2×100 mL). The extracts were filtered to remove copper salts, then washed with water (100 mL) and brine (100 mL), dried over sodium sulfate, filtered and evaporated under vacuum to provide crude 2-bromo-6-ethoxycarbonylbenzothiazole (1.90 g) as an orange-tan solid.

$^1$H NMR (CDCl$_3$, 500 MHz) δ1.42 (t, CH$_3$), 4.42 (q, CH$_2$), 8.02 (d, H-4), 8.15 (dd, H-5), and 8.53 (d, H-7).

$^{13}$C NMR (CDCl$_3$, 125.7 MHz) δ14.3, 61.5, 122.5, 122.9, 127.8, 137.2, 142.3, 155.0, and 165.7.

Step 3
6-Ethoxycarbonyl-2-mercaptobenzothiazole

The crude 2-bromo-6-ethoxycarbonylbenzothiazole (1.90 g, 6.64 mmol) from Step 2 was suspended in absolute ethanol (35 mL) and treated with potassium hydrogen sulfide (0.96 g, 13.3 mmol). The mixture was placed under a nitrogen atmosphere, stirred, and heated in an oil bath at 80° C. The benzothiazole starring material gradually went into solution. After hearing for 30 minutes, the mixture was cooled in an ice bath, treated with 1N hydrochloric acid (13.5 mL), and evaporated under vacuum. The residue was partitioned between ethyl acetate (100 mL) and water (100 mL) and the aqueous phase extracted with more ethyl acetate (50 mL). The combined ethyl acetate solution was washed with brine (50 mL), dried over sodium sulfate, filtered and evaporated under vacuum to a yellow-tan solid (1.56 g). This material was triturated with diethyl ether and dried under vacuum to provide 6-ethoxycarbonyl-2-mercaptobenzothiazole (1.14 g) as a pale tan powder.

$^1$H NMR (DMSO-d$_6$, 500 MHz) δ1.31 (t, CH$_3$), 3.33 (br s, SH), 4.30(q, CH$_2$), 7.35 (d, H-4), 7.94 (d, H-5), and 8.29 (s, H-7).

$^{13}$C NMR (DMSO-d$_6$, 125.7 MHz) δ14.1, 60.9, 112.1, 123.2, 125.5, 128.4, 129.7, 144.6, 165.0, and 191.8.

Step 4
6-Hydroxymethyl-2-mercaptobenzothiazole

A solution of 6-ethoxycarbonyl-2-mercaptobenzothiazole (1.14 g, 4.64 mmol) in anhydrous tetrahydrofuran (14 mL) was heated to reflux under a nitrogen atmosphere and stirred while 1M lithium aluminum hydride in tetrahydrofuran (4.7 mL) was added dropwise. The resulting mixture was stirred and heated at reflux for one hour, then cooled in an ice bath and cautiously treated with 2N hydrochloric acid. The mixture was diluted with water (20 mL) and extracted with ethyl acetate ( 3×25 mL). The combined extracts were washed with brine (25 mL), dried over sodium sulfate, filtered and evaporated under vacuum to provide 6-hydroxymethyl-2-mercaptobenzothiazole (0.89 g) as a pale yellow solid.

$^1$H NMR (DMSO-d$_6$, 500 MHz) δ3.33 (br s, SH), 4.51 (s, C$\underline{H}_2$OH), 5.28 (br s, CH$_2$O$\underline{H}$), 7.25 (d, H-4), 7.32 (dd, H-5), and 7.60 (d, H-7).

$^{13}$C NMR (DMSO-d$_6$, 125.7 MHz) δ62.5, 112.0, 119.4, 125.7, 129.3, 139.0, 140.1, and 189.6.

Preparative Example 5

7-HYDROXYMETHYL-2-MERCAPTOBENZOTHIAZOLE

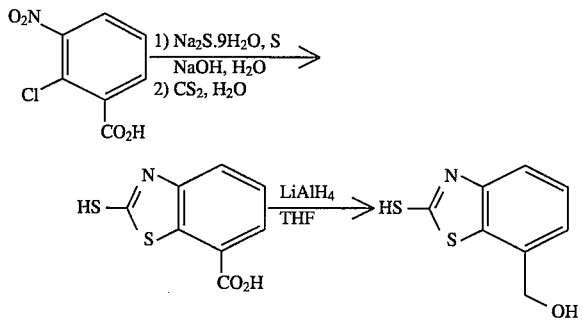

Step 1

7-Carboxy-2-mercaptobenzothiazole

2-Chloro-3-nitrobenzoic acid (8.06 g, 0.04 mol) in 1N sodium hydroxide (50 mL) was added to a polysulfide solution made from sodium sulfide nonahydrate (28.82 g, 0.12 mol) and sulfur (9.60 g, 0.30 mol) in water (30 mL). The resulting mixture was stirred and heated at reflux for 5.5 hours. The reaction mixture was cooled to 45° C., treated with carbon disulfide (4.81 mL, 0.08 mol), and stirred at 45° C. for 20 hours. The mixture was cooled in an ice bath and neutralized by slowly adding acetic acid (7 g). The solid precipitate was collected, washed with ice-cold water, suspended in saturated sodium carbonate solution (100 mL), and filtered to remove insolubles. The filtrate was acidified with acetic acid (33 g) and filtered to collect the insoluble material. The filter cake was dried under vacuum to afford crude 7-carboxy-2-mercaptobenzothiazole (0.70 g) as a brownish gray solid.

IR KBr) 3448 (br), 1570, 1507, 1458, 1419, 1393, 1333, 1259, 1076, 1040, 984, 768, 668, 657, and 629 cm$^{-1}$.

$^1$H NMR (DMSO-$d_6$, 500 MHz) $\delta$7.18 (t), 7.30 (d), and 7.62 (d).

$^{13}$C NMR (DMSO-$d_6$, 125.7 MHz) $\delta$115.4, 122.8, 124.7, 131.3, 134.2, 149.0, 169.2, and 191.1.

Step 2

7-Hydroxymethyl-2-mercaptobenzothiazole

A mixture of crude 7-carboxy-2-mercaptobenzoic acid (480 mg, 2.27 mmol) and anhydrous tetrahydrofuran (7 mL) was placed under a nitrogen atmosphere and sonicated for a few minutes to give a fine suspension. The mixture was stirred and heated at reflux while 1.0M lithium aluminum hydride in tetrahydrofuran (4.5 mL) was cautiously added. The resulting mixture was heated at reflux for 60 minutes, then sonicated at room temperature for 15 minutes. The mixture was cooled in an ice bath, stirred, and acidified with 2N hydrochloric acid (18 mL). The mixture was diluted with water (18 mL) and extracted with ethyl acetate (4×20 mL). The combined extracts were washed with brine (20 mL), dried over sodium sulfate, swirled with charcoal, filtered, and evaporated under vacuum to afford 7-hydroxymethyl-2-mercaptobenzothiazole (228 mg) as a pale yellow powder.

$^1$H NMR (DMSO-$d_6$, 500 MHz) $\delta$3.32 (s, SH), 4.62 (d, CH$_2$OH), 5.66 (t, CH$_2$OH), 7.13 (d, H-6), 7.19 (d, H-4), and 7.33 (t, H-5).

$^{13}$C NMR (DMSO-$d_6$, 125.7 MHz) $\delta$61.7, 110.8, 121.2, 126.6, 127.0, 135.9, 141.9, and 190.7.

Preparative Example 6

4-HYDROXYMETHYL-2-MERCAPTOBENZOTHIAZOLE

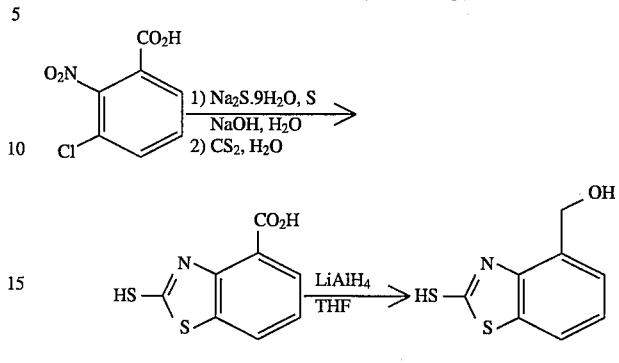

Step 1

4-Carboxy-2-mercaptobenzothiazole

Substitution of 3-chloro-2-nitro-benzoic acid for 2-chloro-3-nitro-benzoic acid in the procedure of Preparative Example 7 afforded 4-carboxy-2-mercaptobenzothiazole as a solid.

Step 2

4-carboxybenzothiazol-2-thiol

A solution of 4-carboxy-2-mercaptobenzothiazole (1.06 g, 5 mmol) in anhydrous tetrahydrofuran (15 mL) was cooled in an ice bath under nitrogen. A solution of lithium aluminum hydride (10 mL, 10 mmol) was added dropwise over 3 minutes and the flask was removed from the ice bath and allowed to warm to room temperature. After 10 minutes, the mixture was heated in a 60° C. oil bath for one hour. After cooling in an ice bath, hydrochloric acid (40 mL, 2N) was carefully added and the resulting solution was partitioned between ethyl acetate (60 mL) and water (40 mL). The ethyl acetate was removed and the aqueous layer was re-extracted with more ethyl acetate (2×60 mL). The combined extracts were washed with brine (20 mL), dried with magnesium sulfate, filtered and evaporated under vacuum to give a light yellow foam. The solid was suspended in a mixture of water (5 mL) and methylene chloride (10 mL). The pH was adjusted to 10 with 1N sodium hydroxide, the aqueous layer was filtered through a 0.45 micron acrodisc and the pH of the filtrate was adjusted to 3 with 2N hydrochloric acid. The precipitate was filtered, washed with water (20 mL) and the collected solid was dried overnight under a stream of nitrogen to give the title compound as a light yellow solid (0.63 g).

$^1$H NMR (DMSO-$d_6$, 500 MHz) $\delta$4.69 (s, CH$_2$OH), 5.29 (s, CH$_2$OH), 7.26 (t, ArH-6'), 7.38 and 7.55 (two d, ArH-5' and ArH-7') and 13.4 (s, NH).

$^{13}$C NMR (DMSO-$d_6$, 500 MHz) $\delta$59.67, 120.44, 124.48, 125.91, 127.72, 129.55, 138.79 and 190.66.

Preparative Example 7

4'-METHOXYBENZYL 7β-PHENOXYACETAMIDO-3-TRIFLUOROMETHANESULFONYLOXY-1-CARBADETHIACEPH-3-EM-4-CARBOXYLATE

1β-phenoxyacetamido-3-trifluoromethanesulfonyloxy-1-carbadethiaceph- 3-em-4-carboxylic acid (4.64 g, 10 m moles), dimethylformamidedineopentyl acetal (3.0 g, 13 m moles) and 4-methoxybenzyl alcohol (1.38 g, 10 m moles)

are dissolved in methylene chloride (50 ml) and the reaction mixture is stirred at room temperature for 48 hours. The reaction mixture is washed successively with water, 1N HCl, 5% NaHCO₃ and satd. NaCl soln. then dried over sodium sulfate and evaporated. Chromatography on silica gel gives the desired product.

Preparative Example 8

4'-METHOXYBENZYL 7β-PHENOXYACETAMIDO-3-(5-HYDROXYMETHYL-(BENZTHIAZOL-2-YL)-THIO-1-CARBA-1-DETHIACEPH-3-EM-4-CARBOXYLATE

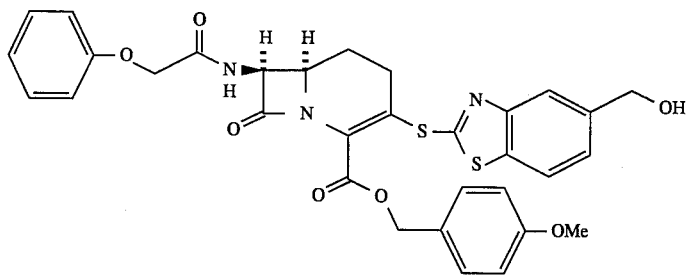

4'-Methoxybenzyl 7β-phenoxyacetamido-3-trifluoromethane sulfonyloxy-1-carba-1-dethiaceph-3-em4-carboxylate (4 mmole) is suspended in methylene chloride (40 mL) and cooled to −10° C. In another flask, sodium hydride (60% suspension in mineral oil, 160 mg. 4 mmole) is suspended in THF (4 mL). To this is added 5-hydroxymethyl-2-mercaptobenzthiazole (780 mg, 4 mmole) and the mixture stirred for 30 min. at room temperature. The resulting solution is added dropwise over 20 min. to the suspension of the triflate with rapid stirring. The reaction is allowed to come to room temperature and treated with KH₂PO₄ (0.5M solution, 10 mL) and water (50 mL). The two phases are separated and the organic phase is washed with water and saturated NaCl solution, dried over Na₂SO₄ and evaporated to give the crude product.

EXAMPLE 1

4'-METHOXYBENZYL 7β-AMMONIUM-3-(5-CHLOROMETHYL-2-BENZTHIAZOLYLTHIO)-1-carba-1-DETHIACEPH-3-EM-4—CARBOXYLATE p-TOLUENESULFONATE

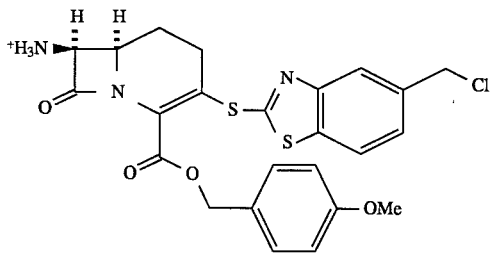

4'-Methoxybenzyl 7β-phenoxyacetamido-3-(5-hydroxymethyl-2-benzthiazolylthio)-1-carba-1-dethiaceph-3-em-4-carboxylate (2 mmole) is suspended in CH₂Cl₂ (65 mL) and cooled to −15° C. under N₂. Pyridine (3.2 mL) is added followed by PCl₅ (8% solution in CH₂Cl₂, 32 mL). The reaction mixture is stirred at −15° C. for 1.5 hrs, then cooled to −30° C. MeOH (10 mL) is added dropwise over 5 min. and stirring was continued for 1.5 hrs at −15° C. The ice bath is removed and the mixture is allowed to come to room temperature and stirred another 1.5 hrs.

KH₂PO₄ solution (40 mL, 0.5M) is added and the mixture stirred another 0.5 hr. The solvent is removed under reduced pressure. The residue is taken up in CH₂Cl₂. The aqueous layer is separated and extracted with CH₂Cl₂. The combined organic phase is washed with saturated NaCl solution, dried over Na₂SO₄ and evaporated to dryness. The residue is taken up in CH₂Cl₂ (10 mL) and treated with a solution of p-toluenesulfonic acid (0.57 g) in EtOAc (10 mL). The solid is filtered, washed with ether and dried to provide the product.

EXAMPLE 2

4'-METHOXYBENZYL 7β-AMINO-3-TRIFLOURORMETHANESULFONYLOXY-1-CARBA-DETHIACEPH-3-EM-4-CARBOXYLATE p-TOLUENE SULFONIC ACID SALT

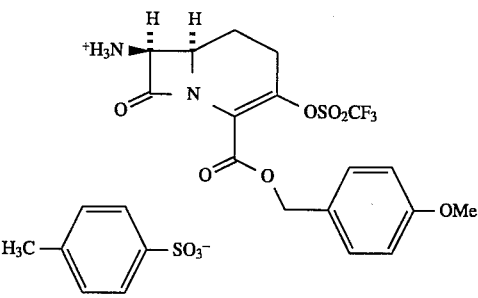

4'-methoxybenzyl 7β-phenoxyacetamido-3-trifluormethane-sulfonyloxy-1-carba-1-dethiaceph-3-em-4-carboxylate (2 mmoles) is dissolved in CH₂Cl₂ 40 mL and cooled to −15° C. under nitrogen. Pyridine (1.6 mL) is added followed by a 8% solution of PCl₅ in methylene chloride (16 mL). The reaction mixture is allowed to stir at −15 to −10° C. for 1 hr. The reaction mixture is cooled to −30° C. and treated with MeOH (10 mL). The temperature is raised to −15° C. and the mixture is stirred at −15 to 10° C. for 1 hour. The ice bath is removed and the mixture stirred for another hour. KH₂PO₄ (0.5M, 40 mL) is added and the reaction mixture is stirred at room temperature for 0.5 hr.

The organic solvent is removed by evaporation under reduced pressure and the residue partitioned between CH₂Cl₂ and water. The aqueous phase is extracted once with 40 mL methylene chloride and the combined organic extract is washed once with pH 7 buffer, then with saturated. NaCl, dried over $Na_2SO_4$ and evaporated to dryness. The residue is dissolved in EtOAc (10 mL) and treated with a solution of p-toluenesulfonic acid (450 mg in 8.0 mL EtOAc). This is diluted to turbidity with hexane. Scratching the flask induces crystallization. The crystals are allowed to stand overnight at 5° C. and were filtered off and washed with ether and dried to give the product.

EXAMPLE 3

4'-METHOXYBENZYL 7β-[2-(TRIPHENYLMETHYLAMINO-THIAZOL-4-YL)-2-Z-METHOXYIMINO]ACETAMIDO-3-TRIFLOURORMETHANESULFONYLOXY-1-CARBA-1-DETHIACEPH-3-EM-4-CARBOXYLATE

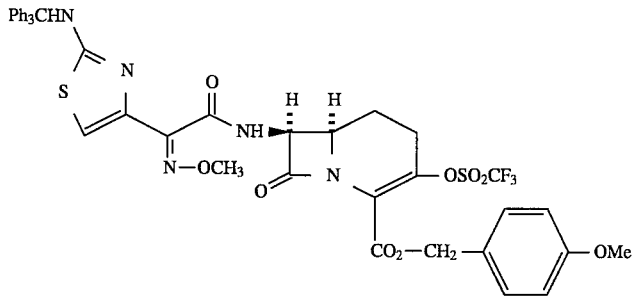

2-(Triphenylmethylamino)-Z-(methoxyimino)4-thiazole-acetic acid hydrochloride (1.1 eq) is dissolved in sieve-dried $CH_2Cl_2$ (3 mL) and cooled to -10° C. under nitrogen. Pyridine (37.4 µL, 2.4 eq.) is added followed by $POCl_3$ (22.2 µL, 1.2 eq). The reaction mixture is stirred at -10° C. for 45 min. To this is added 4'-methoxybenzyl 7β-amino-3-trifluoromethanesulfonyloxy-1-carba-dethiaceph-3-em-4-carboxylate p-toluene sulfonic acid salt (125 mg, 1.0 eq) and pyridine (18 µL) dissolved in 1.5 mL $CH_2Cl_2$. The reaction mixture is stirred at -10° C. for 0.5 hr and the ice bath removed. When the reaction mixture comes to room temperature (about 5 min.) the reaction mixture is diluted with methylene chloride and washed with pH 7 buffer, then with 0.01N HCl, then with pH 7 buffer, dried over $Na_2SO_4$ and evaporated. The residue of the crude product which is purified by preparative reverse phase chromatography on a C-18 column, using 80% $CH_3CN$/water as eluant followed by 90% $CH_3CN$/water. The fraction containing the product is evaporated to remove the $CH_3CN$ and the residue extracted with methylene chloride, dried over $Na_2SO_4$ and evaporated to give the pure product.

EXAMPLE 4

7β-[2-AMINO(THIAZOL-4-YL)-2-Z-(2-FLUORO)-ETHXY-IMINO]ACETAMIDO-3-{[5-(4-CARBAMOYLMETHYL-1,4-DIAZONIABICYCLO[2.2.2])OCT-1-YL) METHYL]-BENZTHIAZOL-2-YL-}THIO-1-CARBA-1-DETHIACEPH-3-EM-4-CARBOXYLATE CHLORIDE

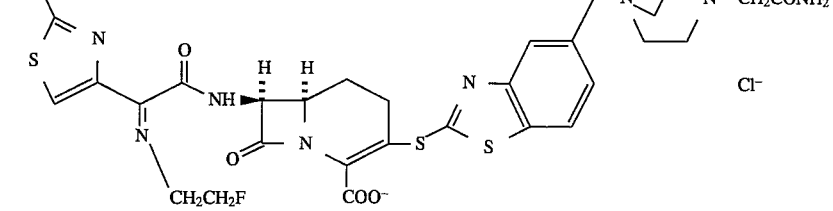

Step 1

4'-methoxybenzyl 7β-[2-(triphenylmethylaminothiazol-4-yl)-2-Z-(2-fluoro)-ethoxyimino]acetamido-3-(5-chloromethyl-2-benzthiazolylthio)-1-carba-1-dethiaceph-3-em-4-carboxylate

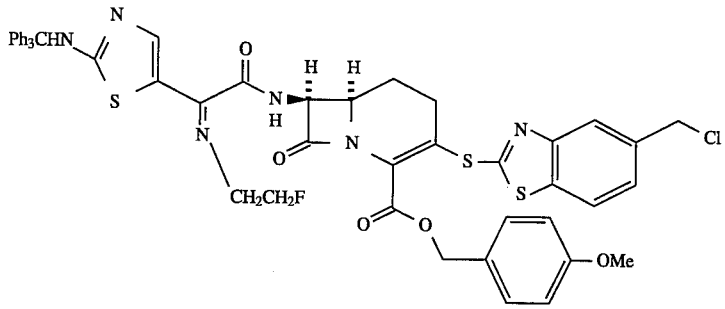

4'-Methoxybenzyl 7β-ammonium-3-(5-chloromethyl-2-benzthiazolythio)-1-carba-1-dethiaceph-3-em-4-carboxylate p-toluenesulfonate (0.2 mmole) is taken up in $CH_2Cl_2$ (10 mL) and washed with $NaHCO_3$ solution (10%, 5 mL), pH 7 buffer (0.4 M, phosphate) followed by saturated NaCl solution, then dried over $Na_2SO_4$ and evaporated to give the free amine.

2-(Triphenylmethylaminothiazol-4-yl)-2-Z-2-fluoroethoxyimino]acetic acid (91 mg) is dissolved in $CH_2Cl_2$ (3.5 mL) and cooled to −15° C. under $N_2$. Pyridine (19.4 μl, 1.2 eq) is added followed by $POCl_3$ (22.8 μl, 1.2 eq). The reaction mixture is stirred at −15° C. for 0.5 hr. To this is added a solution of the free amine from above in $CH_2Cl_2$ (1 mL) followed by pyridine (18 μl). Stirring is continued for 0.5 hr. The ice bath is removed and the reaction warmed to room temperature over 15 min. The reaction mixture is diluted with $CH_2Cl_2$ and washed with pH 7 buffer followed by 0.1N HCl, pH 7 buffer, saturated. NaCl solution., dried over $MgSO_4$ and evaporated. Preparative TLC gives the desired product.

Step 2

4'-methoxybenzyl 7β-[2-(triphenylmethylaminothiazol-4-yl)-2-Z-(2-fluoro)-ethoxyimino]acetamido-3(5-iodomethyl-2-benzthiazolylthio)-1-carba-1-dethiaceph-3-em -4carboxylate

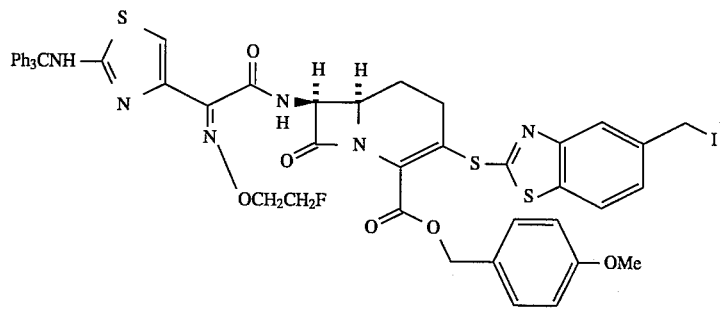

4'-Methoxybenzyl 7β-[2-(triphenylmethylaminothiazol-4-yl)-2-Z-2-fluoroethoxyimino]acetamido-3-(5-chloromethyl-2-benzthia zolylthio)-1-carba-1-dethiaceph-3-em-4-carboxylate (78 mg) is treated with KI (98 mg, 0.59 mmol) and allowed to stir for approximately 8 hrs at room temperature. The solvent is removed under reduced pressure and the residue taken up in chloroform and filtered. Upon evaporation of the filtrate, the desired iodide is obtained.

Step 3

4'-methoxybenzyl 7β-[2-(triphenylmethylaminothiazol-4-yl)-2-Z-(2-fluoro)-ethoxyimino]acetamido-3-{[5-(4-carbamoylmethyl-1,4-diazoniabicyclo[2.2.2])oct-1-yl)methyl]-benzthiazol-2-yl-}thio-1-carba-1-dethiaceph-3-em-4-carboxylate bis (trifluoromethanesulfonate)

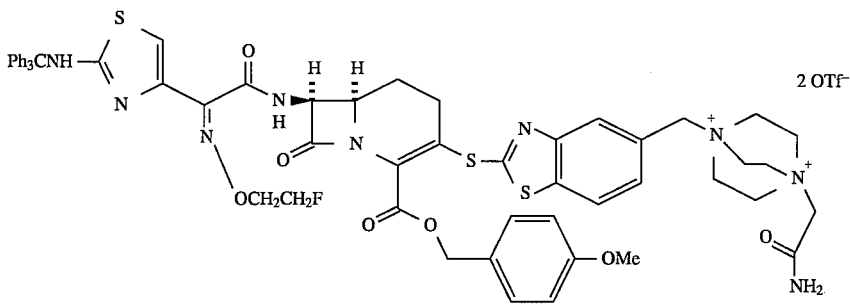

4'-Methoxybenzyl 7β-[2-(triphenylmethylaminothiazol-4-yl)-2-Z-2-fluoroethoxyimino]acetamido-3-(5-iodomethyl-2-benzthiazolythio)-1-carba-1-dethiaceph-3-em-4-carboxylate is dissolved in CH₃CN (2 mL) under N₂ and treated with 1-carbamoylmethyl-4-aza-1-azonia-bicyclo[2.2.2]octane trifluoromethyl sulfonate (1.2 eq.), followed by AgOTf (1.2 eq.) dissolved in CH₃CN (0.5 mL). The reaction mixture is stirred under N₂ for 1 hr. The solids are filtered off through a bed of celite, and washed with CH₃CN (10 mL). The combined filtrate and washings are evaporated to give the desired product.

Step 4

7β-[2-amino(thiazol-4-yl)-2-Z-(2-fluoro)-ethoxyimino]acetamido-3-{[5-(4-carbamoylmethyl-1,4-diazoniabicyclo [2.2.2])oct-1-yl) methyl]-benzthiazol-2-yl-}thio-1-carba-1-dethiaceph-3-em-4-carboxylate chloride $CH_3CN/H_2O$ and the hexane is extracted once more with 10% $CH_3CN/H_2O$. The aqueous phase is filtered through a 0.45 μm filter and purified by preparative HPLC on a Waters Delta-Pak C-18, 100 Å, 19 mm×30 cm column, using a 0–25% $CH_3CN/0.12M\ NH_4Cl$, 20 min. gradient. The solution from the column containing the product is concentrated and loaded on a 5 mL bed of Amberchrome 161 C resin packed in water, washed with water (25 mL) followed by 50% $CH_3CN/H_2O$ (20 mL). The product eluting in the 50% $CH_3CN/H_2O$ eluant is freeze dried to give the product.

EXAMPLE 5

7β-[2-(AMINOTHIAZOL-4-YL)-2-Z-METHOXYIMINO]ACETAMIDO-3-{[5-(4-CARBAMOYLMETHYL-1,4-DIAZONIABICYCLO [2.2.2])OCT-1-YL)M-

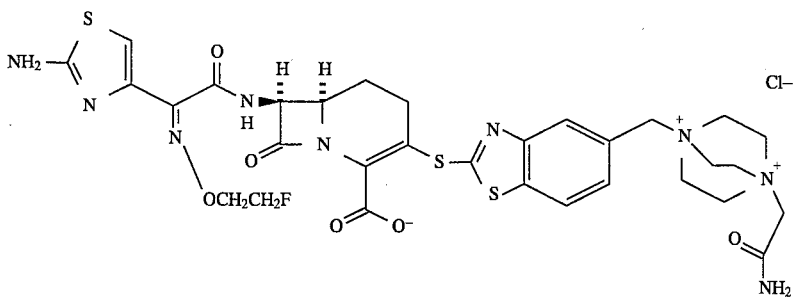

4'-Methoxybenzyl 7β-[2-(triphenylmethylaminothiazol-4-yl)-2-Z-2-fluoroethoxyimino]acetamido-3-{[5-(4-carbamoylmethyl-1,4-diazoniabicyclo [2.2.2]oct-1-yl)methyl]-benzthiazol-2-yl-}thio-1-carba-1-dethiaceph-3-em-4-carboxylate bis (trifluoromethylsulfonate) is dissolved in anisole (1 mL), under N₂ and treated with trifluoroacetic acid (3 mL). The reaction is stirred at room temperature for 15 minutes. Toluene is added and the mixture evaporated to dryness. The residue is partitioned between hexane and 10%

ETHYL]-BENZTHIAZOL-2-YL-}THIO-1-CARBA-1-DETHIACEPH-3-EM-4-CARBOXYLATE CHLORIDE

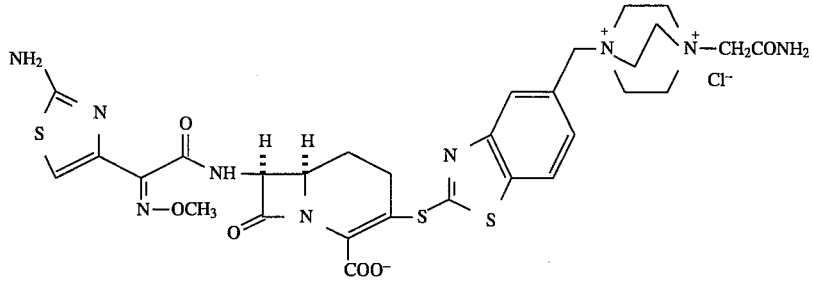

Step 1

4'-methoxybenzyl 7β-[2-(triphenylmethylaminothiazol-4-yl)-2-Z-methoxyimino]acetamido-3-(5-chloromethyl-2-benzthiazolylthio)-1-carba-1-dethiaceph-3-em-4-carboxylate Substitute 2-(triphenylmethylaminothiazol-4-yl)-2-Z-methoxyimino]acetic acid hydrochloride for 2-(triphenylmethylaminothiazol-4-yl)-2-Z-2-fluoroethoxyimino]acetic acid in the procedure of example 4, step 1, except that an extra 1 equivalent of pyridine is used in the acid chloride forming reaction, to obtain the desired product.

EXAMPLE 6

7β-[2-(AMINOTHIAZOL-4-YL)-2-Z-(HYDROXYIMINO)ACETAMIDO-3-{[5-(4-CARBAMOYLMETHYL-1,4-DIAZONIABICYCLO[2.2.2])OCT-1-YL)METHYL]-BENZTHIAZOL-2-YL-}THIO-1-CARBA-1-DETHIACEPH-3-EM 4-CARBOXYLATE CHLORIDE

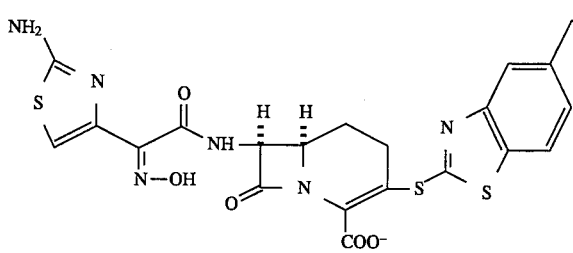
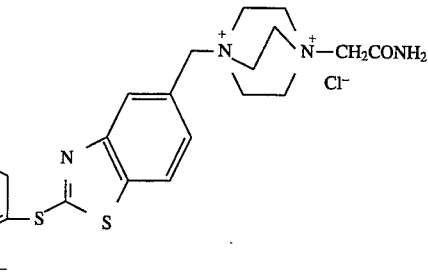

Step 1
4'-methoxybenzyl 7β-[2-(triphenylmethylaminothiazo-4-yl)-2-Z-triphenylmethoxyimino]acetamido-3-(5-chloromethyl-2- benzthiazolythio)-carba-1-dethiaceph-3-em -4-carboxylate Substituting 2-(triphenylmethylaminothiazol-4-yl)-2-Z-triphenylmethoxyimino]acetic acid for 2-(triphenylmethylaminothiazol-4-yl)-2-Z-2-fluoroethoxyimino]acetic acid in the procedure of example 4, step 1, one obtains the desired product.

Step 2
4'-methoxybenzyl 7β-[2-(triphenylmethylaminothiazo-4-yl)-2-Z-triphenylmethoxyimino]acetamido-3-(5-iodomethyl-2-benzthiazoylthio)-1-carba-1-dethiaceph-3-em-4-carboxylate Following the procedure of example 5, step 2 and starring with the product of step 1, one obtains the desired product.

Step 3
4'-methoxybenzyl 7β-[2-(triphenylmethylaminothiazol-4-yl)- 2-Z-triphenylmethoxyimino]acetamido-3-{[5-(4-carbamoylmethyl-1,4-diazoniabicyclo[2.2.2])oct-1-yl)methyl]-benzthiazol-2-yl-}thio-1-carba-1-dethiaceph-3-em-4-carboxylate bis (trifluoromethylsulfonate)

Starring with the product of Step 2 and following the procedure of Example 4, Step 3, one obtains the desired product.

Step 4
7β-[2-(aminothiazol-4-yl)-2-Z-(hydroxyimino]acetamido-3{[5-(4-carbamoylmethyl-1,4-diazoniabicyclo[2.2.2])oct-1-yl) methyl]-benzthiazol-2-yl-}thio-1-carba-1-dethiaceph-3-em-4-carboxylate chloride 4'-Methoxybenzyl 7β-[2-(Triphenylmethylaminothiazol-4-yl)-2-Z-Triphenylmethoxyimino]acetamido-3-{[5-(4-carbamoylmethyl-1,4-diazoniabicyclo[2.2.2])oct-1-yl)methyl]-benzthiazol-2-yl-}thio-1-carba-1-dethiaceph-3-em-4-carboxylate bis (trifluoromethylsulfonate) from step 3 is treated according to the procedure of example 5, step 4, to give the desired product.

Step 2
4'-methoxybenzyl 7β-[2-(triphenylmethylaminothiazol-4-yl)-2-Z-methoxyimino]acetamido-3-(5-iodomethyl-2-benzthiazolylthio)-1-carba-1-dethiaceph-3-em-4-carboxylate 4'-Methoxybenzyl 7β-[2-(triphenylmethylaminothiazol-4-yl)-2-Z-methoxyimino]acetamido-3-(5-chloromethyl-2-benzthiazolyl-thio)-1-carba-1-dethiaceph-3-em4-carboxylate (0.077 mole) is dissolved in acetone (2.2 mL) and treated with KI (0,59 mmole), The mixture is allowed to stir overnight at room temperature. The solvent is removed under reduced pressure and the residue taken up in $CHCl_3$ and filtered. The filtrate is evaporated to give the product.

Step 3
4'-methoxybenzyl 7β-[2-(triphenylmethylaminothiazol-4-yl)-2-Z-methoxyimino]acetamido-3-{[5-(4-carbamoylmethyl-1,4-diazoniabicyclo [2.2.2])oct-1-yl)methyl]-benzthiazol-2-yl-}thio-1-carba-1-dethiaceph-3-em-4-carboxylate bis (trifluoromethylsulfonate)

Starring with the product of Step 2 and following the procedure of example 4, step 3 one obtains the desired product.

Step4
7β-[2-(aminothiazol-4-yl)-2-Z-methoxyimino]acetamido-3-{[5-(4-carbamoylmethyl-1,4-diazoniabicyclo[2.2.2])oct-1-yl)methyl]-benzthiazol-2-yl-}thio-1-carba-1-dethiaceph-3-em-4-carboxylate chloride 4'-Methoxybenzyl 7β-[2-(triphenylmethylaminothiazol-4-yl)-2-Z-methoxyimino]acetamido-3-{[5-(4-carbamoylmethyl-1,4-diazoniabicyclo [2.2.2])oct-1-yl)methyl]-benzthiazol-2-yl-}thio-1-carba-1-dethiaceph-3-em-4-carboxylate bis (trifluoromethylsulfonate) is dissolved in anisole (1.3 mL), under $N_2$ and treated with trifluoroacetic acid (3.5 mL). The reaction is stirred at room temperature for 10 min. Toluene is added and the mixture evaporated to dryness. The residue is treated with hexane and the hexane soluble material decanted off. The residual hexane is removed by evacuation. The residue is treated with water and sufficient $CH_3CN$ to effect solubilization. The pH is adjusted to 5.9 and filtered through a 0.45 μm filter and purified by reverse phase HPLC as described in example 6, step 4 to give the product.

EXAMPLE 7

7β-[2-(AMINOTHIAZOL-4-YL)-2-Z-BENZYLOXYIMINOIMINO]ACETAMIDO-3-{[5-(4-CARBAMOYLMETHYL-1,4-DIAZONIABICYCLO[2.2.2])OCT-1-YL)METHYL]-BENZTHIAZOL-2-YL-}THIO-1-CARBA-1-DETHIACEPH-3-EM-4-CARBOXYLATE CHLORIDE

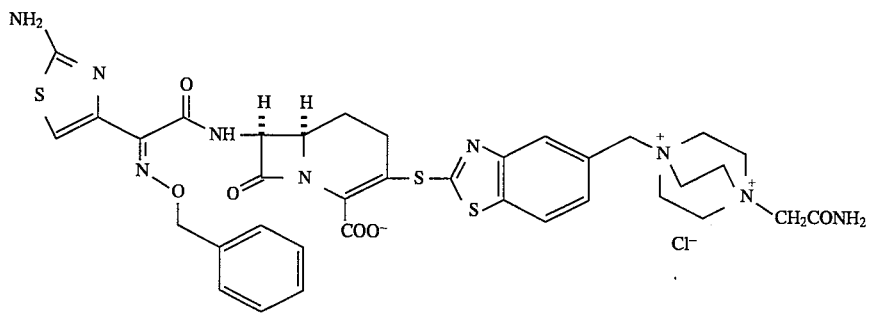

Step 1

4'-methoxybenzy 7β-[2-(triphenylmethylaminothiazol-4-yl)-2-Z-benzyloxyimino]acetamido-3-( 5-chloromethyl-2-benzthiazolylthiol)-1-carba-1-dethiaceph-3-em-4-carboxylate Substituting 2-(triphenylmethylaminothiazol-4-yl)-2-Z-benzyloxyimino]acetic acid for 2-(triphenylmethylaminothiazol-4-yl)-2-Z-2-fluoroethoxyimino]acetic acid in the procedure of example 4, step 1, one obtains the desired product.

Step 2

4'-methoxybenzyl 7β-[2-(triphenylmethylaminothiazol-4-yl)-2-Z-benzyloxyimino ]acetamido-3-(5-iodomethyl-2-benzthiazolylthio)-1-carba1-dethiaceph-3-em-4-carboxylate Following the procedure of Example 5, Step 2, but starring with the product of step 1, one obtains the desired product.

Step 3

4'-methoxybenzyl 7β-[2-(triphenylmethylaminothiazol-4-yl)-2-Z-benzyloxyimino]acetamido-3-{[5-(4-carbamoylmethyl-1,4-diazoniabicyclo [2.2.2])oct-1-yl)methyl]-benzthiazol-2-yl-}thio-1-carba-1-dethiaceph-3-em-4-carboxylate bis (trifluoromethylsulfonate)

Starting with the product of Step 2 and following the procedure of Example 5, Step 3, one obtains the desired product.

Step 4

7β-[2-(aminothiazol-4-yl)-2-Z-benzyloxyimino]acetamido-3-{[5-(4-carbamoylmethyl-1,4-diazoniabicyclo[2.2.2])oct-1-yl) methyl]-benzthiazol-2-yl-}thio-1-carba-1-dethiaceph-3-em-4-carboxylate chloride 4'-Methoxybenzyl 7β-[2-(triphenylmethylaminothiazol-4-yl)-2-Z-benzyloxyimino ]acetamido-3-{[5-(4-carbamoyl-methyl-1,4-diazoniabicyclo [2.2.2])oct-1-yl)methyl]-benzthiazol-2-yl-}thio-1-carba-1-dethiaceph-3-em-4-carboxylate bis (trifluoromethylsulfonate) from step 3 is treated according to the procedure of example 5, step 4, to give the desired product.

EXAMPLE 8

7β-[2-(AMINOTHIAZOL-4-YL)-2-Z-METHOXYIMINO]ACETAMIDO-3-{[5-(3-METHYLIMIDAZOLIUM)-METHYL]BENZTHIAZOL-2-YL-}THIO1-CARBA-1-DETHIACEPH-3-EM-4-CARBOXYLATE

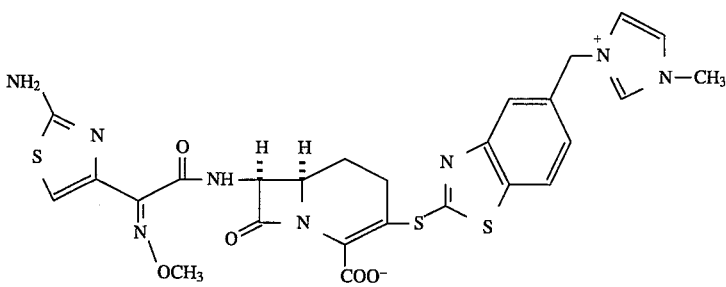

Step 1

4'-methoxybenzyl 7β-[2-(triphenylmethylaminothiazo4-yl)-2-Z-methoxyimino]acetamido-3-{[5-(3-methylimidazolium)-methyl]-benzthiazol-2-yl-}thio-1-carba-1-dethiaceph-3-em4-carboxylate iodide 4'-Methoxybenzyl 7μ-[2-(triphenylmethylaminothiazol-4-yl)-2-Z-methoxyimino]acetamido-3-(5-iodomethyl-2-benzthiazolylthio)-1-carba-1-dethiaceph-3-em-4-carboxylate (0.12 mmole) in $CH_3CN$(4.5 mL) and THF (2.2 mL) is treated with 1-methylimidazole (23.8 μl, 0.29 mmole). The reaction mixture is stirred at room temperature for 3 hrs. The reaction mixture is partitioned between $CH_2Cl_2$ and HCL solution (2N), and the aqueous phase is separated and extracted with $CH_2Cl_2$. The combined organic phases are washed with HCl (2N), pH 7 phosphate buffer (0.4M), and saturated NaCl soln., then dried over $Na_2SO_4$ and evaporated to give the product.

Step 2

7β-[2-(aminothiazol-4-yl)-2-Z-methoxyimino]acetamido-3-{[5-(3-methylimidazolium)-methyl]benzthiazol- 2-yl-]thio-1-carba-1-dethiaceph-3-em-4-carboxylate 4'-Methoxybenzyl 7β-[2-(triphenylmethylaminothiazol-4-yl-2-Z-methoxyimino]acetamido-3-{[5-(3-methylimidazolium)-methyl]-benzthiazol-2-yl-}thio-1-carba-1-dethiaceph-3-em-4-carboxylate iodide is treated with anisole (0.77 mL) and TFA (2.5 mL). The reaction is stirred at room temperature for 15 min. and worked up and purified as described in example 5, step 4 to give the desired product.

EXAMPLE 9

7β-[2-(2-AMINOTHIAZOL-4-YL)-2-Z-METHOXYIMINO]ACETAMIDO-3-{5-[4-(2-HYDROXYETHYL)-1,4-DIAZONIABICYCLO [2.2.2])OCT-1-YL)METHYL]-BENZTHIAZOL-2-YL-}THIO1-CARBA-1-DETHIACEPH-3-EM-4-CARBOXYLATE CHLORIDE

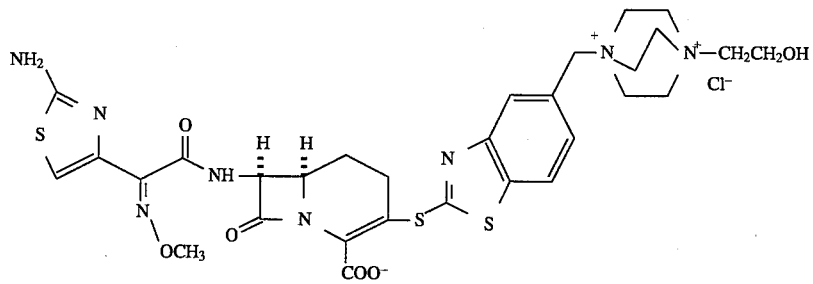

Step 1

4'-methoxybenzyl 7β-[2-(triphenylmethylaminothiazol-4-yl)-2-Z-methoxyimino]acetamido-3-{5-[4-(2-hydroxyethyl)-1,4-diazoniabicyclo[2.2.2](oct-1-yl)methyl]-benzthiazol-2-yl-}thio-1-carba-1-dethiaceph-3-em-4-carboxylate bis (tfifiuoromethylsulfonate)

Starting with the product of Example 5, Step 2 and following the procedure of Example 4, Step 3, but substituting 1-carbamoylmethyl-4-aza-1-azoniabicyclo[2.2.2]octane tfifiuoromethylsulfonate, one obtains the desired product.

Step 2

7β-[2-(2-aminothiazo14-yl)-2-Z-methoxyimino]acetamido-3-{5-[4-(2-hydroxyethyl)-1,4-diazoniabicyclo [2.2.2])oct-1-yl) methyl]-benzthiazol-2-yl-}thio-1-carba-1-dethiaceph-3-em4-carboxylate chloride The product of Step 1 is treated under the conditions of example 5, step 4 to give the desired product.

EXAMPLE 10

7β-[2-(2-AMINOTHIAZOL4-YL)-2-Z-METHOXYIMINO]ACETAMIDO-3-{[5-(3-AMINOPROPYL)-IMIDAZOLIUM)METHYL]-BENZTHIAZOL-2-YL-}THIO-1-CARBA-1-DETHIACEPH-3-EM-4-CARBOXYLATE

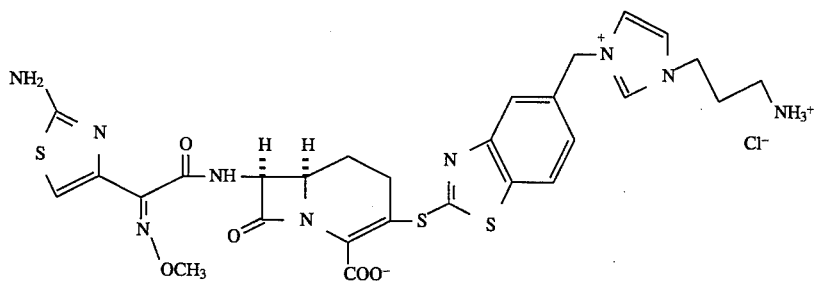

Step 1

4'-methoxybenzyl 7β-[2-(triphenylmethylaminothiazol-4-yl)-2-Z-methoxyimino ]acetamido-3-{[5-( 3-triphenylmethylaminopropyl)-imidazolium)-methyl]-benzthiazol-2-yl-}thio-1-carba-1-dethiaceph-3-em-4-carboxylate iodide Starting with the product of Example 5, Step 2 and following the procedure of example 8, step 1, but substituting 1-methylimidazole with 1-(3-triphenylmethylaminopropyl)-imidazole, obtains the desired product.

Step 2

7β-[2-(2-aminothiazol-4-yl)-2-Z-methoxyimino]acetamido-3-{[5-(3-aminopropyl)-imidazolium)-methyl]-benzthiazol-2-yl-]thio-1-carba-1-dethiaceph-3-em-4-carboxylate The product of Step 1 is treated under the conditions of Example 5, Step 4 to give the desired product.

EXAMPLE 11

7β-[2-(AMINOTHIAZOL-4-YL)-2-Z-METHOXYIMINO]ACETAMIDO-3-{[4-(4-CARBAMOYLMETHYL-1,4-DIAZONIABICYCLO[2.2.2])OCT-1-YL)METHYL]-BENZTHIAZOL-2-YL-}THIO-1-CARBA-1-DETHIACEPH-3-EM-4-CARBOXYLATE CHLORIDE

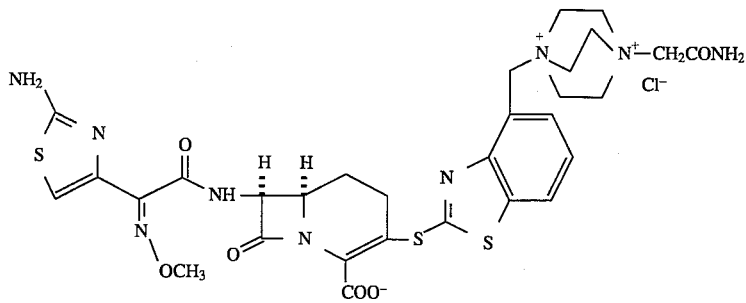

Step 1
4'-methoxybenzyl 7β-phenylacetamido-3-(4-hydroxymethyl-(benzthiazol-2-yl)-thio-1-carba-1-dethiaceph-3-em-4-carboxylate 4'-Methoxybenzyl 7β-phenylacetamido-3-trifluormethanesulfonyloxy-1-carba-1-dethiaceph-3-em-4-carboxylate (0.256 mmole) is suspended in methylene chloride (3.3 mL) and cooled to −10° C. In another flask sodium hydride (50% suspension in mineral oil, (12.3 mg, 0.256 mmole) is suspended in THF (0.75 mL). To this is added 4-hydroxymethyl-2-mercaptobenzthiazole (50 mg, 0.253 mmole) and the mixture stirred for 10 minutes at room temperature. The resulting solution is added dropwise to the suspension of the triflate with rapid stirring. The reaction is allowed to stir at −5° to 0° C. for 3 hrs. and then at room temperature for 0.5 hr and then treated with $KH_2PO_4$ (0.5M solution., 1 mL), water (5 mL) and $CH_2Cl_2$ (10 mL). The mixture is stirred at room temperature for 5 minutes. The two phases are separated and the organic phase washed with water and saturated NaCl solution, and then dried over $Na_2SO_4$ and evaporated to give the crude product.

Step 2
4'-methoxybenzyl 7β-phenylacetamido-3-(4-chloromethyl-benzthiazol-2-yl )-thio-1-carba-1-dethiceph-3-em-4-carboxylate The product from step 1 is suspended in $CH_2Cl_2$ (3.3 mL) and cooled to 0° C. under $N_2$. Methanesulfonyl chloride (1.2 eq.) and $Et_3N$ (1.1 eq.) are added.

The reaction is worked up by partitioning between $CH_2Cl_2$ and water, drying the organic phase over $Na_2SO_4$, and evaporaring to dryness to give the mesylate.

The mesylate is dissolved in acetone (2.3 mL) and treated with LiCl (5 eq.). The reaction is allowed to stir at for 3 hrs. $CH_2Cl_2$ (10 mL) is added and the precipitate filtered off. The filtrate is evaporated to dryness. The residue was taken up in $CH_2Cl_2$ washed with water, dried and evaporated to give the product.

Step 3
4'-methoxybenzyl 7β-ammonium-3-(4-chloromethyl-2-benzthiazolythio)-1-carba-1-dethiaceph-3-em-4-carboxylate p-toluenesulfonate 4'-Methoxybenzyl 7β-phenylacetamido-3-(4-chloromethyl-(benzthiazol-2-yl)-thio-1-carba-1-dethiaceph-3-em-4-carboxylate is treated according to the procedure of example 4. After addition of the p-toluenesulfonic acid, ether is added to the reaction mixture and the precipitated solid filtered off and washed with ether to give the product.

Step 4
4 '-methoxybenzyl 7β-[2-(triphenylmethylaminothiazol-4-yl)-2-Z-methoxyimino]acetamido-3-(4-chloromethyl-2-benzthiazolylthio)-1-carba-1-dethiaceph-3 -em-4-carbox ylate The product from Step 3 is treated under the conditions of Example 4, Step 1 to give the desired product.

Step 5
4'-methoxybenzyl 7β-[2-(triphenylmethylaminothiazol-4-yl)-2-Z-methoxyimino]acetamido-3-(4-iodomethyl-2-benzthiazolylthio)-carba-1-dethiaceph-3-em-4-carboxylate The product from Step 4 is treated according to the procedure of Example 5, Step 2, to give the desired product.

Step 6
4'-methoxybenzyl 7β-[2-(triphenylmethylaminothiazol-4-yl)-2-Z-methoxyimino]acetamido-3-{[4-(4-carbamoylmethyl-1,4-diazoniabicyclo [2.2.2])oct-1-yl)methyl]-benzthiazol-2-yl-}thio-1-carba-1-dethiaceph-3-em-4-carboxylate bis (trifluoromethylsulfonate)

The product from Step 5 (0.247 mmole) is treated according to the conditions of Example 4, Step 3 to give the desired product.

Step 7
7β-[2-(aminothiazol-4-yl)-2-Z-methoxyimino]acetamido-3-{[4-(4-carbamoylmethyl-1,4-diazoniabicyclo[2.2.2])oct-1-yl)methyl]-benzthiazol- 2-yl-]thio-1-carba-1-dethiaceph-3-em-4-carboxylate chloride The product from Step 6 is treated according to the conditions of Example 5, Step 4, to give the desired product.

EXAMPLE 12

7β-[2-(AMINOTHIAZOL-4-YL)-2-Z-METHOXYIMINO]ACETAMDO-3-{[6-(4-CARBAMOYLMETHYL-1,4-DIAZONIABICYCLO[2.2.2]OCT-1-YL)METHYL]-BENZTHIAZOL-2-YL-}THIO-1-CARBA-1-DETHIA CEPH-3-EM-4-CARBOLXYLATE CHLORIDE

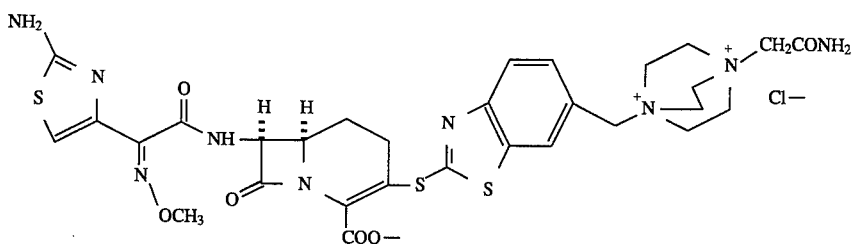

Step 1
4'-methoxybenzyl 7β-[2-(triphenylmethylaminothiazol-4-yl)-2-Z-methoxyimino]acetamido-3-(6-hydroxymethyl-2-benzthiazolylthio)-1-carba-1-dethiaceph-3-em-4-Carboxylate To sodium hydride (50% suspension in oil, 4.8 mg, 0.1 mmole suspended in THF (0.3 mL) under $N_2$, is added 6-hydroxy-methyl-2-mercaptobenzthiazole (0.103 mmole). The reaction mixture is stirred for 10 min. then cooled to −60° C. 4'-methoxy-benzyl 7β-[2-(aminothiazol-4-yl)-2-Z-methoxyimino]acetamido-3-trifluorormethanesulfonyloxy-1-carba-1-dethiaceph-3-em-4-carboxylate (0.099 mmole) from Example 5 in $CH_2Cl_2$ (1.3 mL) is added. The reaction temp is raised to −20° C. and the mixture stirred at −20° to −15° C. for 50 min. Work up as described in Example 11, Step 1, provides the product as a mixture of $\Delta^3$ and $\Delta^2$ isomers.

Step 2
4'-methoxybenzyl 7β-[2-(triphenylmethylaminothiazol-4-yl)-2-Z-methoxyimino]acelamido-3-(6-iodomethyl-2-benzthiazolyhio)-1-carba-1-dethiaceph-3-em-4-carboxylate The product from step 4 of Example 11 in $CH_2Cl_2$ (1.7 mL), cooled to 0° C. under $N_2$, is treated with MsCl (13 μl, 0.168 mmole) and $Et_3N$ (22 μl, 0.158 mmole). After 45 minutes, additional portions of MsCl (6 μl, 0.0775 mmole) and $Et_3N$ (11 μl, 0.078 mmole) are added and the reaction worked up to give the mesylate.

The mesylate is dissolved in acetone (1.8 mL) and treated with KI (84 mg, 0.506 mmole). The reaction is allowed to stir at room temperature for 2 hrs. The solvent is removed under reduced pressure and the residue taken up in $CH_2Cl_2$ and filtered. The filtrate is evaporated to give the product as a mixture of $\Delta^3$ and $\Delta^2$ isomers.

Step 3
4'-methoxybenzyl 7β-[2-(triphenylmethylaminothiazol-4-yl)-2-Z-methoxyimino]acetamido-3-{[6-(4-carbamoylmethyl-1,4-diazoniabicyclo [2.2.2])oct-1-yl)methyl]-benzthiazol-2-yl-}thio-1-carba-1-dethiaceph-3-em-4-carboxylate bis (trifluoromethylsulfonate)

The product from Step 2 is treated according to the conditions of Example 4, Step 3 to give the desired product.

Step 4
7β-[2-(aminothiazol-4-yl)-2-Z-methoxyimino]acetamido-3-{[6-(4-carbamoylmethyl-1,4-diazoniabicyclo[2.2.2])oct-1-yl) methyl]-benzthiazol-2-yl-}thio-1-carba-1-dethiaceph-3-em-4-carboxylate chloride The product from Step 3 is treated according to the conditions of Example 5, Step 4 to give the desired product and the $\Delta^2$ isomer (3.5 mg).

EXAMPLE 13

7β-[2-(AMINOTHIAZOL4-YL)-2-Z-METHOXYIMINO]ACETAMIDO-3-{4-[4-(4-CARBAMOYLMETHYL-1,4-DIAZONIABICYCLO [2.2.2]OCT-1-YL)-METHYLPHENYL]-THIAZOL-2-YL}-THIO-1-CARBA-1-DETHIACEPH-3-EM-4-CARBOXYLATE CHLORIDE

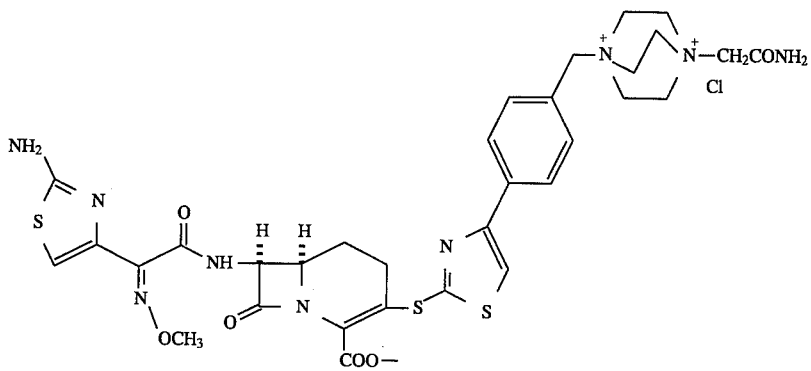

Step 1
4'-methoxybenzyl 7β-[2-(triphenylmethylaminothiazol-4-yl)-2-Z-methoxyimino]acetamido-3-[4-(4-hydroxymethylphenyl)-thiazol-2-yl]thio-1-carba-1-dethiaceph-3-em-4-carboxylate Sodium hydride (50% suspension in oil, 4.8 mg, 0.1 mmole) is suspended in THF (0.3 mL) at room temperature under $N_2$. 4-( 4-hydroxymethylphenyl)-2-mercaptothiazole (23 mg, 0.103 mmole) is added. The reaction mixture is stirred at room temperature for 10 min. then added to a solution of 4'-methoxybenzyl 7β-[2-(aminothiazo4-yl)-2-Z- methoxyimino]acetamido-3-tfifluormethanesulfonyloxy-1-carba-1-dethiaceph-3-em4-carboxylate (0.0716 mmole) from example 3, in $CH_2Cl_2$ (1.3 mL), cooled to 0° C. under $N_2$. The reaction mixture is stirred at 0° C. for 35 min. Work up as described in example 11, step 1 provides the product.

Step 2

4'-methoxybenzyl 7β-[2-(triphenylmethylaminothiazol-4-yl)-2-Z-methoxyimino]acetamido-3 -[4-(4-iodomethylphenyl)-thiazol-2-yl]-thio-1-carba-1-dethiaceph-3-em4-carboxylate The product from Step 1 is treated under the conditions of Example 12, Step 2, to give the desired product.

Step 3

4'-methoxybenzyl 7β-[2-(triphenylmethylaminothiazol4-yl)-2-Z-methoxyimino]acetamido-3-{4-[4-(4-carbamoylmethyl-1,4-diazoniabicyclo[2.2.2]oct-1-yl)-methylphenyl]-thiazol-2-yl}-thio-1-carba-1-dethiaceph-3-em4-carboxylate bis (tfifluoromethanesulfonate)

The product from Step 2 is treated according to the conditions of Example 4, Step 3 to give the desired product.

Step 4

7β-[2-(aminothiazol-4-yl)-2-Z-methoxyimino]acetamido-3-{4-[4-(4-carbamoylmethyl-1,4-diazoniabicyclo[2.2.2]oct-1-yl)-methylphenyl]-thiazol-2-yl}-thio-1-carba-1-dethiaceph-3-em-4-carboxylate chloride The product from Step 3is treated according to the conditions of Example 5, Step 4, to give the desired product.

EXAMPLE 14

7β-[2-(AMINOTHIAZOL-4-YL)-2-(Z-METHOXYIMINO]ACETAMIDO-3-[4-(4-CARBAM0YLMETHYL-1,4-DIAZONIABICYCLO[2.2.2]-OCT-1-YL)-METHYL-1,3-THIAZOLO[5,4-B]THIOPHENE-2-YL]-THIO-1-CARBA-1-DETHIACEPH-3-EM-4-CARBOXYLATE CHLORIDE

To sodium hydride (60% suspension in oil, 8 mg, 0.2 mmole) suspended in THF (0.5 mL) at room temperature under $N_2$, is added 2-mercapto-4-hydroxymethyl-1,3-thiazolo[5,4-b]thiophene (40.6 mg, 0.2 mmole). The reaction mixture is stirred at room temperature for 15 minutes, then 0.26 mL of this solution is added to a solution of 4'-methoxybenzyl 7β-[2-(triphenylmethylaminothiazol-4-yl)-2-Z-methoxyimino]actamido-3-tfifluormethanesulfonyloxy-1-carba-1-dethiaceph-3-em4-carboxylate (0.1 mmole) from example 5, in $CH_2Cl_2$ (2.5 mL), cooled to −15° C. under $N_2$. The reaction mixture is stirred at −15° C. for 45 minutes. Work up as described in example 13, step 1, provides the product.

Step 2

4'-methoxybenzyl 7β-[2-(triphenylmethylaminothiazol-4-yl)-2-(Z-methoxyimino)acetamido-3-[4-iodomethyl-1,3-thiazolo-(5,4-b)-thiophene-2-yl]-thio-1-carba-1-dethiaceph-3-em-4-carboxylate The product from Step 1 is treated under the conditions of Example 12, Step 2 to give the desired product.

Step 3

4'-methoxybenzyl 7β-[2-(triphenylmethylaminothiazol-4-yl)-2-(Z-methoxyimino)acetamido-3-[4-(4-carbamoylmethyl-1,4-diazoniabicyclo [2.2.2]-oct-1-yl)-methyl-1,3-thiazolo[5,4-b]thiophene-2-yl]-thio-1-carba-1-dethiaceph-3-em-4-carboxylate bis (trifluoromethanesulfonate)

The product from Step 2 is treated according to the conditions of Example 4, Step 3 to give the desired product.

Step 4

7β-[2-(aminothiazol-4-yl)-2-(Z-methoxyimino)acetamido-3-[4-(4-carbamoylmethyl-1,4-diazoniabicyclo [2.2.2]-oct-1-yl)-methyl-1,3thiazolo[5,4-b]thiophene-2-yl]-thio-1-carba-1-dethiaceph-3-em-4-carboxylate chloride The product from Step 3 is treated according to the conditions of Example 5, Step 4, to give the desired product.

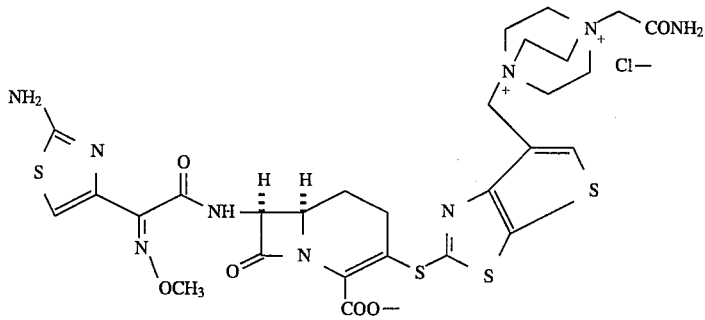

Step 1

4 '-methoxybenzyl 7β-[2-(triphenylmethylaminothiazo4-yl))-2-(Z-methoxyimino]acetamido-3-[4-hydroxymethyl-1,3-thiazo-(5,4-b)-thiophene-2-yl]-thio-1-carba-1-dethiaceph-3 -em 4-carboxylate

EXAMPLE 15

7β-[2-(5-AMINO-1,2,4-THIADIAZOL-3-YL)-(2-Z-2-METHOXYIMINO)]ACETAMIDO-3-{5-(4-CARBAMOYLMETHYL-1,4-DIAZONIABICYCLO[2.2.2])OCT-1-YL) METHYL]-BENZTHIAZOL-2-YL-}THIO-1-CARBA-1-DETHIACEPH-3-EM-4-CARBOXYLATE CHLORIDE

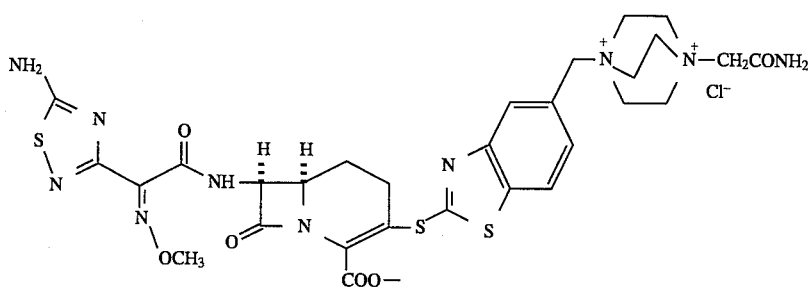

Step 1
4'-methoxybenzyl 7β-[2-(5-amino-1,2,4-thiadiazol-3-yl)-2-Z-methoxyimino]acetamido-3 -(5-chloromethyl-2-benzthiazolthio)-1-carba-1-dethiaceph-3-em-4-carboxylate 4'-Methoxybenzyl 7β-ammonium-3-(5-chloromethyl-2-benzthiazolylthio)-1-carba-1-dethiaceph-3-em-4-carboxylate p-toluenesulfonate (0.1 mmole) is taken up in $CH_2Cl_2$ and cooled to −10° C. under $N_2$. 2-(5-amino-1,2,4-thiadiazol-3-yl)-(2-Z-2-methoxyimino)]acetyl chloride (24 mg, 0.11 mmole) is added followed by pyridine (16 μl, 0.22 mmole). The reaction mixture is stirred at −10° C. for 0.5 hr. The reaction mixture is diluted with EtOAc and washed with water, dried over $MgSO_4$ and evaporated to give the crude product.

Step 2
4'-methoxybenzyl 7β-[2-(5-amino-1,2,4-thiadiazol-3-yl)-2-Z-methoxyimino]acetamido-3-(5-iodomethyl-2-benzthiazolylthio)-1-carba-1-dethiaceph-3-em-4-carboxylate The product from Step 1 is treated under the conditions of Example 5, Step 2 to give the desired product.

Step 3
4'-methoxybenzyl 7β-[2-(5-amino-1,2,4-thiadiazol-3-yl)-2-Z-methoxyimino]acetamido-3-{[5-(4-carbamoylmethyl-1,4-diazoniabicyclo [2.2.2])oct-1-yl)methyl]-benzthiazol-2-yl-}thio-1-carba-1-dethiaceph-3-em4-carboxylate bis (trifluoromethanesulfonate)

The product from Step 2 is treated under the conditions of Example 5, Step 3 to give the desired product.

Step 4
7β-[2-(5-amino-2,4-thiadiazol-3-yl)-(2-Z-2-methoxyimino)]acetamido-3-{[5-(4-carbamoylmethyl-1,4-diazoniabicyclo [2.2.2])oct-1-yl)methyl]-benzthiazol-2-yl-}thio-1-carba-1-dethiaceph-3-em-4-carboxylate chloride The product from Step 3 is treated under the conditions of Example 5, Step 4 to give the desired product.

EXAMPLE 16

7B-[(Z)-2-(2-AMINOTHIAZOL-4-YL)-3-TERTBUTYLMETHYLACRYLAMIDO]-[-3-{[5-(4-CARBAMOYLMETHYL-1,4-DIAZONIABICYCLO [2.2.2])OCT-1YL)METHYL]BENZTHIAZOL-2-YL-}THIO-1-CARBA-1-DETHIACEPH-3-EM-4-CARBOXYLATE CHLORIDE

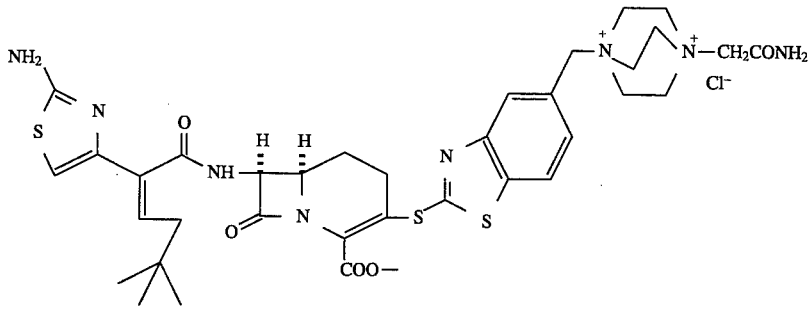

Substitution of (Z)-2-(triphenylmethylaminothiazol-4-yl)-2-Z-2-fiuoroethoxyimino)-acetic acid hydrochloride by (Z)-2-(2-triphenylmethylaminothiazol-4-yl)-3-tert-butylmethylacrylic acid in the procedure of example 4, step 1, followed by the procedure of steps 2 to 4 gives the desired product.

EXAMPLE 17

7B-[(Z)-2-(2-AMINOTHIAZOL4-YL)-3-CYCLOPENTYLMETHYLACRLAMIDO]-3-{[5-(4-CARBAMOYLMETHYL-1,4-DIAZONIABICYCLO [2.2.2])OCT-1)METHYL]-BENZTHIAZOL-2-YL-}THIO1-CARBA-1-DETHIACEPH-3-EM4-CARBOXYLATE CHLORIDE

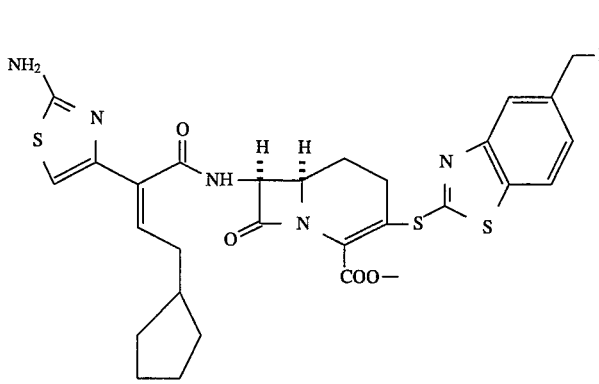

Substitution of (Z)-2-(triphenylmethylaminothiazo4-yl))-2-Z-2-fluoroethoxyimino)-acetic acid hydrochloride by (Z)-2-(2tritylaminothiazol-4yl)-3-cyclopentylmethylacrylic acid in the procedure of example 4, step 1, followed by the procedure of steps 2 to 4 gives the desired product.

EXAMPLE 18

7B-[(Z)-2-(2-AMINOTHIAZOL-4-YL)-3CYCLOHEXYLACRLAMIDO]-3-{[5-(4-CARBAMOYLMETHYL-1,4-DIAZONIABICYCLO[2.2.2])OCT-1-YL)METHYL]-BENZTHIAZOL-2-YL-}THIO-1-CARBA-1-DETHIACEPH-3-EM-4-CARBOXYLATE CHLORIDE

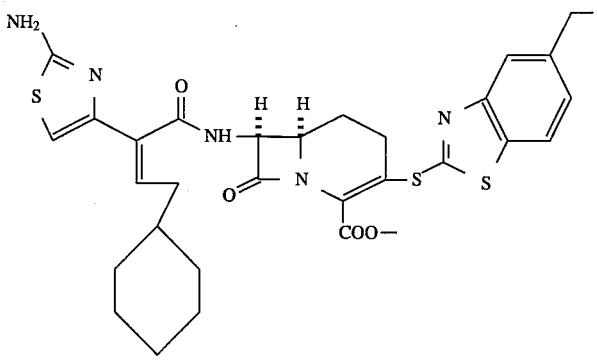

Substitution of (Z)-2-(triphenylmethylaminothiazol4-yl))-2-Z-2-fluoroethoxyimino)-acetic acid hydrochloride by ((Z)-2-(2-tritylaminothiazol-4-yl)-3-cyclohexylacrylic acid in the procedure of example 4, step 1, followed by the procedure of steps 2 to 4 gives the desired product.

What is claimed is:

1. A compound represented by formula I:

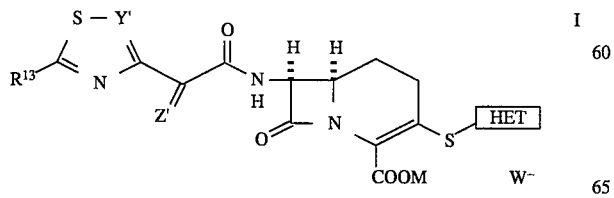

or a pharmaceutically acceptable salt or solvate thereof, wherein:

$Y'$ represents CH or N;

M represents hydrogen, a negative charge, a biolabile ester forming group or a carboxyl protecting group;

$R^{13}$ represents $R^1$ or $N(R^1)_2$;

W− is present or absent, and when present, represents a negatively charged counterion;

$Z'$ represents (a) $CR^{y'}R^{z'}$ wherein $R^{y'}$ and $R^{z'}$ independently represent H, $C_{1-6}$ alkyl or $C_{3-8}$ cycloalkyl, each optionally substituted with 1–3 groups selected from $R^{e'}$, or (b) N substituted with $OR^1$ with $R^1$ equal to H, $C_{1-6}$ alkyl or $C_{1-6}$ alkyl substituted with from 1–3 groups selected from $R^{e'}$; $C_{3-8}$ cycloalkyl; $C_{3-8}$ cycloalkenyl; $C_{3-8}$ cycloalkyl substituted with 1–3 groups selected from $R^{e'}$, or $C_{3-8}$ cycloalkenyl substituted with 1–3 groups selected from $R^{e'}$;

$R^{e'}$ represents a member selected from the group consisting of:

a) —$CF_3$;

b) a halogen atom selected from the group consisting of —Br, —Cl, —F and —I;

c) —$OC_{1-4}$ alkyl, wherein the alkyl portion thereof is optionally substituted by 1–3 groups selected from $R^q$. $R^q$ is selected from the group consisting of hydroxy, methoxy, cyano, —$C(O)NH_2$, —$C(O)NHC_{1-4}$ alkyl, —$C(O)N(C_{1-4}$ alkyl$)_2$, —$OC(O)NH_2$, —CHO, —$OC(O)NHC_{1-4}$ alkyl, —$OC(O)N(C_{1-4}$ alkyl$)_2$, —$SO_2NH_2$, —$SO_2N(C_{1-4}$ alkyl$)_2$, —$S(O)C_{1-4}$ alkyl, —$SO_2C_{1-4}$ alkyl, —F, —$CF_3$, —$SO3M^b$ with $M^b$ representing H or an alkali metal, and —$CO_2M^a$, where $M^a$ is H, alkali metal, methyl or phenyl; tetrazolyl (where the point of attachment is the carbon atom of the tetrazole ring and one of the nitrogen atoms is optionally substituted by 1–3 of the other $R^q$ groups as defined above);

d) —OH;

e) —OC(O)$R^s$, where $R^s$ is $C_{1-4}$ alkyl or phenyl, each of which is optionally substituted by 1–3 groups $R^q$ as defined above;

f) —OC(O)N($R^{y''}$)$R^{z''}$, where $R^{y''}$ and $R^{z''}$ are independently H, $C_{1-4}$ alkyl, (optionally substituted by 1–3 $R^q$ groups as defined above), or are taken together to represent a 3- to 5-membered alkylidene radical which forms a ring (optionally substituted with $R^q$ as defined above), or a 2- to 4-membered alkylidene radical interrupted by —O—, —S—, —S(O)— or —S(O)$_2$— which forms a ring, said ring being optionally substituted with 1–3 groups $R^q$ as defined above;

g) —S(O)$_n$—$R^s$, where n=0–2, and $R^s$ is defined above;

h) —SO$_2$N($R^{y''}$)$R^{z''}$, where $R^{y''}$ and $R^{z''}$ are as defined above;

i) —N$_3$;

j) —N$R^x_{(0-1)}R^yR^z$ wherein $R^x$, $R^y$ and $R^z$ independently represent H, $C_{1-4}$ alkyl or $C_{1-4}$ alkyl substituted with from 1–3 $R^q$ groups, or $R^x$, $R^y$ and $R^z$ are taken together to represent either a 3- to 7- membered heterocyclic or heteroaryl ring, optionally substituted with 1–3 $R^q$ groups, or a 2- to 4-membered alkylidene radical interrupted by N, O or S(O)$_x$ with x equal to 0, 1 or 2, to form a ring, said alkylidene being optionally substituted with from 1 to 3 $R^q$ groups, such that when $R^x$, $R^y$ and $R^z$ are present, N$R^xR^yR^z$ is a quaternary nitrogen containing group which may be part of a ring, or $R^x$, $R^y$ and $R^z$ am taken in combination to represent a $C_4$ to $C_{10}$ alkanetriyl group, optionally substituted with 1–3 $R^q$ groups, said alkanetriyl group being optionally interrupted with 1–3 heteroatoms selected from N$^+R^t$, O and S(O)$_x$ with x and $R^t$ as defined above;

k) —N($R^t$)C(O)H, where $R^t$ is H or $C_{1-4}$ alkyl, said alkyl group being optionally substituted with 1–3 groups $R^q$ as defined above;

l) —N($R^t$)C(O)$C_{1-4}$ alkyl, wherein $R^t$ is as defined above;

m) —N($R^t$)C(O)O$C_{1-4}$ alkyl, wherein $R^t$ is as defined above;

n) —N($R^t$)C(O)N($R^y$)$R^z$ where $R^t$, $R^y$ and $R^z$ are defined above;

o) —N($R^t$)SO$_2R^s$, where $R^s$ and $R^t$ are as defined above;

p) —CN;

q) a formyl or acetalized formyl radical which is —C(O)H or —CH(OCH$_3$)$_2$;

r) —C(OCH$_3$)$_2$ $C_{1-4}$ alkyl, where the alkyl is optionally substituted by 1–3 groups $R^q$ as defined above;

s) —C(O)$R^s$, where $R^s$ is as defined above;

t) —(C=NO$R^{z''}$)$R^{y''}$ where $R^{y''}$ and $R^{z''}$ are as defined above, except they may not be joined together to form a ring;

u) —C(O)O$C_{1-4}$ alkyl, where the alkyl is optionally substituted by 1–3 groups $R^q$ as defined above;

v) —C(O)N($R^{y''}$)$R^{z''}$, where $R^{y''}$ and $R^{z''}$ are as defined above;

w) —C(O)N(O$R^{y''}$)$R^{z''}$, where $R^{y''}$ and $R^{z''}$ are as defined above, except they may not be joined together to form a ring;

x) —C(S)N($R^{y''}$)$R^{z''}$ where $R^{y''}$ and $R^{z''}$ are as defined above;

y) —COO$M^a$ where $M^a$ represents H, $C_{1-4}$ alkyl, phenyl or an alkali metal;

z) —SCN;

aa) —SCF$_3$;

ab) tetrazolyl, where the point of attachment is the carbon atom of the tetrazole ring and one of the nitrogen atoms is substituted by hydrogen, an alkali metal or a $C_{1-4}$ alkyl optionally substituted by $R^q$ as defined above;

ac) an anionic function which is selected from the group consisting of: P=O(O$M^a$)$_2$; P=O(O$M^a$)-[O($C_{1-4}$ alkyl)]; P=O(O$M^a$)-($C_{1-4}$ alkyl); P=O(O$M^a$)N($R^{y''}$)$R^{z''}$; P=O(O$M^a$)NH$R^x$; SO$_2M^a$; SO$_3M^a$; SO$_2$N$M^a$CON($R^{y''}$)$R^{z''}$, and SO$_2$N$M^a$CN, where $R^x$ is phenyl or heteroaryl, said heteroaryl group being a monocyclic, aromatic hydrocarbon group having 5 or 6 ring atoms, in which a carbon atom is the point of attachment, one of the carbon atoms has been replaced by a nitrogen atom, one carbon atom is optionally replaced by a heteroatom selected from O or S, and from 1 to 3 additional carbon atoms are optionally replaced by nitrogen heteroatoms, and where the phenyl and heteroaryl are optionally substituted by 1–3 groups $R^q$, said $R^q$, $M^a$, $R^{y''}$ and $R^{z''}$ are as defined above;

ad) a $C_{3-7}$ cycloalkyl group;

ae) a $C_{5-7}$ cycloalkyl group in which one of the carbon atoms in the ring is replaced by a heteroatom selected from O, S, NH, or N($C_{1-4}$ alkyl) and in which one additional carbon may be replaced by the NH or N($C_{1-4}$ alkyl), and in which at least one carbon atom adjacent to each nitrogen heteroatom has both of its attached hydrogen atoms replaced by one oxygen thus forming a carbonyl moiety and them are one or two carbonyl moieties present in the ring;

af) a $C_{2-4}$ alkenyl radical, optionally substituted by 1–3 of the substituents a) to ac) above and phenyl which is optionally substituted by $R^q$ as defined above;

ag) a $C_{2-4}$ alkynyl radical, optionally substituted by 1–3 of the substituents a) to ac) above;

ah) a $C_{1-4}$ alkyl radical;

ai) a $C_{1-4}$ alkyl group substituted by 1–3 of the substituents a)–aa) above;

aj) a $C_{1-4}$ alkyl radical substituted with 1–3 groups selected from aryl, oxime, heteroaryl, $C_{3-7}$ cycloalkyl and heterocycloalkyl, each of which is unsubstituted or substituted with 1 to 3 $R^q$ groups;

ak) a $C_{3-7}$ cycloalkyl radical substituted with 1–3 of the substituents a)–aa) above;

al) a $C_{3-7}$ heterocycloalkyl radical substituted with 1–3 of the substituents a)–aa) above;

am) a $C_{6-10}$ aryl radical;

an) a $C_{6-10}$ aryl radical substituted with 1–3 of the substituents a)–aa) above;

ao) a 6–10 membered heteroaryl radical; and ap) a 6–10 membered heteroaryl radical substituted with 1–3 of the substituents a)–aa) above;

$$\boxed{\text{HET}}$$

represents a heterocyclic group with from one to three positively charged atoms, and is selected from the group consisting of:

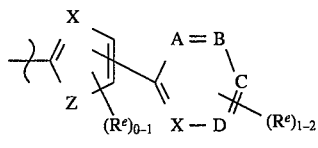

and

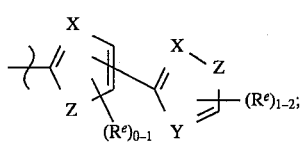

wherein

represents the point of attachment to S;

A, B, C, D, X and Y independently represents C or N;

Z represents O, S or N, such that when Z is absent, at least one of A, B, C, D, X and Y represents N;

one to three $R^e$ groups are present; one $R^e$ represents —R* and the others represent H, $R^{e'}$ or $R^f$; —R* represents one of the groups (a) through (c):

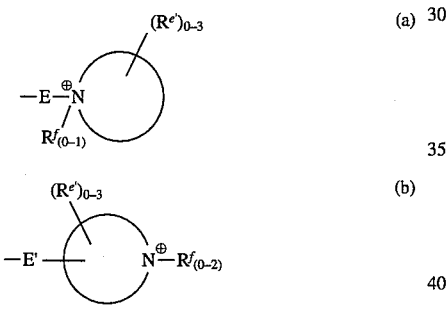

when —R* represents (a)

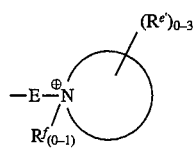

E represents —(CR$^3$R$^4$)$_r$—Q—(CR$^3$R$^4$)$_s$— wherein r is 0–6, s is 1–6;

Q represents a member selected from the group consisting of: a covalent bond, —O—, —S(O)$_x$— with x equal to 0, 1 or 2, —NR$^3$—, —SO$_2$NR$^3$—, —NR$^3$SO$_2$—, —C(O)NR$^3$—, —NR$^3$C(O)—, —CR$^3$=CR$^4$—, —C(O)—, —OC(O)—, —(O)CO—,

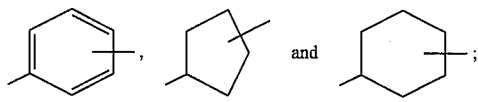

which R$^3$ and R$^4$ independently represent H or C$_{1-4}$ lower alkyl, and (CR$^3$R$^4$)$_s$— is attached to the ring nitrogen;

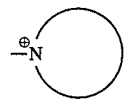

represents a 5 or 6 membered monocyclic heterocycle or an 8–10 membered bicyclic heterocycle, bonded to E through the ring nitrogen and having a substituent group R$^f$ optionally attached to the ring nitrogen, and having 0–3 R$^{e'}$ groups attached to other atoms of the heterocyclic group, said ring nitrogen being tertiary or quaternary by virtue of E, the ring bonds and the optional R$^f$ which may be attached, said heterocyclic group being aromatic, partially aromatic or non-aromati, said heterocycle further containing 0–3 additional nitrogen atoms and 0–1 oxygen or sulfur atom;

each R$^f$ independently represents hydrogen, —NH$_2$, —O—, —C$_{1-4}$ alkyl, optionally substituted with 1–3 groups selected from R$^q$; —C$_{3-7}$ cycloalkyl, optionally substituted with 1–3 groups selected from R$^q$; —C$_{5-7}$ cycloalkyl group in which one of the carbon atoms in the ring is replaced by a heteroatom selected from O, S, NH, or N(C$_{1-4}$ alkyl) and in which one additional carbon may be replaced by the NH or N(C$_{1-4}$ alkyl), and in which at least one carbon atom adjacent to each nitrogen heteroatom has both of its attached hydrogen atoms replaced by one oxygen thus forming a carbonyl moiety and there am one or two carbonyl moieties present in the ring; a C$_{2-4}$ alkenyl radical, optionally substituted by 1–3 substituents selected from R$^q$; a C$_{2-4}$ alkynyl radical, optionally substituted by 1–3 substituents selected from R$^q$; a C$_{1-4}$ alkyl radical substituted with 1–3 groups selected from aryl, oxime, heteroaryl, C$_{3-7}$ cycloalkyl and heterocycloalkyl, each of which is unsubstituted or substituted with 1 to 3 groups selected from R$^q$; a C$_{3-7}$ cycloalkyl radical optionally substituted with 1–3 substituents selected from R$^q$; a C$_{6-10}$ aryl radical, optionally substituted with 1–3 substituents selected from R$^q$; and a 6–10 membered heteroaryl group, optionally substituted with 1-14 3 substituents selected from R$^q$;

when—R* represents

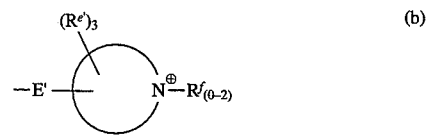

E' represents —(CR$^3$R$^4$)$_{m'}$—Q—(CR$^3$R$^4$)$_{m'}$— with each m' independently equal to 0–6, and Q, R$^3$ and R$^4$ as defined above, except that when each m' is 0, Q is not a covalent bond, and —(CR$^3$R$^4$)$_{m'}$ attached to the heterocyclic ring;

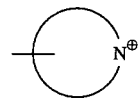

represents a 5 or 6 membered monocyclic heterocycle or an 8–10 membered bicyclic heterocycle, said heterocycle being aromatic, partially aromatic or non-aromatic, bonded to E' through an atom other than the ring nitrogen, and having 0–2 R$^f$ groups attached to the ring nitrogen, said nitrogen in the heterocycle being tertiary or quaternary by virtue of the ring bonds and the optional R$^f$ groups which may be attached, said heterocycle further containing 0–1 oxygen or sulfur atom and 0–2 additional nitrogen atoms therein;

$R^{e'}$ and $R^f$ are as defined above;
when —R* represents (c) —E $_p$ —N$^+$R$^{10}$R$^{11}$R$^{12}_{(0-1)}$, E is as defined above and p is an integer 0 or 1;

R$^{10}$, R$^{11}$ and when present, R$^{12}$, are independently H, C$_{1-4}$ alkyl or C$_{1-4}$ alkyl substituted with 1–3 R$^q$ groups;

or R$^{10}$ and R$^{11}$ may be taken together to represent a C$_3$–C$_5$ alkylidene radical to form a ring (optionally substituted with 1–3 R$^q$ groups as defined below), uninterrupted or interrupted by O, S, S(O), SO$_2$, N(O)R$^{e'}$ or N$^+$(R$^{e'}$)$_{1-2}$, where R$^{e'}$ is as previously defined, or R$^{10}$, R$^{11}$ and R$^{12}$ may be taken in combination to represent a C$_4$ to C$_{10}$ alkanetriyl group, optionally substituted with 1–3 R$^{e'}$ groups, said alkanetriyl group being optionally interrupted with 1–3 heteroatoms selected from N$^+$R$^{e'}$, N$^+$R$^f$, O and S(O)$_x$ with x, R$^{e'}$ and R$^f$ as defined above.

2. A compound in accordance with claim 1 wherein Y' represents N.

3. A compound in accordance with claim 1 wherein Y' represents C.

4. A compound in accordance with claim 1 wherein X represents a nitrogen atom.

5. A compound in accordance with claim 1 wherein X represents nitrogen and Z represents sulfur.

6. A compound in accordance with claim 1 wherein X represents a nitrogen atom, and Y and Z represent carbon.

7. A compound in accordance with claim 1 wherein

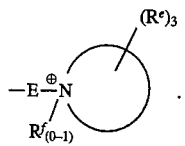

8. A compound in accordance with claim 1 wherein

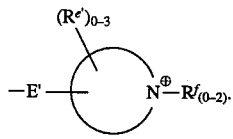

9. A compound in accordance with claim 1 wherein —R* represents (c) —E$_p$—N$^+$R$^{10}$R$^{11}$R$^{12}_{(0-1)}$.

10. A compound in accordance with claim 1 wherein R$^1$ and HET are selected in accordance with the following table:

TABLE I

[Structural formula showing cephalosporin-like compound with H$_2$N-thiazole, CO—NH, N—OR$^1$, COO—, S—HET groups]

| | R$^1$ | S—HET |
|---|---|---|
| 75 | CH$_2$—CH$_2$—F | [structure: phenyl-thiazole linked to piperazinium with N$^+$—CH$_2$CONH$_2$] |
| 76 | CH$_2$—CH$_2$—F | [structure: phenyl-thiazole linked to imidazolium with propyl-NH$_3^+$] |

11. A compound in accordance with claim 1 wherein R$^1$ and HET are selected in accordance with the following table:

TABLE II

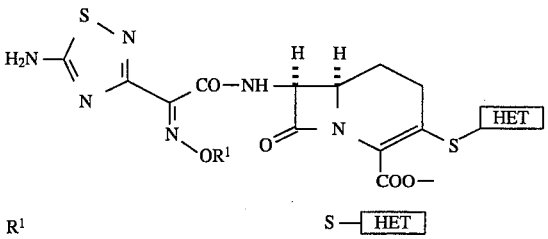

| | R¹ | S—[HET] |
|---|---|---|
| 75 | CH₂—CH₂—F | 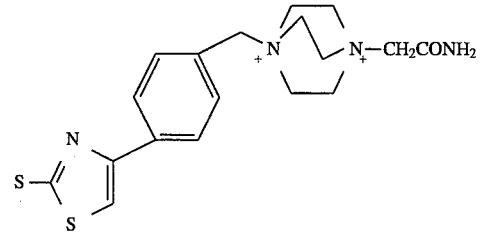 |
| 76 | CH₂—CH₂—F | 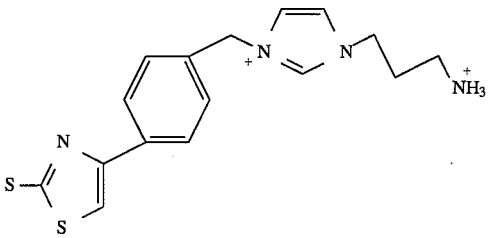 |

12. A pharmaceutical composition comprised of a compound as described in claim 1 in combination with a pharmaceutically acceptable carrier.

13. A method of treating a bacterial infection in a mammalian patient in need of such treatment, comprising administering to said patient a compound as described in claim 1 in an amount effective to treat said bacterial infection.

* * * * *